(12) United States Patent
Schmitt-Willich et al.

(10) Patent No.: US 9,017,645 B2
(45) Date of Patent: Apr. 28, 2015

(54) HOMOGLUTAMIC ACID DERIVATIVES

(75) Inventors: Heribert Schmitt-Willich, Berlin (DE); Niels Böhnke, Berlin (DE); Norman Koglin, Berlin (DE); Andre Müller, Berlin (DE); Mathias Berndt, Berlin (DE); Matthias Friebe, Berlin (DE); Lutz Lehmann, Berlin (DE)

(73) Assignee: Piramal Imaging SA, Matran (CH)

( * ) Notice: Subject to any disclaimer, the term of this patent is extended or adjusted under 35 U.S.C. 154(b) by 0 days.

(21) Appl. No.: 13/509,062

(22) PCT Filed: Nov. 8, 2010

(86) PCT No.: PCT/EP2010/067011
§ 371 (c)(1),
(2), (4) Date: Nov. 30, 2012

(87) PCT Pub. No.: WO2011/057986
PCT Pub. Date: May 19, 2011

(65) Prior Publication Data
US 2013/0071327 A1  Mar. 21, 2013

(30) Foreign Application Priority Data

Nov. 11, 2009 (EP) ..................... 09075500

(51) Int. Cl.
| | | |
|---|---|---|
| A61B 5/055 | (2006.01) | |
| C07C 271/22 | (2006.01) | |
| A61K 49/10 | (2006.01) | |
| A61K 51/04 | (2006.01) | |
| C07B 59/00 | (2006.01) | |
| C07C 229/24 | (2006.01) | |
| C07C 229/30 | (2006.01) | |
| C07C 255/58 | (2006.01) | |

(52) U.S. Cl.
CPC ............. *C07C 271/22* (2013.01); *A61K 49/10* (2013.01); *A61K 51/04* (2013.01); *A61K 51/0402* (2013.01); *C07B 59/001* (2013.01); *C07B 2200/05* (2013.01); *C07C 229/24* (2013.01); *C07C 229/30* (2013.01); *C07C 255/58* (2013.01)

(58) Field of Classification Search
USPC .......................................................... 424/9.3
See application file for complete search history.

(56) References Cited

PUBLICATIONS

Birkofer et al (Synthesis of tritium-labeled amino acids of high specific activity, Chemische Berichte, 96, 1963, 1373-81).*
Gerig (Fluorine NMR, Dept of Chemistry UCSB, updated 2001).*
EP Communication pursuant to Article 94(3) EPC in corresponding European Patent Application No: 10 773 350.3 Office Action dated Apr. 11, 2014.

* cited by examiner

*Primary Examiner* — Benjamin Packard
(74) *Attorney, Agent, or Firm* — Millen, White, Zelano & Branigan, P.C.

(57) ABSTRACT

This invention relates to homoglutamic acid derivatives suitable for labeling or already labeled with $^{18}F$ or $^{19}F$, methods of preparing such compounds, compositions comprising such compounds, kits comprising such compounds or compositions and uses of such compounds, compositions or kits for diagnostic imaging.

16 Claims, 7 Drawing Sheets

HOMOGLUTAMIC ACID DERIVATIVES

FIELD OF INVENTION

Figure 1:
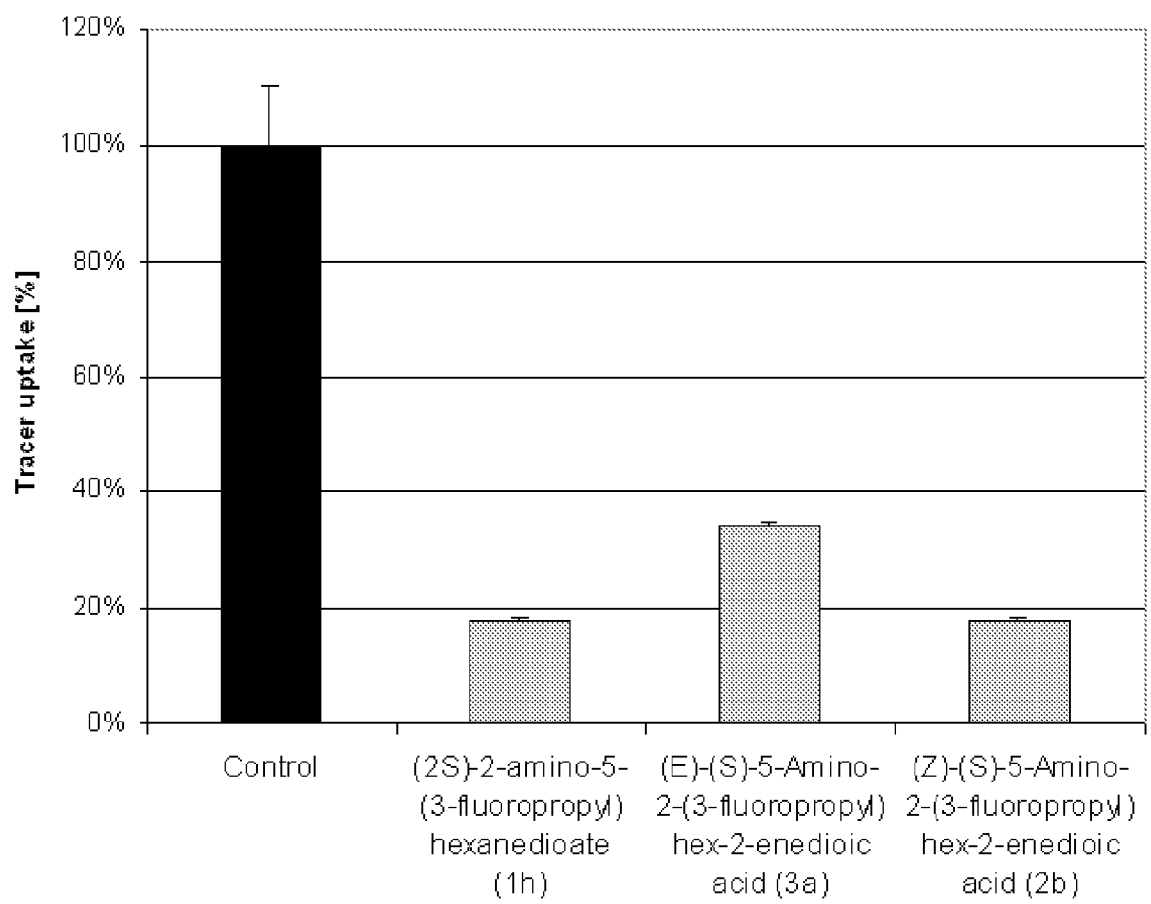

This invention relates to homoglutamic acid derivatives suitable for labeling or already labeled with $^{18}$F or $^{19}$F, methods of preparing such compounds, compositions comprising such compounds, kits comprising such compounds or compositions and uses of such compounds, compositions or kits for diagnostic imaging.

BACKGROUND

The invention relates to the subject matter referred to in the claims, i.e. homoglutamic acid derivatives of the general formulas I and/or II, their precursors of the formula III, their use and their preparation processes.

The early diagnosis of malignant tumour diseases plays an important role in the survival prognosis of a tumour patient. For this diagnosis, non-invasive diagnostic imaging methods are an important aid. In the last years, in particular the PET (Positron Emission Tomography) technology has been found to be particularly useful. The sensitivity and specificity of the PET technology depends essentially on the signal-giving substance (tracer) used and on its distribution in the body. In the hunt for suitable tracers, one tries to make use of certain properties of tumours which differentiate tumour tissue from healthy surrounding tissue. The preferred commercial isotope used for PET applications is $^{18}$F. Owing to the short half-life of less than 2 hours, $^{18}$F is particularly demanding when it comes to the preparation of suitable tracers. This isotope does not allow for complicated long synthesis routes and purification procedures, since otherwise a considerable amount of the radioactivity of the isotope will already have faded away before the tracer can be used for diagnosis. Accordingly, it is frequently not possible to apply established synthesis routes for non-radioactive fluorinations to the synthesis of $^{18}$F tracers. Furthermore, the high specific activity of $^{18}$F (about 80 GBq/nmol) leads to very low substance amounts of [$^{18}$F]-fluoride for the tracer synthesis, which in turn requires an extreme excess of precursor, making the result of a radio synthesis strategy based on a non-radioactive fluorination reaction unpredictable.

FDG ([$^{18}$F]-2-Fluorodeoxyglucose)-PET is a widely accepted and frequently used auxiliary in the diagnosis and further clinical monitoring of tumour disorders. Malignant tumours compete with the host organism for glucose as nutrient supply (Warburg O., Über den Stoffwechsel der Carcinomzelle [The metabolism of the carcinoma cell], *Biochem. Zeitschrift* 1924; 152: 309-339; Kellof G., Progress and Promise of FDG-PET Imaging for Cancer Patient Management and Oncologic Drug Development, *Clin. Cancer Res.* 2005; 11(8): 2785-2807).

Compared to the surrounding cells of the normal tissue, tumour cells usually have an increased glucose metabolism. This is exploited when using fluorodeoxyglucose (FDG), a glucose derivative which is increasingly transported into the cells, where, however, it is metabolically captured as FDG 6-phosphate after phosphorylation ("Warburg effect"). Accordingly, $^{18}$F-labelled FDG is an effective tracer for detecting tumour disorders in patients using the PET technology. In the hunt for novel PET tracers, recently, amino acids have been employed increasingly for $^{18}$F PET imaging (for example (review): *Eur. J. Nucl. Med. Mol. Imaging* May 2002; 29(5): 681-90). Here, some of the $^{18}$F-labelled amino acids are suitable for measuring the rate of protein synthesis, but most other derivatives are suitable for measuring the direct cellular uptake in the tumour. Known $^{18}$F-labelled amino acids are derived, for example, from tyrosine amino acids, phenylalanine amino acids, proline amino acids, asparagine amino acids and unnatural amino acids (for example *J. Nucl. Med.* 1991; 32: 1338-1346, *J. Nucl. Med.* 1996; 37: 320-325, *J. Nucl. Med.* 2001; 42: 752-754 and *J. Nucl. Med.* 1999; 40: 331-338). $^{18}$F-labelled homoglutamic acid derivatives are not known up to date.

The PET tracers currently used in tumour diagnosis have some undisputed disadvantages: thus, FDG is preferably accumulated in cells having an elevated glucose metabolism; however, under different pathological and physiological conditions, as also in elevated glucose metabolism in the cells and tissues involved, for example infection sites or wound healing (summarized in *J. Nucl. Med. Technol.* (2005), 33, 145-155). Frequently, it is still difficult to ascertain whether a lesion detected via FDG-PET is really of neoplastic origin or is the result of other physiological or pathological conditions of the tissue. Overall, the diagnosis by FDG-PET in oncology has a sensitivity of 84% and a specificity of 88% (Gambhir et al., "A tabulated summary of the FDG PET literature", *J. Nucl. Med.* 2001, 42, 1-93S). The imaging of brain tumours, for example, is very difficult owing to the high accumulation of FDG in healthy brain tissue.

In some cases, the $^{18}$F-labelled amino acid derivatives currently known are well suited for the detection of tumours in the brain ((review): *Eur. J. Nucl. Med. Mol. Imaging.* 2002 May; 29(5): 681-90); however, in the case of other tumours, they are not able to compete with the imaging properties of the "Goldstandard" [$^{18}$F]2-FDG. The metabolic accumulation and retention of the current F-18-labelled amino acids in tumour tissue is generally lower than of FDG. In addition, the preparation of isomerically pure F-18-labelled non-aromatic amino acids is chemically very demanding.

Similarly to glucose, for glutamic acid and glutamine, too, an increased metabolism in proliferating tumour cells has been described (Medina, *J. Nutr.* 1131: 2539S-2542S, 2001; Souba, Ann Surg 218: 715-728, 1993). The increased rate of protein and nucleic acid syntheses and the energy generation per se are thought to be the reasons for an increased glutamine consumption of tumour cells. The synthesis of corresponding C-11- and C-14-labelled compounds, which are thus identical to the natural substrate, has already been described in the literature (for example Antoni, Enzyme Catalyzed Synthesis of L-[4-C-11]aspartate and L-[5-C-11]glutamate. *J. Labelled Compd. Radiopharm.* 44; (4) 2001: 287-294 and Buchanan, The biosynthesis of showdomycin: studies with stable isotopes and the determination of principal precursors, *J. Chem. Soc. Chem. Commun.; EN;* 22; 1984; 1515-1517). First tests with the C-11-labelled compound indicate no significant accumulation in tumours.

It is an object of the present invention to provide novel compounds which, in [$^{18}$F]-labelled form, are suitable for PET-based diagnosis.

Problem to be Solved by the Invention and its Solution

Despite the aforementioned advances in finding suitable PET imaging agents for the imaging of tumors, there remains a need for novel amino acid derivatives suitable for exploitation of the advantages of positron emission tomography inter alia with regard to spatial resolution, which also allow for practical use in a clinical PET centre.

Compounds of the present invention feature a fluorine substitution directly attached to the hexanedioic acid scaffold and yet have found to be potent PET imaging agents for the imaging of tumors such as e.g. lung and prostate tumors. It has been surprisingly found that compounds of the present invention show high uptake in the tumor and excellent retention in the tumor over time.

SUMMARY

The invention relates to the subject matter referred to in the claims, i.e. homoglutamic acid derivatives of the general formulas I and/or II, their precursors of the formula III, their use and their preparation processes.

Compounds of formula I2S, IA2S, IB2S, II2S, IIA2S, IIB2S, III2S, IIIA, IIIA2S, IIIB, and IIIB2S are preferred compounds of the present invention.

FIGURES

FIG. 1: Examination of biological activity of compounds from the present invention in a cell-competition-experiment. (NCI-H460 non-small cell lung cancer cells, 10 min incubation with 1 µCi 3H-Glutamic acid in PBS-Puffer, concentration of competitors 1 mM each).

Figure 2:
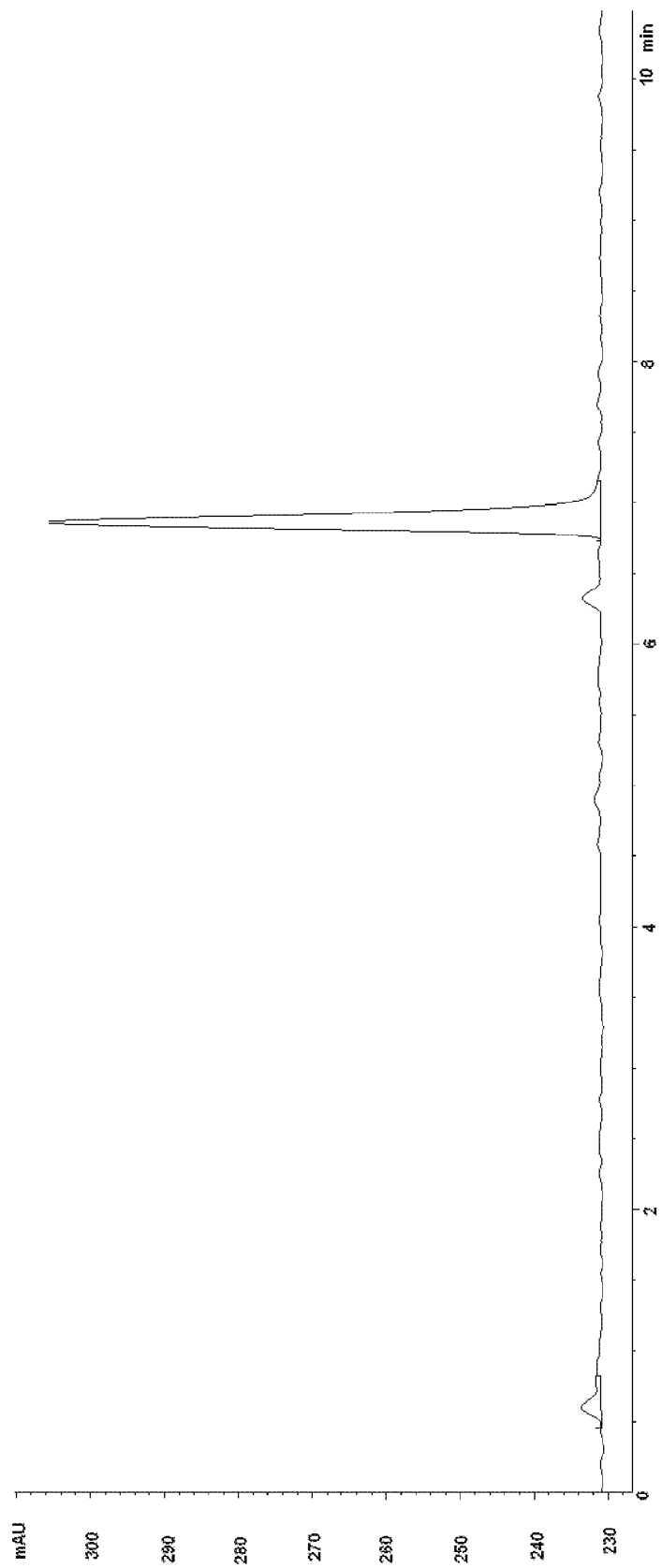

FIG. 2: HPLC of radiolabeled intermediate 1-tert-Butyl 6-ethyl (2S)-2-[(tert-butoxycarbonyl)amino]-5-(3-Fluoropropyl)hexanedioate.

Figure 3:
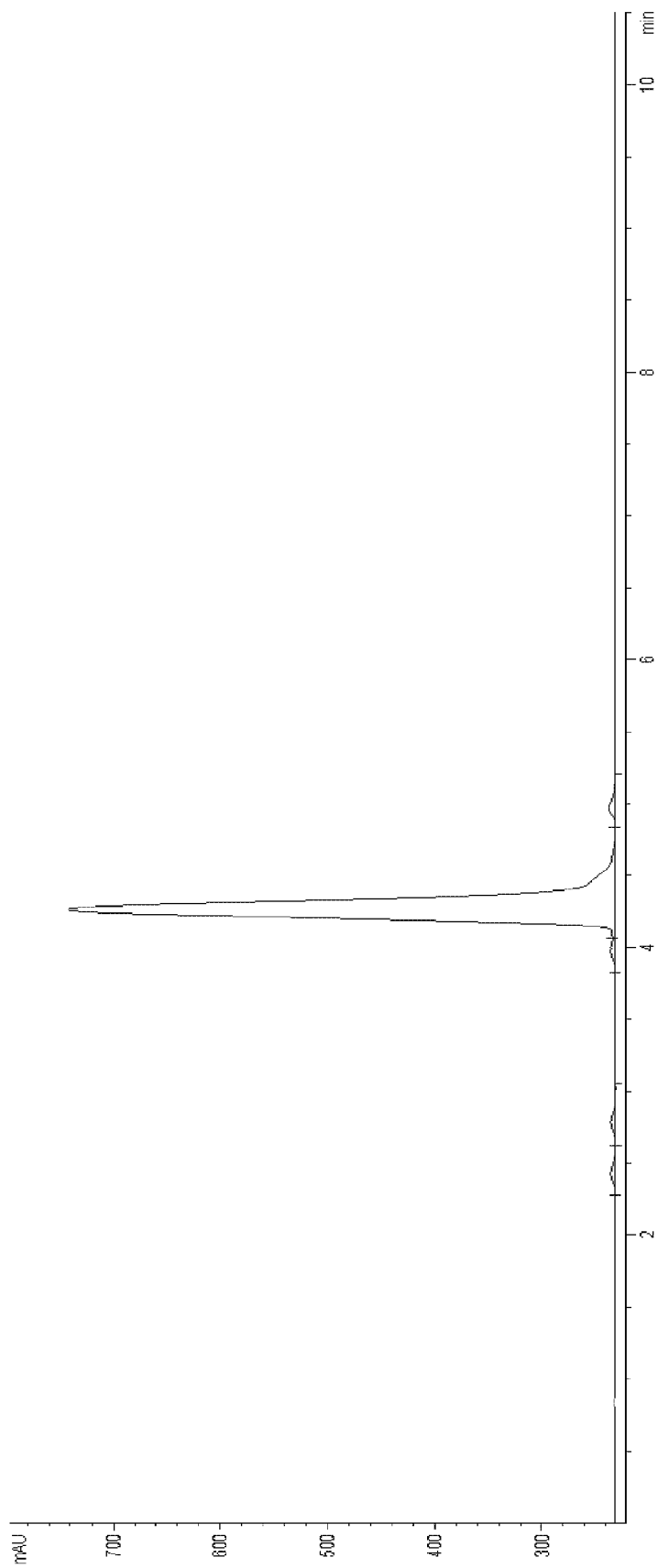

FIG. 3: HPLC of (2S)-2-amino-5-[3-[$^{18}$F]fluoropropyl] hexanedioic acid after derivatization with OPA Phthaldialdehyde Reagent Solution.

Figure 4:
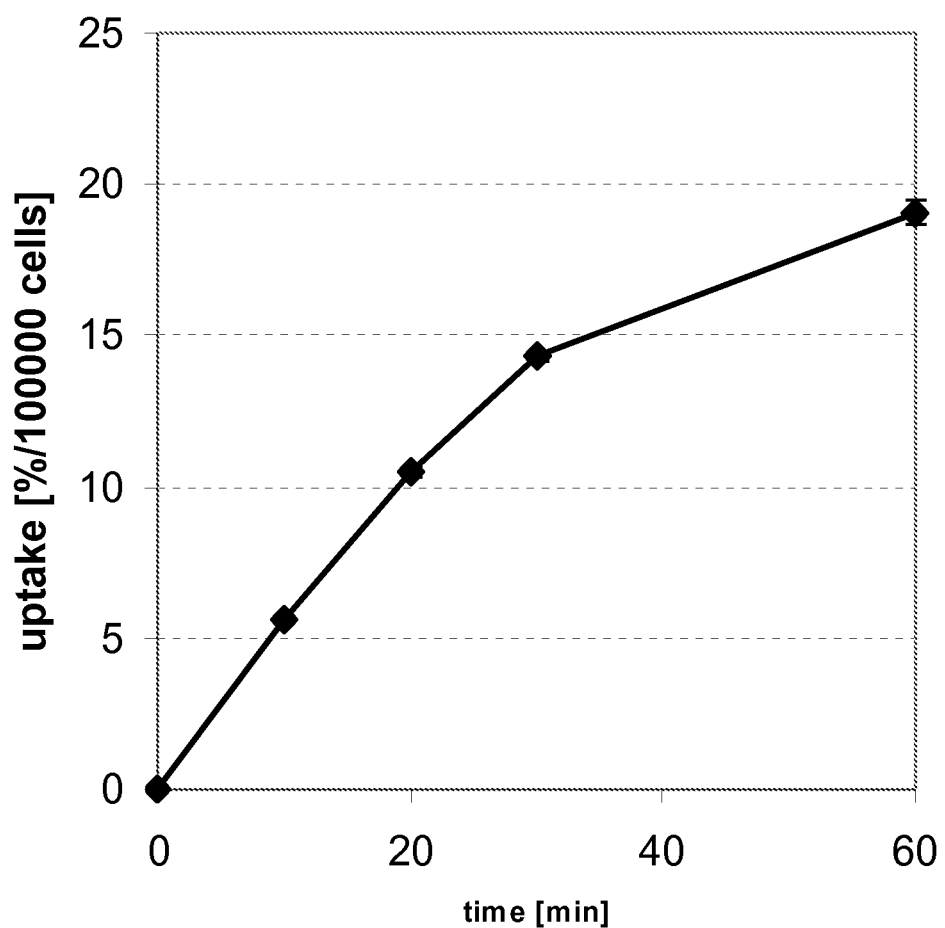

FIG. 4: Time dependent uptake of (2S)-2-amino-5-[3-[$^{18}$F]fluoropropyl]hexanedioic acid was determined. H460 cells were incubated with 0.25 MBq (2S)-2-amino-5-[3-[$^{18}$F]fluoropropyl]hexanedioic acid for up to 60 min and the cell-bound fraction was determined after 10, 20, 30 and 60 min)

Figure 5:
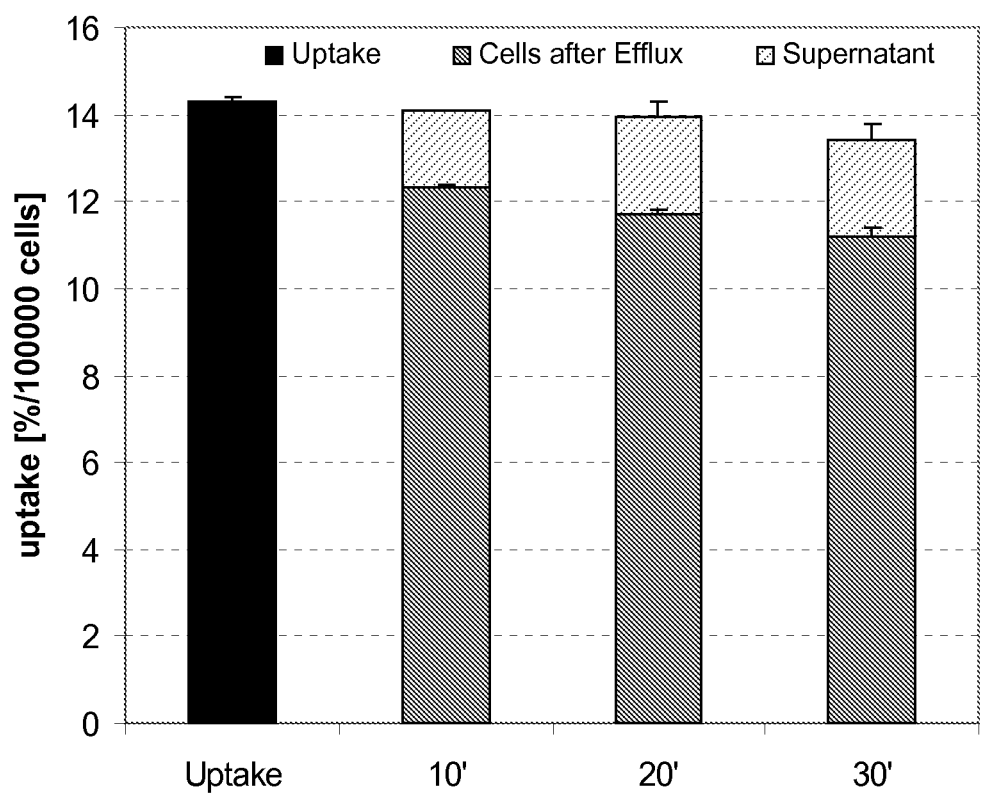

FIG. 5: Retention of (2S)-2-amino-5-[3-[$^{18}$F]fluoropropyl]hexanedioic acid in H460 tumor cells. H460 cells were loaded with 0.25 MBq (2S)-2-amino-5-[3-[$^{18}$F]fluoropropyl] hexanedioic acid for 30 min in PBS/BSA. After washing, the cells were incubated with new buffer (without radioactivity) for additional 10, 20, 30 min. The release of radioactivity into the supernatant as well as the retention inside the cells was determined.

Figure 6:
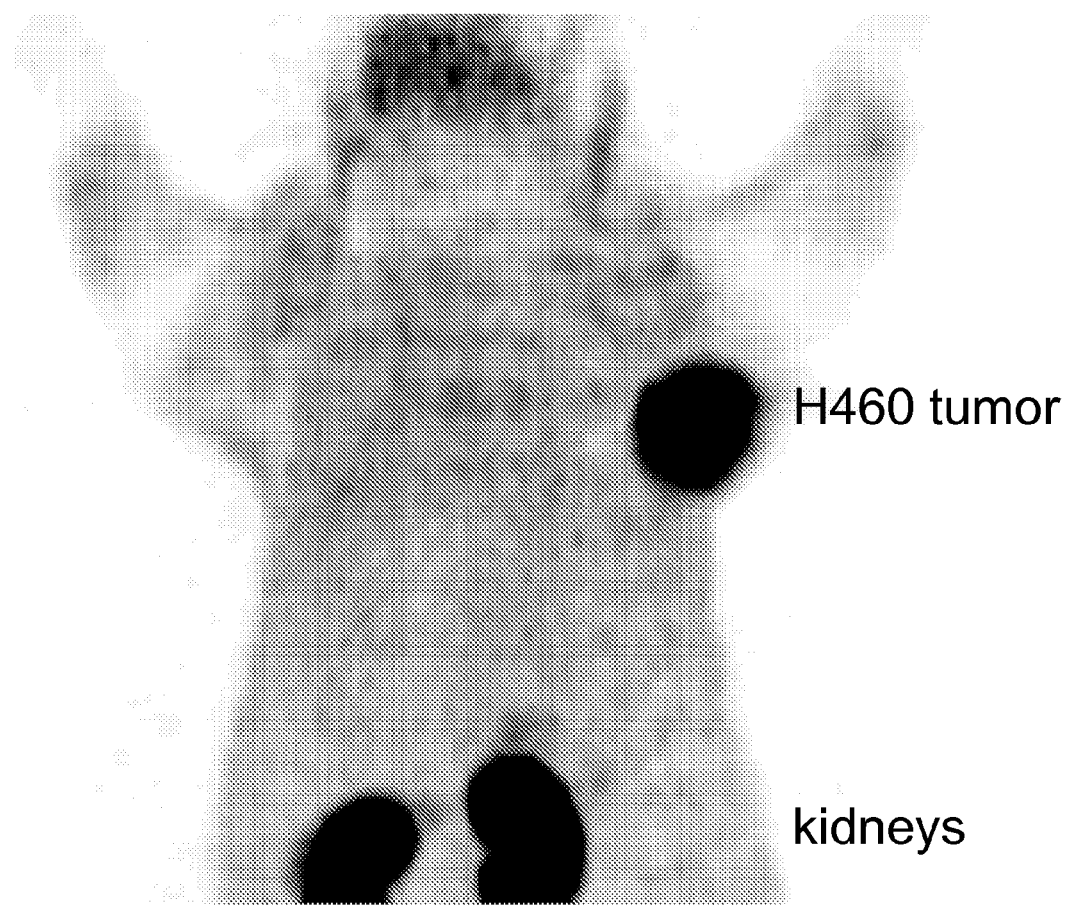

FIG. 6: PET-Imaging of (2S)-2-amino-5-[3-[$^{18}$F]fluoropropyl]hexanedioic acid in H460 tumor bearing rats. 8.35 MBq of radioactive tracer was injected i.v. into rats. PET images were obtained using the Siemens Inveon PET/CT scanner from 60 min p.i. for 10 min.

Figure 7:
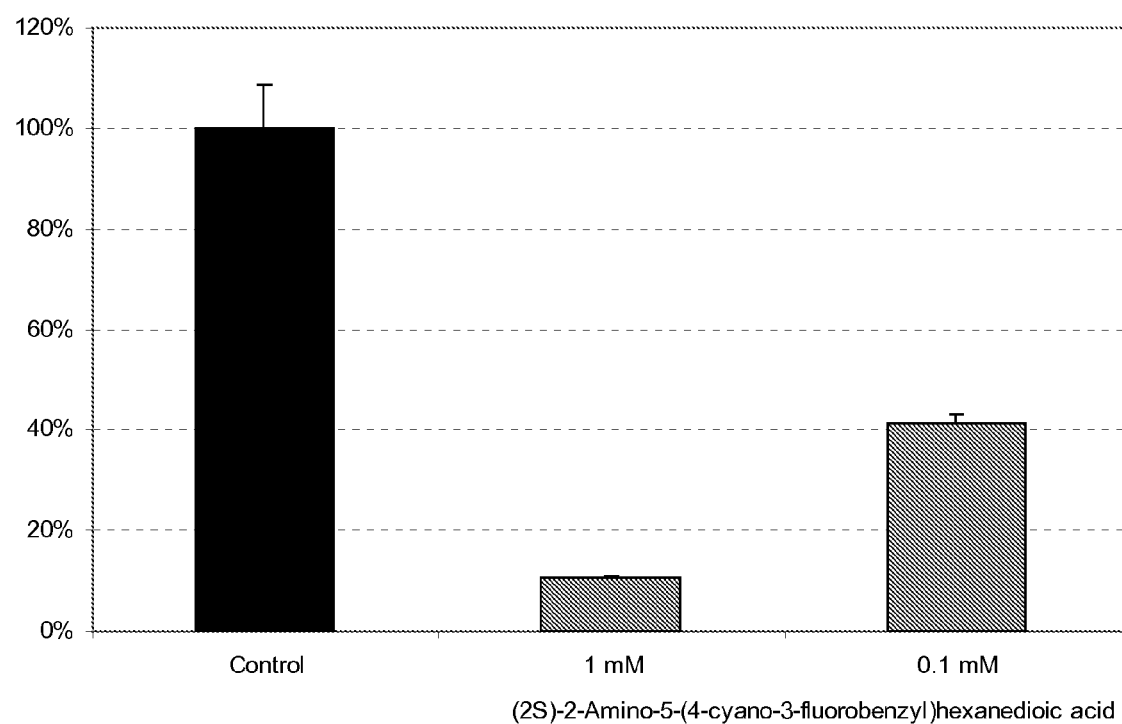

FIG. 7: Biological activity of (2S)-2-Amino-5-(4-cyano-3-fluorobenzyl)hexanedioic acid in a cell-competition-experiment (H460 cells, 30 min incubation with radiolabeled glutamic acid derivative in PBS-Puffer, concentration of competitor 1 mM and 0.1 mM).

DESCRIPTION

In a first aspect, the invention is directed to compounds of the general formula (I)

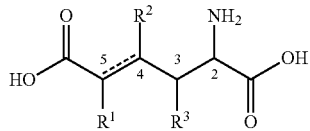

(I)

wherein
$R^1$, $R^2$ and $R^3$ are independently from each other selected from Hydrogen and X with the proviso that one of $R^1$, $R^2$ and $R^3$ is X,
wherein X is
Fluorine atom (F) with the proviso that F is not attached to a sp$^2$ hybridized carbon atom,
branched or straight-chain F—$C_1$-$C_{10}$ alkyl wherein the carbon chain is optionally interrupted by 1 or 2 oxygen atoms with the proviso that there are at least two methylene groups between two oxygen atoms,
branched or straight-chain F—$C_1$-$C_{10}$ alkoxy with the proviso that X is not attached to a sp$^2$ hybridized carbon atom and wherein the carbon chain is optionally interrupted by 1 additional oxygen atom with the proviso that there are at least two methylene groups between two oxygen atoms,
F—$C_6$-$C_{10}$ mono- or bicyclic aryl-$(CH_2)_n$ wherein n=1 to 3, preferably n=1,
F-mono- or bicyclic heteroaryl-$(CH_2)_n$ wherein n=1 to 3, preferably n=1, and wherein heteroaryl comprises 5 to 10 ring atoms wherein 1 or 2 ring atoms are hetero atoms,
F—$C_3$-$C_6$ cycloalkyl with the proviso that F is attached to one of the $CH_2$ groups of the ring,
F—$C_3$-$C_6$ cycloalkyl-$(CH_2)_n$, wherein n=1 to 3, preferably n=1, with the proviso that F is attached to one of the $CH_2$ groups of the ring,
F—$C_6$-$C_{10}$ mono- or bicyclic aryl-$(CH_2)_n$—O, wherein n=1 to 3 preferably n=1 with the proviso that X is not attached to a sp$^2$ hybridized carbon atom or
F-mono- or bicyclic heteroaryl-$(CH_2)_n$—O wherein n=1 to 3, preferably n=1 with the proviso that X is not attached to a sp$^2$ hybridized carbon atom and wherein heteroaryl comprises 5 to 10 ring atoms wherein 1 or 2 ring atoms are hetero-atoms.

Formula I encompasses single isomers, E and Z-isomers, diastereomers and enantiomers, mixtures thereof and suitable salts thereof.

In a first embodiment, the invention is directed to a compound of general formula (I) wherein the Fluorine atom (F) is $^{18}$F isotope.

$R^1$, $R^2$, $R^3$ and X are as described above.
Preferably, $R^2$ and $R^3$ are Hydrogen; and $R^1$ is X.

More preferably, compounds of general formula (I) encompassing the first embodiment are compounds of general formula (I2S).

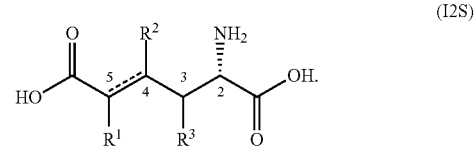

(I2S)

In a second embodiment, the invention is directed to a compound of general formula (I) wherein the Fluorine atom (F) is $^{19}$F isotope.

$R^1$, $R^2$, $R^3$ and X are as described above.
Preferably, $R^2$ and $R^3$ are Hydrogen; and $R^1$ is X.
Preferably, X is
Fluorine atom (F) with the proviso that F is not attached to a sp$^2$ hybridized carbon atom,
branched or straight-chain F—$C_1$-$C_{10}$ alkyl wherein the carbon chain is optionally interrupted by 1 or 2 oxygen atoms with the proviso that there are at least two methylene groups between two oxygen atoms, branched or straight-chain F—$C_1$-$C_{10}$ alkoxy with the proviso that X is not attached to a $sp^2$ hybridized carbon atom and wherein the carbon chain is optionally interrupted by 1 additional oxygen atom with the proviso that there are at least two methylene groups between two oxygen atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, F—$C_6$-$C_{10}$ mono- or bicyclic aryl-$(CH_2)_n$—O, wherein n=1 to 3 preferably n=1 with the proviso that X is not attached to a $sp^2$ hybridized carbon atom or F-mono- or bicyclic heteroaryl-$(CH_2)_n$—O wherein n=1 to 3, preferably n=1 with the proviso that X is not attached to a $sp^2$ hybridized carbon atom and wherein heteroaryl comprises 5 to 10 ring atoms wherein 1 or 2 ring atoms are hetero-atoms.

More preferably, compounds of general formula (I) encompassing the second embodiment are compound of general formula (I2S).

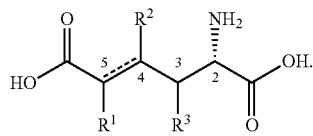

(I2S)

In a third embodiment, the invention is directed to a compound of general formula (I)

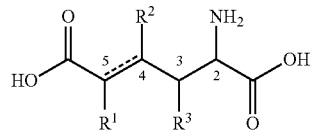

(I)

wherein
$R^2$ and $R^3$ are Hydrogen;
$R^1$ is X,
wherein X is
Fluorine atom (F) with the proviso that there is no double bond between C-4 and C-5, branched or straight-chain F—$C_1$-$C_{10}$ alkyl wherein the alkyl chain is optionally interrupted by 1 or 2 oxygen atoms with the proviso that there are at least two methylene groups between two oxygen atoms, branched or straight-chain F—$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms, F—$C_6$-$C_{10}$ mono- or bicyclic aryl-$(CH_2)_n$ wherein n=1 to 3, preferably n=1, F-mono- or bicyclic heteroaryl-$(CH_2)_n$ wherein n=1 to 3, preferably n=1 and wherein heteroaryl comprises 5 to 10 ring atoms wherein 1 or 2 ring atoms are hetero-atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, F—$C_6$-$C_{10}$ mono- or bicyclic aryl-$(CH_2)_n$—O, wherein n=1 to 3 preferably n=1 with the proviso that there is no double bond between C-4 and C-5 or F-mono- or bicyclic heteroaryl-$(CH_2)_n$—O wherein n=1 to 3, preferably n=1 with the proviso that there is no double bond between C-4 and C-5 and wherein heteroaryl comprises 5 to 10 ring atoms wherein 1 or 2 ring atoms are hetero-atoms.

Formula I encompasses single isomers, E and Z-isomers, diastereomers, enantiomers, mixtures thereof and suitable salts thereof.

Preferably, Fluorine atom (F) is an $^{18}F$ or $^{19}F$ isotope.

Preferably, compound of general formula (I) is a compound of general formula (IA)

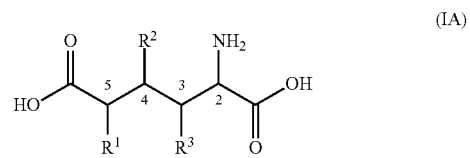

(IA)

wherein
$R^2$ and $R^3$ are Hydrogen;
$R^1$ is X,
wherein X is
Fluorine atom (F),
branched or straight-chain F—$C_1$-$C_{10}$ alkyl wherein the alkyl chain is optionally interrupted by 1 or 2 oxygen atoms with the proviso that there are at least two methylene groups between two oxygen atoms, branched or straight-chain F—$C_1$-$C_{10}$ alkoxy wherein the carbon chain is optionally interrupted by 1 additional oxygen atom with the proviso that there are at least two methylene groups between two oxygen atoms, F—$C_6$-$C_{10}$ mono- or bicyclic aryl-$(CH_2)_n$ wherein n=1 to 3, preferably n=1, F-mono- or bicyclic heteroaryl-$(CH_2)_n$ wherein n=1 to 3, preferably n=1 and heteroaryl comprises 5 to 10 ring atoms wherein 1 or 2 ring atoms are hetero-atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, F—$C_6$-$C_{10}$ mono- or bicyclic aryl-$(CH_2)_n$—O, wherein n=1 to 3 preferably n=1 or F-mono- or bicyclic heteroaryl-$(CH_2)_n$—O wherein n=1 to 3, preferably n=1 with the proviso that there is no double bond between C-4 and C-5 and wherein heteroaryl comprises 5 to 10 ring atoms wherein 1 or 2 ring atoms are hetero-atoms.

Formula IA encompasses single isomers, diastereomers, enantiomers, mixtures thereof and suitable salts thereof.

More preferably, compound of general formula (I) is a compound of general formula (IA) wherein the Fluorine atom (F) is $^{18}F$ isotope.

Even more preferably, compound of general formula (I) is a compound of general formula (IA2S) as depicted below

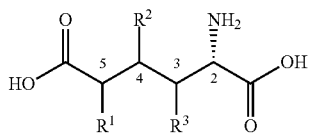 (IA2S)

wherein $R^1$, $R^2$, and R3 are described above in formula (I) or (IA) of the third embodiment.

More preferably, compound of general formula (I) is a compound of general formula (IA) wherein the Fluorine atom (F) is $^{19}F$ isotope.

Even more preferably, compound of general formula (I) is a compound of general formula (IA2S) as depicted below

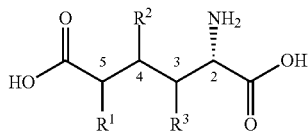 (IA2S)

wherein $R^1$, $R^2$, and $R^3$ are described above in formula (I) or (IA) of the third embodiment.

Preferably, compound of general formula (I) is a compound of general formula (IB)

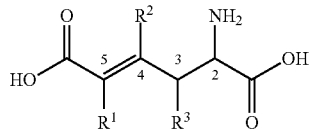 (IB)

wherein
$R^2$ and $R^3$ are Hydrogen;
$R^1$ is X,
wherein X is
branched or straight-chain F—$C_1$-$C_{10}$ alkyl wherein the alkyl chain is optionally interrupted by 1 or 2 oxygen atoms with the proviso that there are at least two methylene groups between two oxygen atoms,
F—$C_6$-$C_{10}$ mono- or bicyclic aryl-$(CH_2)_n$ wherein n=1 to 3, preferably n=1,
F-mono- or bicyclic heteroaryl-$(CH_2)_n$ wherein n=1 to 3, preferably n=1 and wherein heteroaryl comprises 5 to 10 ring atoms wherein 1 or 2 ring atoms are hetero-atoms,
F—$C_3$-$C_6$ cycloalkyl with the proviso that F is attached to one of the $CH_2$ groups of the ring,
F—$C_3$-$C_6$ cycloalkyl-$(CH_2)_n$, wherein n=1 to 3, preferably n=1, with the proviso that F is attached to one of the $CH_2$ groups of the ring.

Formula IB encompasses single isomers, E- and Z-isomers, diastereomers, enantiomers, mixtures thereof and suitable salts thereof.

More preferably, compound of general formula (I) is a compound of general formula (IB) wherein the Fluorine atom (F) is $^{18}F$ isotope.

Even more preferably, compound of general formula (I) is a compound of general formula (IB2S) as depicted below

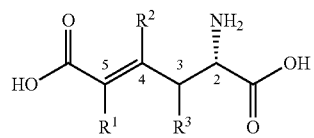 (IB2S)

wherein $R^1$, $R^2$, and $R^3$ are described above in formula (I) or (IB) of the third embodiment.

More preferably, compound of general formula (I) is a compound of general formula (IB) wherein the Fluorine atom (F) is $^{19}F$ isotope.

Even more preferably, compound of general formula (I) is a compound of general formula (IB2S) as depicted below

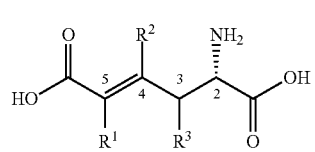 (IB2S)

wherein $R^1$, $R^2$, and $R^3$ are described above in formula (I) or (IB) of the third embodiment.

Preferably in (IA) and (IB), $R^2$ and $R^3$ are Hydrogen and $R^1$ is X.

Preferred features disclosed below apply to (IA):
Preferably X is
Fluorine atom (F),
branched or straight-chain F—$C_1$-$C_{10}$ alkyl wherein the alkyl chain is optionally interrupted by 1 or 2 oxygen atoms with the proviso that there are at least two methylene groups between two oxygen atoms,
branched or straight-chain F—$C_1$-$C_{10}$ alkoxy wherein the carbon chain is optionally interrupted by 1 additional oxygen atom with the proviso that there are at least two methylene groups between two oxygen atoms,
F—$C_6$-$C_{10}$ mono- or bicyclic aryl-$(CH_2)_n$ wherein n=1 to 3, preferably n=1 or F-mono- or bicyclic heteroaryl-$(CH_2)_n$ wherein n=1 to 3, preferably n=1, and wherein heteroaryl comprises 5 to 10 ring atoms wherein 1 or 2 ring atoms are hetero-atoms.

More preferably, X is
Fluorine atom (F),
branched or straight-chain F—$C_1$-$C_{10}$ alkyl wherein the alkyl chain is optionally interrupted by 1 or 2 oxygen atoms with the proviso that there are at least two methylene groups between two oxygen atoms,
F—$C_6$-$C_{10}$ mono- or bicyclic aryl-$(CH_2)_n$ wherein n=1 to 3, preferably n=1 or F-mono- or bicyclic heteroaryl-$(CH_2)_n$ wherein n=1 to 3, preferably n=1, and wherein heteroaryl comprises 5 to 10 ring atoms wherein 1 or 2 ring atoms are heteroatoms.

Even more preferably, X is
Fluorine atom (F),
branched or straight-chain F—$C_1$-$C_{10}$ alkyl.
Even more preferably, X is Fluorine atom (F).

Preferred features disclosed below apply to (IA) when Fluorine atom (F) is $^{19}F$ isotope:
Preferably, X is
Fluorine atom (F) with the proviso that F is not attached to a $sp^2$ hybridized carbon atom,
branched or straight-chain F—$C_1$-$C_{10}$ alkyl wherein the carbon chain is optionally interrupted by 1 or 2 oxygen atoms with the proviso that there are at least two methylene groups between two oxygen atoms, branched or straight-chain F—$C_1$-$C_{10}$ alkoxy with the proviso that X is not attached to a $sp^2$ hybridized carbon atom and wherein the carbon chain is optionally interrupted by 1 additional oxygen atom with the proviso that there are at least two methylene groups between two oxygen atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, F—$C_6$-$C_{10}$ mono- or bicyclic aryl-$(CH_2)_n$—O, wherein n=1 to 3 preferably n=1 with the proviso that X is not attached to a $sp^2$ hybridized carbon atom or F-mono- or bicyclic heteroaryl-$(CH_2)_n$—O wherein n=1 to 3, preferably n=1 with the proviso that X is not attached to a $sp^2$ hybridized carbon atom and wherein heteroaryl comprises 5 to 10 ring atoms wherein 1 or 2 ring atoms are hetero-atoms.

More preferably, X is

Fluorine atom (F) with the proviso that F is not attached to a $sp^2$ hybridized carbon atom, branched or straight-chain F—$C_1$-$C_{10}$ alkyl wherein the alkyl chain is optionally interrupted by 1 or 2 oxygen atoms with the proviso that there are at least two methylene groups between two oxygen atoms, branched or straight-chain F—$C_1$-$C_{10}$ alkoxy wherein the carbon chain is optionally interrupted by 1 additional oxygen atom with the proviso that there are at least two methylene groups between two oxygen atoms.

Even more preferably, X is

Fluorine atom (F) with the proviso that F is not attached to a $sp^2$ hybridized carbon atom, branched or straight-chain F—$C_1$-$C_{10}$ alkyl wherein the alkyl chain is optionally interrupted by 1 or 2 oxygen atoms with the proviso that there are at least two methylene groups between two oxygen atoms.

Even more preferably, X is branched or straight-chain F—$C_1$-$C_{10}$ alkyl wherein the alkyl chain is optionally interrupted by 1 or 2 oxygen atoms with the proviso that there are at least two methylene groups between two oxygen atoms.

Even more preferably, X is branched or straight-chain F—$C_1$-$C_{10}$ alkyl, preferably F—$C_1$-$C_3$ alkyl and more preferably F-propyl.

Preferred features disclosed below apply to (IA) when Fluorine atom (F) is $^{18}F$ isotope:

Preferably, X is

Fluorine atom (F) with the proviso that F is not attached to a $sp^2$ hybridized carbon atom, branched or straight-chain F—$C_1$-$C_{10}$ alkyl wherein the alkyl chain is optionally interrupted by 1 or 2 oxygen atoms with the proviso that there are at least two methylene groups between two oxygen atoms, branched or straight-chain F—$C_1$-$C_{10}$ alkoxy wherein the carbon chain is optionally interrupted by 1 additional oxygen atom with the proviso that there are at least two methylene groups between two oxygen atoms, F—$C_6$-$C_{10}$ mono- or bicyclic aryl-$(CH_2)_n$ wherein n=1 to 3, preferably n=1 or F-mono- or bicyclic heteroaryl-$(CH_2)_n$ wherein n=1 to 3, preferably n=1, and wherein heteroaryl comprises 5 to 10 ring atoms wherein 1 or 2 ring atoms are hetero-atoms.

More preferably, X is

Fluorine atom (F) with the proviso that F is not attached to a $sp^2$ hybridized carbon atom, branched or straight-chain F—$C_1$-$C_{10}$ alkyl wherein the alkyl chain is optionally interrupted by 1 or 2 oxygen atoms with the proviso that there are at least two methylene groups between two oxygen atoms, F—$C_6$-$C_{10}$ mono- or bicyclic aryl-$(CH_2)_n$ wherein n=1 to 3, preferably n=1 or F-mono- or bicyclic heteroaryl-$(CH_2)_n$ wherein n=1 to 3, preferably n=1, and wherein heteroaryl comprises 5 to 10 ring atoms wherein 1 or 2 ring atoms are heteroatoms.

More preferably, X is branched or straight-chain F—$C_1$-$C_{10}$ alkyl wherein the alkyl chain is optionally interrupted by 1 or 2 oxygen atoms with the proviso that there are at least two methylene groups between two oxygen atoms, F—$C_6$-$C_{10}$ mono- or bicyclic aryl-$(CH_2)_n$ wherein n=1 to 3, preferably n=1 or F-mono- or bicyclic heteroaryl-$(CH_2)_n$ wherein n=1 to 3, preferably n=1, and wherein heteroaryl comprises 5 to 10 ring atoms wherein 1 or 2 ring atoms are heteroatoms.

Even more preferably, X is

Fluorine atom (F) with the proviso that F is not attached to a $sp^2$ hybridized carbon atom or branched or straight-chain F—$C_1$-$C_{10}$ alkyl.

Even more preferably, X is branched or straight-chain F—$C_1$-$C_{10}$ alkyl, preferably F—$C_1$-$C_3$ alkyl and more preferably F-propyl.

Preferred features disclosed below apply to (IB):

Preferably X is branched or straight-chain F—$C_1$-$C_{10}$ alkyl wherein the alkyl chain is optionally interrupted by 1 or 2 oxygen atoms with the proviso that there are at least two methylene groups between two oxygen atoms, F—$C_6$-$C_{10}$ mono- or bicyclic aryl-$(CH_2)_n$ wherein n=1 to 3, preferably n=1 or F-mono- or bicyclic heteroaryl-$(CH_2)_n$ wherein n=1 to 3, preferably n=1 heteroaryl comprises 5 to 10 ring atoms wherein 1 or 2 ring atoms are hetero-atoms.

More preferably, X is branched or straight-chain F—$C_1$-$C_{10}$ alkyl wherein the alkyl chain is optionally interrupted by 1 or 2 oxygen atoms with the proviso that there are at least two methylene groups between two oxygen atoms.

Even more preferably, X is branched or straight-chain F—$C_1$-$C_{10}$ alkyl, more preferably, F—$C_1$-$C_3$ alkyl.

Preferred features disclosed below apply to (IB) when Fluorine atom (F) is $^{19}F$ isotope:

Preferably, X is branched or straight-chain F—$C_1$-$C_{10}$ alkyl wherein the carbon chain is optionally interrupted by 1 or 2 oxygen atoms with the proviso that there are at least two methylene groups between two oxygen atoms, F—$C_3$-$C_6$ cycloalkyl with the proviso that F is attached to one of the $CH_2$ groups of the ring, or F—$C_3$-$C_6$ cycloalkyl-$(CH_2)_n$, wherein n=1 to 3, preferably n=1, with the proviso that F is attached to one of the $CH_2$ groups of the ring.

More preferably, X is branched or straight-chain F—$C_1$-$C_{10}$ alkyl wherein the alkyl chain is optionally interrupted by 1 or 2 oxygen atoms with the proviso that there are at least two methylene groups between two oxygen atoms, Even more preferably, X is
branched or straight-chain F—$C_1$-$C_{10}$ alkyl, preferably F—$C_1$-$C_3$ alkyl. and more preferably F-propyl.

Preferred features disclosed below apply to (IB) when Fluorine atom (F) is $^{18}$F isotope:

Preferably, X is
branched or straight-chain F—$C_1$-$C_{10}$ alkyl wherein the alkyl chain is optionally interrupted by 1 or 2 oxygen atoms with the proviso that there are at least two methylene groups between two oxygen atoms, F—$C_6$-$C_{10}$ mono- or bicyclic aryl-$(CH_2)_n$ wherein n=1 to 3, preferably n=1 or F-mono- or bicyclic heteroaryl-$(CH_2)_n$ wherein n=1 to 3, preferably n=1, and wherein heteroaryl comprises 5 to 10 ring atoms wherein 1 or 2 ring atoms are hetero-atoms.

Preferably, X is
branched or straight-chain F—$C_1$-$C_{10}$ alkyl wherein the alkyl chain is optionally interrupted by 1 or 2 oxygen atoms with the proviso that there are at least two methylene groups between two oxygen atoms, F—$C_3$-$C_6$ cycloalkyl with the proviso that F is attached to one of the $CH_2$ groups of the ring or F—$C_3$-$C_6$ cycloalkyl-$(CH_2)_n$, wherein n=1 to 3, preferably n=1, with the proviso that F is attached to one of the $CH_2$ groups of the ring.

More preferably, X is
branched or straight-chain F—$C_1$-$C_{10}$ alkyl, more preferably F—$C_1$-$C_3$ alkyl and more preferably F-propyl.

Preferred features disclosed below apply to (IA) and (IB):

Preferably, branched or straight-chain F—$C_1$-$C_{10}$ alkyl is F—$C_1$-$C_6$ alkyl or F—$C_7$-$C_{10}$ alkyl. More preferably, F—$C_1$-$C_{10}$ alkyl is F—$C_1$-$C_3$ alkyl, F—$C_1$ alkyl (F—$CH_2$), F—$C_2$ alkyl (F—$(CH_2)_2$), F—$C_3$ alkyl (e.g. F—$(CH_2)_3$), F—$C_4$ alkyl (e.g. F—$(CH_2)_4$) or F—$C_5$ alkyl (e.g. F—$(CH_2)_5$).

Alkyl chain can be substituted at any position with the Fluorine atom (F). Preferably, alkyl chain is substituted with the Fluorine atom (F) at the terminal position of the chain.

Preferably, branched or straight-chain F—$C_1$-$C_{10}$ alkyl wherein the alkyl chain is optionally interrupted by 1 or 2 oxygen atoms with the proviso that there are at least two methylene groups between two oxygen atoms is (2-fluoroethoxy)methyl, 2-(2-fluoroethoxy)ethyl, 3-(2-fluoroethoxy)propyl, [2-(2-fluoroethoxy)ethoxy]methyl, 3-(fluoromethoxy)propyl, 2-[2-(2-fluoroethoxy)ethoxy]ethyl.

Preferably, branched or straight-chain F—$C_1$-$C_{10}$ alkoxy is F—$C_2$-$C_6$ alkoxy or F—$C_7$-$C_{10}$ alkoxy. More preferably, F—$C_2$-$C_{10}$ alkoxy is F—$C_2$ alkoxy (F—$(CH_2)_2O$), F—$C_3$ alkoxy (e.g. F—$(CH_2)_3O$), F—$C_4$ alkoxy (e.g., F—$(CH_2)_4O$) or F—$C_5$ alkoxy (e.g. F—$(CH_2)_5O$).

The alkoxy chain can be substituted at any carbon atom with the Fluorine atom (F).

Preferably, alkoxy chain is substituted with the Fluorine atom (F) at the terminal position of the chain.

Preferably, branched or straight-chain F—$C_1$-$C_{10}$ alkoxy wherein the carbon chain is optionally interrupted by 1 additional oxygen atom with the proviso that there are at least two methylene groups between two oxygen atoms is fluoromethoxy, 2-fluoroethoxy, 3-fluoropropoxy, 2-(2-fluoroethoxy)ethoxy, 3-(fluoromethoxy)propan-1-oxy, 3-(2-fluoroethoxy)propan-1-oxy.

Preferably, F—$C_6$-$C_{10}$ mono- or bicyclic aryl-$(CH_2)_n$ is F—$C_6H_4$—$(CH_2)_n$ wherein n=1 to 3, preferably n=1. Aryl can be substituted at any position with the Fluorine atom (F). The mono- or bicyclic aryl residue can optionally be substituted by electron withdrawing groups like $CF_3$, CN and the like.

Preferably, F—$C_6$-$C_{10}$ mono- or bicyclic aryl-$(CH_2)_n$ is F—$C_6$aryl-$(CH_2)_n$ wherein n=1 to 3, preferably n=1. Aryl is substituted at any position with the Fluorine atom (F). Aryl is optionally substituted.

Preferably, F-mono- or bicyclic heteroaryl-$(CH_2)_n$ is F-pyridinyl-$(CH_2)_n$ or F-pyrimidinyl-$(CH_2)_n$ wherein n=1 to 3, preferably n=1. Heteroaryl can be substituted at any carbon atom with the Fluorine atom (F). Heteroaryl is optionally substituted.

Preferably, F—$C_3$-$C_6$ cycloalkyl is F—$C_3$ cycloalkyl, F—$C_4$ cycloalkyl, F—$C_5$ cycloalkyl or F—$C_6$ cycloalkyl. Cycloalkyl can be substituted at any position with the Fluorine atom (F).

Preferably, F—$C_3$-$C_6$ cycloalkyl-$(CH_2)_n$ is F—cyclopropyl-$(CH_2)_n$, F—cyclobutyl-$(CH_2)_n$, cyclopentyl-$(CH_2)_n$ or F—cyclohexyl-$(CH_2)_n$ wherein n=1 to 3, preferably n=1. Cycloalkyl can be substituted at any position with the Fluorine atom (F).

Preferably, F—$C_6$-$C_{10}$ mono- or bicyclic aryl-$(CH_2)_n$—O is F—$C_6H_4$—$(CH_2)_n$—O wherein n=1 to 3 preferably n=1. Aryl can be substituted at any position with the Fluorine atom (F).

Preferably, X is 4-cyano-3-fluorobenzyl.

Preferably, F-mono- or bicyclic heteroaryl-$(CH_2)_n$—O is F-pyridinyl-$(CH_2)_n$—O or F-pyrimidinyl-$(CH_2)_n$—O wherein n=1 to 3, preferably n=1. Heteroaryl can be substituted at any carbon atom with the Fluorine atom (F).

Embodiments and preferred features can be combined together and are within the scope of the invention.

Invention compounds are selected from but not limited to

Ammonium hydrogen
(2S)-2-amino-5-(3-fluoropropyl)hexanedioate

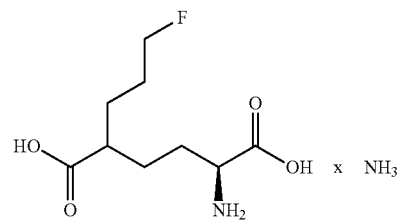

(2S)-2-Amino-5-(3-[$^{18}$F]fluoropropyl)hexanedioic acid

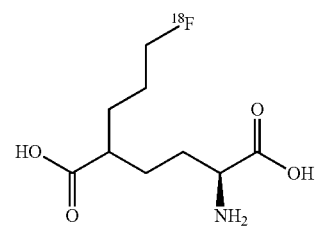 [SMILES: N[C@@H](CCC(CCC[18F])C(=O)O)C(=O)O]

13

(2S)-2-Amino-5-fluorohexanedioic acid

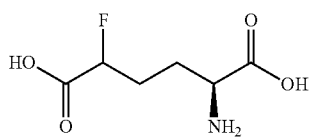 [SMILES: N[C@@H](CCC(F)C(=O)O)C(=O)O]

(2S)-2-Amino-5-[¹⁸F]fluorohexanedioic acid

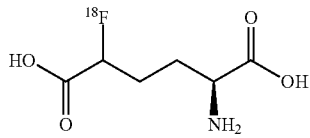

(E)-(S)-5-Amino-2-(3-fluoropropyl)hex-2-enedioic acid

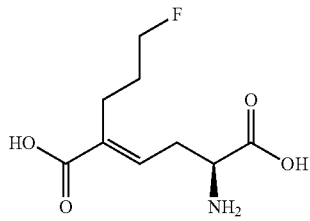

(E)-(S)-5-Amino-2-(3-[¹⁸F]fluoropropyl)hex-2-enedioic acid

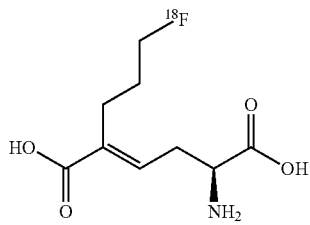

(Z)—(S)-5-Amino-2-(3-fluoropropyl)hex-2-enedioic acid-trifluoroacetate

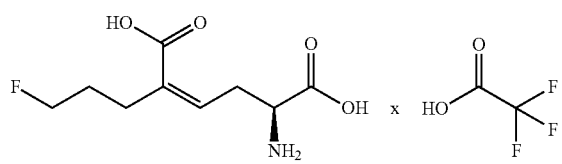

14

(Z)—(S)-5-Amino-2-(3-[¹⁸F]fluoropropyl)hex-2-enedioic acid

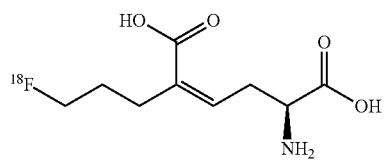 [SMILES: N[C@@H](C/C=C(/CCC[18F])C(=O)O)C(=O)O]

(2S)-2-Amino-5-(4-cyano-3-fluorobenzyl)hexanedioic acid

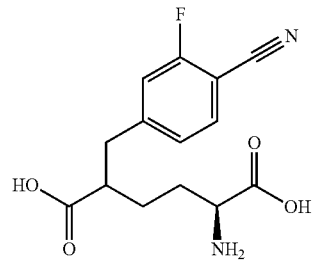 [SMILES: N#Cc1ccc(CC(CC[C@H](N)C(=O)O)C(=O)O)cc1F]

(2S)-2-Amino-5-(4-cyano-3-[¹⁸F]fluorobenzyl)hexanedioic acid

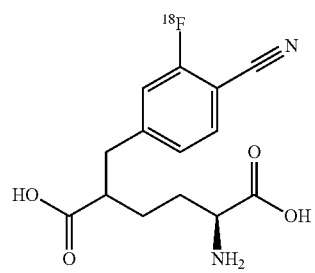 [SMILES: N#Cc1ccc(CC(CC[C@H](N)C(=O)O)C(=O)O)cc1[18F]]

In a second aspect, the invention is directed to compounds of the general formula (II)

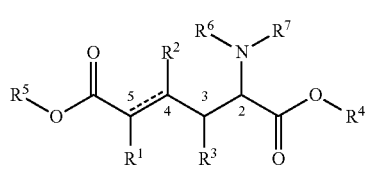

(II)

wherein
R¹, R² and R³ are independently from each other selected from Hydrogen and X with the proviso that one of R¹, R² and R³ is X,
wherein X is
Fluorine atom (F) with the proviso that F is not attached to a sp² hybridized carbon atom,
branched or straight-chain F—C₁-C₁₀ alkyl wherein the carbon chain is optionally interrupted by 1 or 2 oxygen atoms with the proviso that there are at least two methylene groups between two oxygen atoms, branched or straight-chain F—$C_1$-$C_{10}$ alkoxy with the proviso that F is not attached to a $sp^2$ hybridized carbon atom and wherein the carbon chain is optionally interrupted by 1 additional oxygen atom with the proviso that there are at least two methylene groups between two oxygen atoms, F—$C_6$-$C_{10}$ mono- or bicyclic aryl-$(CH_2)_n$ wherein n=1 to 3, preferably n=1, F-mono- or bicyclic heteroaryl-$(CH_2)_n$ wherein n=1 to 3, preferably n=1 and wherein heteroaryl comprises 5 to 10 ring atoms wherein 1 or 2 atom are hetero-atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, F—$C_6$-$C_{10}$ mono- or bicyclic aryl-$(CH_2)_n$—O, wherein n=1 to 3 preferably n=1 with the proviso that X is not attached to a $sp^2$ hybridized carbon atom or F-mono- or bicyclic heteroaryl-$(CH_2)_n$—O wherein n=1 to 3, preferably n=1 with the proviso that X is not attached to a $sp^2$ hybridized carbon atom and wherein heteroaryl comprises 5 to 10 ring atoms wherein 1 or 2 ring atoms are hetero-atoms;

$R^4$=Hydrogen or O-protecting group;

$R^5$=Hydrogen or O-protecting group;

$R^6$=Hydrogen or N-protecting group;

$R^7$=Hydrogen or N-protecting group;

or the group $NR^6R^7$ is a 1,3-dioxo-1,3-dihydro-2H-isoindol-2-yl (phthalimido) or an azido group;

with the proviso, that at least one of the substituents $R^4$, $R^5$, $R^6$, or $R^7$ is not Hydrogen.

Formula II encompasses single isomers, E and Z-isomers, diastereomers, enantiomers, mixtures thereof and suitable salts thereof.

Preferably, when Fluorine atom (F) is $^{19}$F isotope then compound of formula II is never 6-Ethyl,-1-methyl (2S)-2-[(tert-butoxycarbonyl)amino]-5-fluorohexanedioate.

In a first embodiment, the invention is directed to a compound of general formula (II) wherein the Fluorine atom (F) is $^{18}$F isotope.

$R^1$, $R^2$, $R^3$, $R^4$, $R^5$, $R^6$, $R^7$ and X are as described above.

Preferably, $R^2$ and $R^3$ are Hydrogen; and $R^1$ is X.

More preferably, compounds of general formula (II) encompassing the first embodiment are compounds of general formula (II2S).

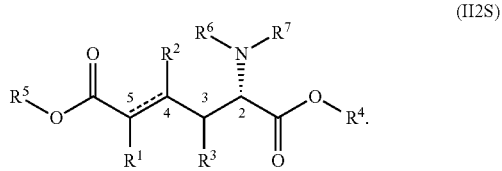

(II2S)

In a second embodiment, the invention is directed to a compound of general formula (II) wherein the Fluorine atom (F) is $^{19}$F isotope and with the proviso that the compound of formula (II2S) is not 6-Ethyl-1-methyl-(2S)-2-[(tert-butoxycarbonyl)amino]-5-fluorohexanedioate.

$R^1$, $R^2$, $R^3$, $R^4$, $R^5$, $R^6$, $R^7$ and X are as described above.

Preferably, $R^2$ and $R^3$ are Hydrogen; and $R^1$ is X.

Preferably, X is

Fluorine atom (F) with the proviso that F is not attached to a $sp^2$ hybridized carbon atom, branched or straight-chain F—$C_1$-$C_{10}$ alkyl wherein the carbon chain is optionally interrupted by 1 or 2 oxygen atoms with the proviso that there are at least two methylene groups between two oxygen atoms, branched or straight-chain F—$C_1$-$C_{10}$ alkoxy with the proviso that F is not attached to a $sp^2$ hybridized carbon atom and wherein the carbon chain is optionally interrupted by 1 additional oxygen atom with the proviso that there are at least two methylene groups between two oxygen atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, F—$C_6$-$C_{10}$ mono- or bicyclic aryl-$(CH_2)_n$—O, wherein n=1 to 3 preferably n=1 with the proviso that X is not attached to a $sp^2$ hybridized carbon atom or F-mono- or bicyclic heteroaryl-$(CH_2)_n$—O wherein n=1 to 3, preferably n=1 with the proviso that X is not attached to a $sp^2$ hybridized carbon atom and wherein heteroaryl comprises 5 to 10 ring atoms wherein 1 or 2 ring atoms are hetero-atoms.

More preferably, compounds of general formula (II) encompassing the second embodiment are compound of general formula (II2S).

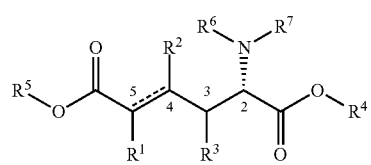

(II2S)

with the proviso that the compound of formula (II2S) is not 6-Ethyl-1-methyl-(2S)-2-[(tert-butoxycarbonyl)amino]-5-fluorohexanedioate.

In a third embodiment, the invention is directed to a compound of general formula (II)

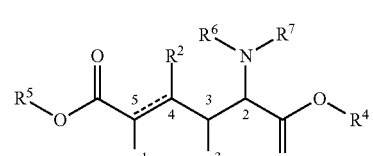

(II)

wherein
$R^2$ and $R^3$ are Hydrogen;
$R^1$ is X,
wherein X is
Fluorine atom (F) with the proviso that there is no double bond between C-4 and C-5, branched or straight-chain F—$C_1$-$C_{10}$ alkyl wherein the carbon chain is optionally interrupted by 1 or 2 oxygen atoms with the proviso that there are at least two methylene groups between two oxygen atoms, branched or straight-chain F—$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms, F—$C_6$-$C_{10}$ mono- or bicyclic aryl-$(CH_2)_n$ wherein n=1 to 3, preferably n=1, F-mono- or bicyclic heteroaryl-$(CH_2)_n$ wherein n=1 to 3, preferably n=1 and wherein heteroaryl comprises 5 to 10 ring atoms wherein 1 or 2 ring atoms are hetero-atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, F—$C_6$-$C_{10}$ mono- or bicyclic aryl-$(CH_2)_n$—O, wherein n=1 to 3 preferably n=1 with the proviso that there is no double bond between C-4 and C-5 or F-mono- or bicyclic heteroaryl-$(CH_2)_n$—O wherein n=1 to 3, preferably n=1 with the proviso that there is no double bond between C-4 and C-5 and that heteroaryl comprises 5 to 10 ring atoms wherein 1 or 2 ring atoms are hetero-atoms;

$R^4$=Hydrogen or O-protecting group;
$R^5$=Hydrogen or O-protecting group;
$R^6$=Hydrogen or N-protecting group;
$R^7$=Hydrogen or N-protecting group;
or the group $NR^6R^7$ is a 1,3-dioxo-1,3-dihydro-2H-isoindol-2-yl (phthalimido) or an azido group;
with the proviso, that at least one of the substituents $R^4$, $R^5$, $R^6$, or $R^7$ is not Hydrogen.

Formula II encompasses single isomers, E and Z-isomers, diastereomers, enantiomers, mixtures thereof and suitable salts thereof.

Preferably, when Fluorine atom (F) is $^{19}$F isotope then compound of formula II is never 6-Ethyl-1-methyl-(2S)-2-[(tert-butoxycarbonyl)amino]-5-fluorohexanedioate.

Preferably, compound of general formula (II) is a compound of general formula (IIA)

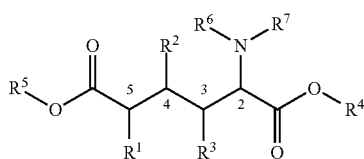

(IIA)

$R^2$ and $R^3$ are Hydrogen;
$R^1$ is X,
wherein X is
Fluorine atom (F), branched or straight-chain F—$C_1$-$C_{10}$ alkyl wherein the carbon chain is optionally interrupted by 1 or 2 oxygen atoms with the proviso that there are at least two methylene groups between two oxygen atoms, branched or straight-chain F—$C_1$-$C_{10}$ alkoxy and wherein the carbon chain is optionally interrupted by 1 additional oxygen atom with the proviso that there are at least two methylene groups between two oxygen atoms, F—$C_6$-$C_{10}$ mono- or bicyclic aryl-$(CH_2)_n$ wherein n=1 to 3, preferably n=1, F-mono- or bicyclic heteroaryl-$(CH_2)_n$ wherein n=1 to 3, preferably n=1 and wherein heteroaryl comprises 5 to 10 ring atoms wherein 1 or 2 ring atoms are hetero-atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, F—$C_6$-$C_{10}$ mono- or bicyclic aryl-$(CH_2)_n$—O, wherein n=1 to 3 preferably n=1 or F-mono- or bicyclic heteroaryl-$(CH_2)_n$—O wherein n=1 to 3, preferably n=1 heteroaryl comprises 5 to 10 ring atoms wherein 1 or 2 ring atoms are hetero-atoms;

$R^4$=Hydrogen or O-protecting group;
$R^5$=Hydrogen or O-protecting group;
$R^6$=Hydrogen or N-protecting group;
$R^7$=Hydrogen or N-protecting group;
or the group $NR^6R^7$ is a 1,3-dioxo-1,3-dihydro-2H-isoindol-2-yl (phthalimido) or an azido group;
with the proviso, that at least one of the substituents $R^4$, $R^5$, $R^6$, or $R^7$ is not Hydrogen.

Formula IIA encompasses single isomers, diastereomers, enantiomers, mixtures thereof and suitable salts thereof.

Preferably, when Fluorine atom (F) is $^{19}$F isotope then compound of formula IIA is never 6-Ethyl 1-methyl (2S)-2-[(tert-butoxycarbonyl)amino]-5-fluorohexanedioate.

More preferably, compound of general formula (II) is a compound of general formula (IIA) wherein the Fluorine atom (F) is $^{18}$F isotope Even more preferably, compound of general formula (II) is a compound of general formula (IIA2S) as depicted below

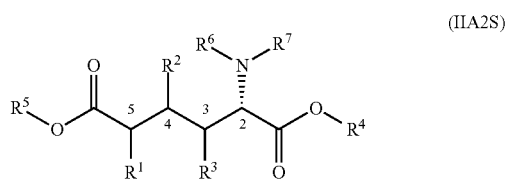

(IIA2S)

wherein $R^1$, $R^2$, $R^3$, $R^4$, $R^5$, $R^6$, and $R^7$ are described above in formula (II) or (IIA) of the third embodiment.

More preferably, compound of general formula (II) is a compound of general formula (IIA) wherein the Fluorine atom (F) is $^{19}$F isotope and with the proviso that the compound of formula (IIA) is not 6-Ethyl-1-methyl-(2S)-2-[(tert-butoxycarbonyl)amino]-5-fluorohexanedioate.

Even more preferably, compound of general formula (II) is a compound of general formula (IIA2S) as depicted below

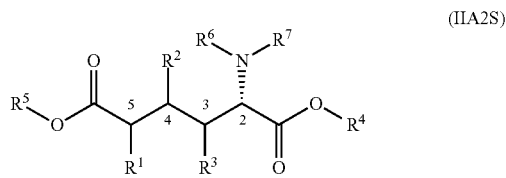

(IIA2S)

wherein $R^1$, $R^2$, $R^3$, $R^4$, $R^5$, $R^6$, and $R^7$ are described above in formula (II) or (IIA) of the third embodiment.

Preferably, compound of general formula (II) is a compound of general formula (IIB)

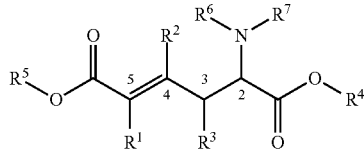
(IIB)

wherein $R^2$ and $R^3$ are Hydrogen;

$R^1$ is X, wherein X is branched or straight-chain F—$C_1$-$C_{10}$ alkyl wherein the carbon chain is optionally interrupted by 1 or 2 oxygen atoms with the proviso that there are at least two methylene groups between two oxygen atoms, F—$C_6$-$C_{10}$ mono- or bicyclic aryl-$(CH_2)_n$ wherein n=1 to 3, preferably n=1, F-mono- or bicyclic heteroaryl-$(CH_2)_n$ wherein n=1 to 3, preferably n=1 and wherein heteroaryl comprises 5 to 10 ring atoms wherein 1 or 2 ring atoms are hetero-atoms, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, preferably n=1, with the proviso that F is attached to one of the $CH_2$ groups of the ring, $R^4$=Hydrogen or O-protecting group;

$R^5$=Hydrogen or O-protecting group;

$R^6$=Hydrogen or N-protecting group;

$R^7$=Hydrogen or N-protecting group;

or the group $NR^6R^7$ is a 1,3-dioxo-1,3-dihydro-2H-isoindol-2-yl (phthalimido) or an azido group;

with the proviso, that at least one of the substituents $R^4$, $R^5$, $R^6$, or $R^7$ is not Hydrogen.

Formula IIB encompasses single isomers, E and Z-isomers, diastereomers, enantiomers, mixtures thereof and suitable salts thereof.

More preferably, compound of general formula (II) is a compound of general formula (IIB) wherein the Fluorine atom (F) is $^{18}F$ isotope.

Even more preferably, compound of general formula (II) is a compound of general formula (IIB2S) as depicted below

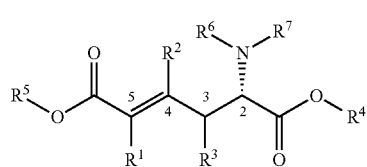
(IIB2S)

wherein $R^1$, $R^2$, $R^3$, $R^4$, $R^5$, $R^6$, and $R^7$ are described above in formula (II) or (IIB) of the third embodiment.

More preferably, compound of general formula (II) is a compound of general formula (IIB) wherein the Fluorine atom (F) is $^{19}F$ isotope.

Even more preferably, compound of general formula (II) is a compound of general formula (IIB2S) as depicted below

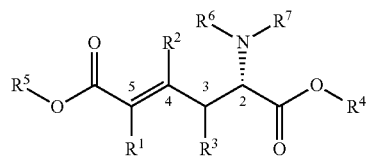
(IIB2S)

wherein $R^1$, $R^2$, $R^3$, $R^4$, $R^5$, $R^6$, and $R^7$ are described above in formula (II) or (IIB) of the third embodiment.

The compounds of formula II are Fluoro-labeled compounds wherein the functional group(s) such as OH and $NH_2$ are protected with suitable protecting group(s) defined as $R^4$ to $R^7$, respectively.

The preferred features $R^1$ to $R^3$ disclosed for compound of general formula (II) are incorporated herein.

$R^4$ and $R^5$ are O-protecting groups selected from the group comprising

Methyl, Ethyl, Propyl, Butyl, t-Butyl, Allyl, Benzyl, 4-Methoxybenzyl, 4-Methoxyphenyl. Preferably, $R^4$ is an O-protecting group selected from the group comprising Methyl, Ethyl, t-Butyl, Benzyl.

N-protecting groups are selected from the group comprising

Carbobenzyloxy (Cbz), p-Methoxybenzyl carbonyl (Moz or MeOZ), tert-Butyloxycarbonyl (BOC), 9-Fluorenylmethyloxycarbonyl (FMOC), Benzyl (Bn), p-Methoxybenzyl (PMB), 3,4-Dimethoxybenzyl (DMPM), Triphenylmethyl and p-methoxyphenyl (PMP) or the group $NR^6R^7$ is a 1,3-dioxo-1,3-dihydro-2H-isoindol-2-yl (phthalimido) or an azido group.

Preferably, $R^6$ and $R^7$ are selected independently from each other from the group comprising Carbobenzyloxy (Cbz), p-Methoxybenzyl carbonyl (Moz or MeOZ), tert-Butyloxycarbonyl (BOC), 9-Fluorenylmethyloxycarbonyl (FMOC), Benzyl (Bn).

More preferably, $R^6$ and $R^7$ are selected independently from each other from the group comprising tert-Butyloxycarbonyl (BOC) and 9-Fluorenylmethyloxycarbonyl (FMOC).

Even more preferably, $R^6$ is an N-protecting group and $R^7$ is Hydrogen or an N-protecting group.

The preferred feature X disclosed for compound of general formula (I) is herein incorporated.

Invention compounds are selected from but not limited to 6-tert-Butyl 1-ethyl (Z)—(S)-5-[(tert-butoxycarbonyl)amino]-2-(3-fluoropropyl)hex-2-enedioate 6-tert-Butyl 1-ethyl (E)-(S)-5-[(tert-butoxycarbonyl)amino]-2-(3-fluoropropyl)hex-2-enedioate

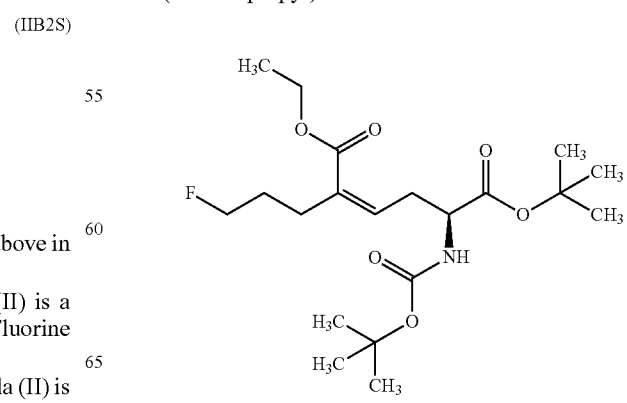

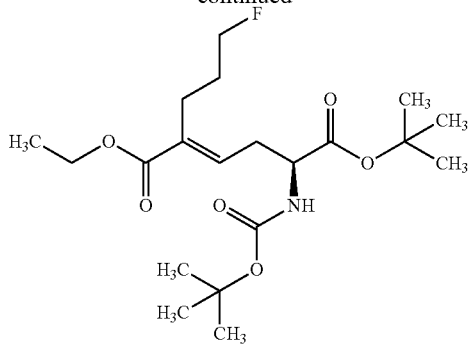

1-tert-Butyl 6-ethyl (2S)-2-[(tert-butoxycarbonyl)amino]-5-(3-fluoropropyl)hexanedioate

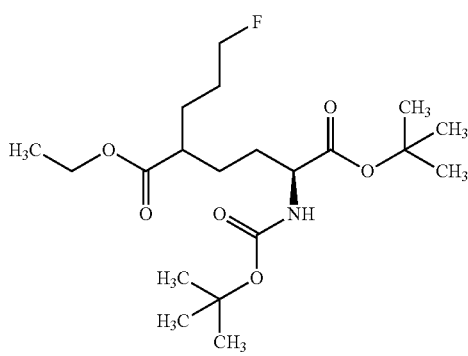 [SMILES: CCOC(=O)C(CCCF)CC[C@H](NC(=O)OC(C)(C)C)C(=O)OC(C)(C)C]

1-tert-Butyl 6-hydrogen (2S)-2-[(tert-butoxycarbonyl)amino]-5-(3-fluoropropyl)hexanedioate

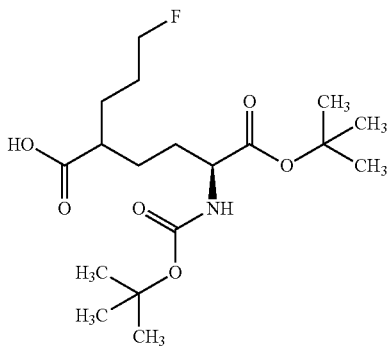 [SMILES: CC(C)(C)OC(=O)N[C@@H](CCC(CCCF)C(=O)O)C(=O)OC(C)(C)C]

(Z)—(S)-5-[(tert-Butoxycarbonyl)amino]-2-(3-fluoropropyl)hex-2-enedioic acid

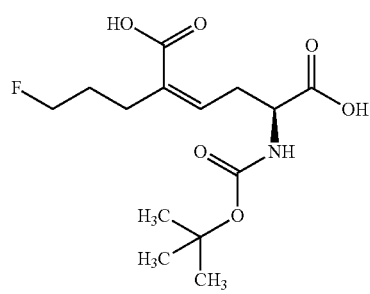

wherein the Fluorine atom (F) is an $^{18}F$ or $^{19}F$ isotope.

Di-tert-butyl (2S)-2-[(tert-butoxycarbonyl)amino]-5-(4-cyano-3-fluorobenzyl)hexanedioate

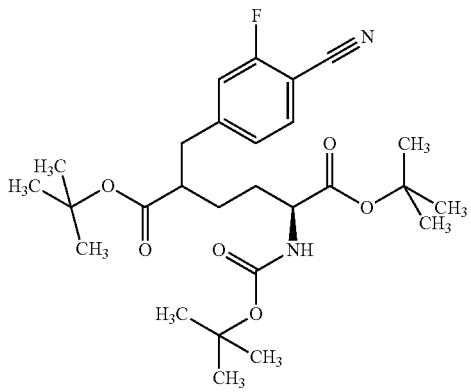 [SMILES: CC(C)(C)OC(=O)N[C@@H](CCC(Cc1ccc(C#N)c(F)c1)C(=O)OC(C)(C)C)C(=O)OC(C)(C)C]

In a third aspect, the invention is directed to compounds of the general formula (III)

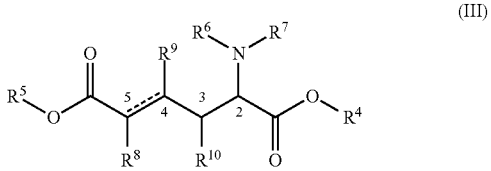

(III)

wherein $R^8$, $R^9$ and $R^{10}$ are independently from each other selected from Hydrogen and Y with the proviso that one of $R^8$, $R^9$ and $R^{10}$ is Y, wherein Y is Leaving Group (LG) with the proviso that Y is not attached to a $sp^2$ hybridized carbon atom, branched or straight-chain LG-$C_1$-$C_{10}$ alkyl wherein the carbon chain is optionally interrupted by 1 or 2 oxygen atoms with the proviso that there are at least two methylene groups between two oxygen atoms, branched or straight-chain LG-$C_1$-$C_{10}$ alkoxy with the proviso that Y is not attached to a $sp^2$ hybridized carbon atom and wherein the carbon chain is optionally interrupted by 1 additional oxygen atom with the proviso that there are at least two methylene groups between two oxygen atoms, LG-$C_6$-$C_{10}$ mono- or bicyclic aryl-$(CH_2)_n$ wherein n=1 to 3, preferably n=1, LG-mono- or bicyclic heteroaryl-$(CH_2)_n$ wherein n=1 to 3, preferably n=1, and wherein heteroaryl comprises 5 to 10 ring atoms wherein 1 or 2 ring atoms are hetero-atoms, LG-$C_3$-$C_6$ cycloalkyl with the proviso that LG is attached to one of the $CH_2$ groups of the ring, LG-$C_3$-$C_6$ cycloalkyl-$(CH_2)_n$, wherein n=1 to 3, preferably n=1, with the proviso that LG is attached to one of the $CH_2$ groups of the ring, LG-$C_6$-$C_{10}$ mono- or bicyclic aryl-$(CH_2)_n$—O, wherein n=1 to 3 preferably n=1 with the proviso that Y is not attached to a $sp^2$ hybridized carbon atom or LG-mono- or bicyclic heteroaryl-$(CH_2)_n$—O wherein n=1 to 3, preferably n=1 with the proviso that Y is not attached to a $sp^2$ hybridized carbon atom and wherein heteroaryl comprises 5 to 10 ring atoms wherein 1 or 2 ring atoms are hetero-atoms;

$R^4$=O-protecting group;

$R^5$=O-protecting group;

$R^6$=N-protecting group;

$R^7$=Hydrogen or N-protecting group or the group $NR^6R^7$ is a 1,3-dioxo-1,3-dihydro-2H-isoindol-2-yl (phthalimido) or an azido group.

Formula III encompasses single isomers, E and Z-isomers, diastereomers, enantiomers, mixtures thereof suitable salts thereof.

Preferably, compound of general formula (III) is never 1-Benzyl-6-methyl-(2S)-2-[(tert-butoxycarbonyl)amino]-5-(2-thioxopyridin-1(2H)-yl)hexanedioate.

Preferably, compound of general formula (III) is a compound of general formula (III2S)

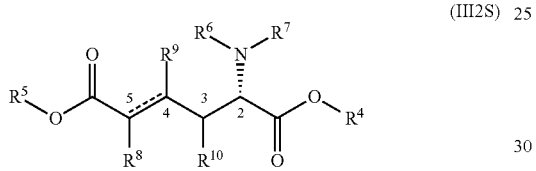

(III2S)

wherein $R^5$, $R^8$, $R^9$, $R^{10}$, $R^6$, $R^7$ and $R^4$ are described above in formula (III).

More preferably, compound of general formula (III) is a compound of general formula (III2S) with the proviso that compound of general formula (III2S) is never 1-Benzyl-6-methyl-(2S)-2-[(tert-butoxycarbonyl)amino]-5-(2-thioxopyridin-1(2H)-yl)hexanedioate.

In a first embodiment, the invention is directed to a compound of general formula (III)

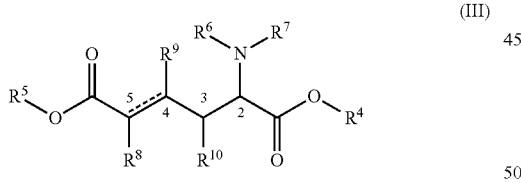

(III)

wherein $R^9$ and $R^{10}$ are Hydrogen;

$R^8$ is Y, wherein Y is

Leaving Group (LG) with the proviso that there is no double bond between C-4 and C-5, branched or straight-chain LG-$C_1$-$C_{10}$ alkyl wherein the carbon chain is optionally interrupted by 1 or 2 oxygen atoms with the proviso that there are at least two methylene groups between two oxygen atoms, branched or straight-chain LG-$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms, LG-$C_6$-$C_{10}$ mono- or bicyclic aryl-$(CH_2)_n$ wherein n=1 to 3, preferably n=1, LG-mono- or bicyclic heteroaryl-$(CH_2)_n$ wherein n=1 to 3, preferably n=1 and wherein heteroaryl comprises 5 to 10 ring atoms wherein 1 or 2 ring atoms are hetero-atoms, LG-$C_3$-$C_6$ cycloalkyl with the proviso that LG is attached to one of the $CH_2$ groups of the ring, LG-$C_3$-$C_6$ cycloalkyl-$(CH_2)_n$, wherein n=1 to 3, preferably n=1, with the proviso that LG is attached to one of the $CH_2$ groups of the ring, LG-$C_6$-$C_{10}$ mono- or bicyclic aryl-$(CH_2)_n$—O, wherein n=1 to 3 preferably n=1 with the proviso that there is no double bond between C-4 and C-5 or LG-mono- or bicyclic heteroaryl-$(CH_2)_n$—O wherein n=1 to 3, preferably n=1 with the proviso that there is no double bond between C-4 and C-5 and wherein heteroaryl comprises 5 to 10 ring atoms wherein 1 or 2 ring atoms are hetero-atoms;

$R^4$=O-protecting group;

$R^5$=O-protecting group;

$R^6$=N-protecting group;

$R^7$=Hydrogen or N-protecting group or the group $NR^6R^7$ is a 1,3-dioxo-1,3-dihydro-2H-isoindol-2-yl (phthalimido) or an azido group.

Formula III encompasses single isomers, E and Z-isomers, diastereomers, enantiomers, mixtures thereof and suitable salts thereof.

Preferably, compound of general formula (III) is never 1-Benzyl-6-methyl-(2S)-2-[(tert-butoxycarbonyl)amino]-5-(2-thioxopyridin-1(2H)-yl)hexanedioate.

Preferably, compound of general formula (III) is a compound of general formula (III2S)

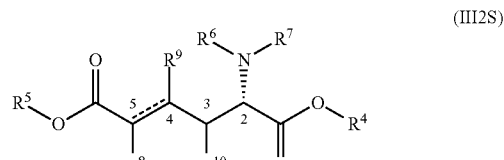

(III2S)

wherein $R^5$, $R^8$, $R^9$, $R^{10}$, $R^6$, $R^7$ and $R^4$ are described above in formula (III).

More preferably, compound of general formula (III) is a compound of general formula (III2S) with the proviso that compound of general formula (III2S) is never 1-Benzyl-6-methyl-(2S)-2-[(tert-butoxycarbonyl)amino]-5-(2-thioxopyridin-1(2H)-yl)hexanedioate.

Preferably, compound of general formula (III) is a compound of general formula (IIIA)

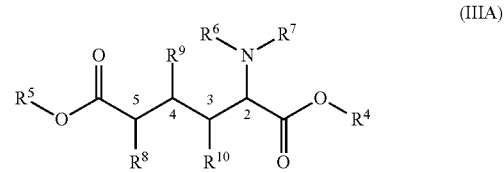

(IIIA)

wherein $R^9$ and $R^{10}$ are Hydrogen, $R^8$ is Y, wherein Y is

Leaving Group (LG), branched or straight-chain LG-$C_1$-$C_{10}$ alkyl wherein the carbon chain is optionally interrupted by 1 or 2 oxygen atoms with the proviso that there are at least two methylene groups between two oxygen atoms, branched or straight-chain LG-$C_1$-$C_{10}$ alkoxy wherein the carbon chain is optionally interrupted by 1 additional oxygen atom with the proviso that there are at least two methylene groups between two oxygen atoms, branched or straight-chain LG-$C_1$-$C_{10}$ alkoxy LG-$C_6$-$C_{10}$ mono- or bicyclic aryl-$(CH_2)_n$ wherein n=1 to 3, preferably n=1, LG-mono- or bicyclic heteroaryl-$(CH_2)_n$ wherein n=1 to 3, preferably n=1 and wherein heteroaryl comprises 5 to 10 ring atoms wherein 1 or 2 ring atoms are heteroatoms, LG-$C_3$-$C_6$ cycloalkyl with the proviso that LG is attached to one of the $CH_2$ groups of the ring, LG-$C_3$-$C_6$ cycloalkyl-$(CH_2)_n$, wherein n=1 to 3, preferably n=1, with the proviso that LG is attached to one of the $CH_2$ groups of the ring, LG-$C_6$-$C_{10}$ mono- or bicyclic aryl-$(CH_2)_n$—O, wherein n=1 to 3 preferably n=1 or LG-mono- or bicyclic heteroaryl-$(CH_2)_n$—O wherein n=1 to 3, preferably n=1 and wherein heteroaryl comprises 5 to 10 ring atoms wherein 1 or 2 ring atoms are heteroatoms;

$R^4$=O-protecting group;

$R^5$=O-protecting group;

$R^6$=N-protecting group;

$R^7$=Hydrogen or N-protecting group;

or the group $NR^6R^7$ is a 1,3-dioxo-1,3-dihydro-2H-isoindol-2-yl (phthalimido) or an azido group.

Formula IIIA encompasses single isomers, diastereomers, enantiomers, mixtures thereof and suitable salts thereof.

More preferably, compound of general formula (IIIA) is compound of general formula (IIIA2S)

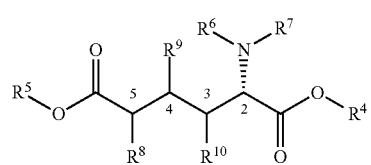

(IIIA2S)

wherein $R^5$, $R^8$, $R^9$, $R^{10}$, $R^6$, $R^7$ and $R^4$ are described above in formula (IIIA).

Even more preferably, compound of general formula (III2AS) is never 1-Benzyl-6-methyl-(2S)-2-[(tert-butoxycarbonyl)amino]-5-(2-thioxopyridin-1(2H)-yl)hexanedioate.

Preferably, compound of general formula (III) is a compound of general formula (IIIB)

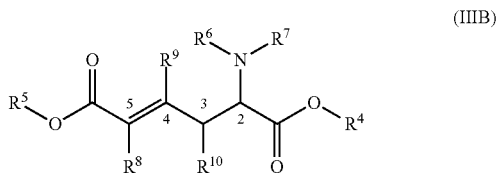

(IIIB)

wherein $R^9$ and $R^{10}$ are Hydrogen, $R^8$ is Y, wherein Y is branched or straight-chain LG-$C_1$-$C_{10}$ alkyl wherein the carbon chain is optionally interrupted by 1 or 2 oxygen atoms with the proviso that there are at least two methylene groups between two oxygen atoms, LG-$C_6$-$C_{10}$ mono- or bicyclic aryl-$(CH_2)_n$ wherein n=1 to 3, preferably n=1, LG-mono- or bicyclic heteroaryl-$(CH_2)_n$ wherein n=1 to 3, preferably n=1 and wherein heteroaryl comprises 5 to 10 ring atoms wherein 1 or 2 atom are hetero-atoms, LG-$C_3$-$C_6$ cycloalkyl with the proviso that LG is attached to one of the $CH_2$ groups of the ring, LG-$C_3$-$C_6$ cycloalkyl-$(CH_2)_n$, wherein n=1 to 3, preferably n=1, with the proviso that LG is attached to one of the $CH_2$ groups of the ring;

$R^4$=O-protecting group;

$R^5$=O-protecting group;

$R^6$=N-protecting group;

$R^7$=Hydrogen or N-protecting group;

or the group $NR^6R^7$ is a 1,3-dioxo-1,3-dihydro-2H-isoindol-2-yl (phthalimido) or an azido group.

Formula IIIB encompasses single isomers, E and Z-isomers, diastereomers, enantiomers, mixtures thereof and suitable salts thereof.

More preferably, compound of general formula (IIIB) is compound of general formula (IIIB2S)

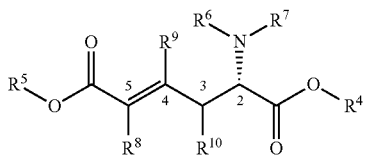

(IIIB2S)

wherein $R^5$, $R^8$, $R^9$, $R^{10}$, $R^6$, $R^7$ and $R^4$ are described above in formula (IIIB).

The compounds of formula III, (IIIA) or (IIIB) are compounds suitable for fluorolabeling wherein the functional group(s) such as OH and $NH_2$ are protected with suitable protecting group(s) such as $R^4$ to $R^7$, respectively.

Preferably, $R^9$ and $R^{10}$ are Hydrogen and $R^8$ is Y,

Preferably in (IIIA) and (IIIB), $R^9$ and $R^{10}$ are Hydrogen and $R^8$ is Y.

Preferred features disclosed below apply to (IIIA):

Preferably Y is

Leaving Group (LG), branched or straight-chain LG-$C_1$-$C_{10}$ alkyl wherein the alkyl chain is optionally interrupted by 1 or 2 oxygen atoms with the proviso that there are at least two methylene groups between two oxygen atoms, branched or straight-chain LG-$C_1$-$C_{10}$ alkoxy wherein the carbon chain is optionally interrupted by 1 additional oxygen atom with the proviso that there are at least two methylene groups between two oxygen atoms, LG-$C_6$-$C_{10}$ mono- or bicyclic aryl-$(CH_2)_n$ wherein n=1 to 3, preferably n=1 or LG-mono- or bicyclic heteroaryl-$(CH_2)_n$ wherein n=1 to 3, preferably n=1, and wherein heteroaryl comprises 5 to 10 ring atoms wherein 1 or 2 ring atoms are hetero-atoms.

More preferably, Y is

Leaving Group (LG), branched or straight-chain LG-$C_1$-$C_{10}$ alkyl wherein the alkyl chain is optionally interrupted by 1 or 2 oxygen atoms with the proviso that there are at least two methylene groups between two oxygen atoms, or branched or straight-chain LG-$C_1$-$C_{10}$ alkoxy wherein the carbon chain is optionally interrupted by 1 additional oxygen atom with the proviso that there are at least two methylene groups between two oxygen atoms.

Even more preferably, Y is

Leaving Group (LG), branched or straight-chain LG-$C_1$-$C_{10}$ alkyl or branched or straight-chain LG-$C_1$-$C_{10}$ alkoxy.

Even more preferably, Y is Leaving Group (LG) or branched or straight-chain LG-$C_1$-$C_{10}$ alkyl.

Preferred features disclosed below apply to (IIIA):

Preferably, Y is

Leaving Group (LG) with the proviso that there is no double bond between C-4 and C-5, branched or straight-chain LG-$C_1$-$C_{10}$ alkyl wherein the carbon chain is optionally interrupted by 1 or 2 oxygen atoms with the proviso that there are at least two methylene groups between two oxygen atoms, branched or straight-chain LG-$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms, LG-$C_3$-$C_6$ cycloalkyl with the proviso that LG is attached to one of the $CH_2$ groups of the ring, LG-$C_3$-$C_6$ cycloalkyl-$(CH_2)_n$, wherein n=1 to 3, preferably n=1, with the proviso that LG is attached to one of the $CH_2$ groups of the ring, LG-$C_6$-$C_{10}$ mono- or bicyclic aryl-$(CH_2)_n$—O, wherein n=1 to 3 preferably n=1 with the proviso that there is no double bond between C-4 and C-5 or LG-mono- or bicyclic heteroaryl-$(CH_2)_n$—O wherein n=1 to 3, preferably n=1 with the proviso that there is no double bond between C-4 and C-5 and wherein heteroaryl comprises 5 to 10 ring atoms wherein 1 or 2 ring atoms are hetero-atoms.

More preferably, Y is

Leaving Group (LG) with the proviso that there is no double bond between C-4 and C-5, branched or straight-chain LG-$C_1$-$C_{10}$ alkyl wherein the carbon chain is optionally interrupted by 1 or 2 oxygen atoms with the proviso that there are at least two methylene groups between two oxygen atoms, branched or straight-chain LG-$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms.

Even more preferably, Y is

Leaving Group (LG) with the proviso that there is no double bond between C-4 and C-5, branched or straight-chain LG-$C_1$-$C_{10}$ alkyl wherein the carbon chain is optionally interrupted by 1 or 2 oxygen atoms with the proviso that there are at least two methylene groups between two oxygen atoms, LG-$C_6$-$C_{10}$ mono- or bicyclic aryl-$(CH_2)_n$ wherein n=1 to 3, preferably n=1, LG-mono- or bicyclic heteroaryl-$(CH_2)_n$ wherein n=1 to 3, preferably n=1 and wherein heteroaryl comprises 5 to 10 ring atoms wherein 1 or 2 ring atoms are hetero-atoms.

Even more preferably, Y is branched or straight-chain LG-$C_1$-$C_{10}$ alkyl wherein the carbon chain is optionally interrupted by 1 or 2 oxygen atoms with the proviso that there are at least two methylene groups between two oxygen atoms, LG-$C_6$-$C_{10}$ mono- or bicyclic aryl-$(CH_2)_n$ wherein n=1 to 3, preferably n=1, LG-mono- or bicyclic heteroaryl-$(CH_2)_n$ wherein n=1 to 3, preferably n=1 and wherein heteroaryl comprises 5 to 10 ring atoms wherein 1 or 2 ring atoms are hetero-atoms.

Even more preferably, Y is branched or straight-chain LG-$C_1$-$C_{10}$ alkyl, more preferably LG-$C_1$-$C_3$ alkyl.

Preferred features disclosed below apply to (IIIB):

Preferably Y is branched or straight-chain LG-$C_1$-$C_{10}$ alkyl wherein the alkyl chain is optionally interrupted by 1 or 2 oxygen atoms with the proviso that there are at least two methylene groups between two oxygen atoms, LG-$C_6$-$C_{10}$ mono- or bicyclic aryl-$(CH_2)_n$ wherein n=1 to 3, preferably n=1 or LG-mono- or bicyclic heteroaryl-$(CH_2)_n$ wherein n=1 to 3, preferably n=1, and wherein heteroaryl comprises 5 to 10 ring atoms wherein 1 or 2 ring atoms are hetero-atoms.

More preferably, Y is branched or straight-chain LG-$C_1$-$C_{10}$ alkyl wherein the alkyl chain is optionally interrupted by 1 or 2 oxygen atoms with the proviso that there are at least two methylene groups between two oxygen atoms.

Even more preferably, Y is branched or straight-chain LG-$C_1$-$C_{10}$ alkyl, more preferably, LG-$C_1$-$C_3$ alkyl.

Preferred features disclosed below apply to (IIIB):

Y is branched or straight-chain LG-$C_1$-$C_{10}$ alkyl wherein the carbon chain is optionally interrupted by 1 or 2 oxygen atoms with the proviso that there are at least two methylene groups between two oxygen atoms, LG-$C_3$-$C_6$ cycloalkyl with the proviso that LG is attached to one of the $CH_2$ groups of the ring, LG-$C_3$-$C_6$ cycloalkyl-$(CH_2)_n$, wherein n=1 to 3, preferably n=1, with the proviso that LG is attached to one of the $CH_2$ groups of the ring.

Preferred features disclosed below apply to (IIIA) and (IIIB):

Preferably, branched or straight-chain LG-$C_1$-$C_{10}$ alkyl is LG-$C_1$-$C_6$ alkyl or LG-$C_7$-$C_{10}$ alkyl. More preferably, LG-$C_1$-$C_{10}$ alkyl is LG-$C_1$-$C_3$ alkyl, LG-$C_1$ methyl (LG-$CH_2$), LG-ethyl (LG-$(CH_2)_2$), LG-propyl (e.g. LG-$(CH_2)_3$), LG-butyl (e.g. LG-$(CH_2)_4$) or LG-pentyl (e.g. LG-$(CH_2)_5$). Alkyl chain can be substituted at any position with the Leaving Group (LG). Preferably, alkyl chain is substituted with the Leaving Group (LG) at the terminal position of the chain. Preferably, branched or straight-chain LG-$C_1$-$C_{10}$ alkyl wherein the alkyl chain is optionally interrupted by 1 or 2 oxygen atoms with the proviso that there are at least two methylene groups between two oxygen atoms is 3-[(methylsulfonyl)oxy]propyl, 3-{[(4-methylphenyl)sulfonyl]oxy}propyl, 3-{[(4-nitrophenyl)sulfonyl]oxy}propyl, 3-{[(trifluoromethyl)sulfonyl]oxy}propyl, (methylsulfonyl)oxymethyl, [(4-methylphenyl)sulfonyl]oxymethyl, [(4-nitrophenyl)sulfonyl]oxymethyl, [(trifluoromethyl)sulfonyl]oxymethyl, {2-[(methylsulfonyl)oxy]ethoxy}methyl, (2-{[(4-methylphenyl)sulfonyl]oxy}ethoxy)methyl, (2-{[(4-nitrophenyl)sulfonyl]oxy}ethoxy)methyl, (2-{[(trifluoromethyl)sulfonyl]oxy}ethoxy)methyl, 3-{2-[(methylsulfonyl)oxy]ethoxy}propyl, 3-(2-{[(4-methylphenyl)sulfonyl]oxy}ethoxy)propyl, 3-(2-{[(4-nitrophenyl)sulfonyl]oxy}ethoxy)propyl, 3-(2-{[(trifluoromethyl)sulfonyl]oxy}ethoxy)propyl.

Preferably, branched or straight-chain LG-$C_1$-$C_{10}$ alkoxy is LG-$C_2$-$C_6$ alkoxy or LG-$C_7$-$C_{10}$ alkoxy. More preferably, LG-$C_2$-$C_{10}$ alkoxy is LG-$C_2$ alkoxy (LG-$(CH_2)_2$O), LG-$C_3$ alkoxy (e.g. LG-$(CH_2)_3$O), LG-$C_4$ alkoxy (e.g. LG-$(CH_2)_4$O) or LG-$C_5$ alkoxy (e.g. LG-$(CH_2)_5$O). The alkoxy chain can be substituted at any carbon atom with the Leaving Group (LG).

Preferably, alkoxy chain is substituted with the Leaving Group (LG) at the terminal position of the chain.

Preferably, branched or straight-chain LG-$C_1$-$C_{10}$ alkoxy wherein the carbon chain is optionally interrupted by 1 additional oxygen atom with the proviso that there are at least two methylene groups between two oxygen atoms is 2-[(methylsulfonyl)oxy]ethoxy, 2-{[(4-methylphenyl)sulfonyl]oxy}ethoxy, 2-{[(4-nitrophenyl)sulfonyl]oxy}ethoxy, 2-{[(trifluoromethyl)sulfonyl]oxy}ethoxy, 3-[(methylsulfonyl)oxy]propan-1-oxy, 3-{[(4-methylphenyl)sulfonyl]oxy}propan-1-oxy, 3-{[(4-nitrophenyl)sulfonyl]oxy}propan-1-oxy, 3-{[(trifluoromethyl)sulfonyl]oxy}propan-1-oxy, 2-{2-[(methylsulfonyl)oxy]ethoxy}ethoxy, 2-(2-{[(4-methylphenyl)sulfonyl]oxy}ethoxy)ethoxy, 2-(2-{[(4-nitrophenyl)sulfonyl]oxy}ethoxy)ethoxy, 2-(2-{[(trifluoromethyl)sulfonyl]oxy}ethoxy)ethoxy.

Preferably, LG-$C_6$-$C_{10}$ mono- or bicyclic aryl-$(CH_2)_n$ is LG-$C_6H_4$—$(CH_2)_n$ wherein n=1 to 3, preferably n=1. Aryl can be substituted at any position with the Leaving Group (LG).

Preferably, LG-$C_6$-$C_{10}$ mono- or bicyclic aryl-$(CH_2)_n$ is LG-$C_6$aryl-$(CH_2)_n$ wherein n=1 to 3, preferably n=1. Aryl is substituted at any position with the Leaving Group (LG). Aryl is optionally substituted.

Preferably, LG-mono- or bicyclic heteroaryl-$(CH_2)_n$ is LG-pyridinyl-$(CH_2)_n$ or LG-pyrimidinyl-$(CH_2)_n$ wherein n=1 to 3, preferably n=1. Heteroaryl can be substituted at any carbon atom with the Leaving Group (LG). Heteroaryl is optionally substituted.

Preferably, LG-$C_3$-$C_6$ cycloalkyl is LG-$C_3$ cycloalkyl, LG-$C_4$ cycloalkyl, LG-$C_5$ cycloalkyl or LG-$C_6$ cycloalkyl. Cycloalkyl can be substituted at any position of the $CH_2$ groups of the ring with the Leaving Group (LG)

Preferably, LG-$C_3$-$C_6$ cycloalkyl-$(CH_2)_n$ is LG-$C_3$ cycloalkyl-$(CH_2)_n$, LG-$C_4$ cycloalkyl-$(CH_2)_n$, LG-$C_5$ cycloalkyl-$(CH_2)_n$ or LG-$C_6$ cycloalkyl-$(CH_2)_n$ wherein n=1 to 3, preferably n=1. Cycloalkyl can be substituted at any position of the $CH_2$ groups of the ring with the Leaving Group (LG)

Preferably, LG-$C_6$-$C_{10}$ mono- or bicyclic aryl-$(CH_2)_n$—O is LG-$C_6H_4$—$(CH_2)_n$O wherein n=1 to 3, preferably n=1. Aryl can be substituted at any position with the Leaving Group (LG).

Preferably, LG-mono- or bicyclic heteroaryl-$(CH_2)_n$—O is LG-pyridinyl-$(CH_2)_n$O or LG-pyrimidinyl-$(CH_2)_n$O wherein n=1 to 3, preferably n=1. Heteroaryl can be substituted at any carbon atom with the Leaving Group (LG).

Embodiments and preferred features can be combined together and are within the scope of the invention.

Preferably, the Leaving Group (LG), if attached to an $sp^3$-hybridized carbon atom, is selected from the group of
Halogen,
Methylsulfonyloxy,
Trifluoromethylsulfonyloxy,
(4-Nitrophenyl)sulphonyloxy
Nonafluorobutylsulfonyloxy, and
(4-Methylphenyl)sulfonyloxy.

More preferably, the Leaving Group (LG), if attached to an $sp^3$-hybridized carbon atom, is selected from the group of
Chloro,
Bromo,
Methylsulfonyloxy,
Trifluoromethylsulfonyloxy,
(4-Nitrophenyl)sulphonyloxy
Nonafluorobutylsulfonyloxy,
(4-Methylphenyl)sulfonyloxy, and
Iodo.

Even more preferably, the Leaving Group (LG), if attached to an $sp^3$-hybridized carbon atom, is selected from the group of
Methylsulfonyloxy,
Trifluoromethylsulfonyloxy,
(4-Nitrophenyl)sulphonyloxy
Nonafluorobutylsulfonyloxy, and
(4-Methylphenyl)sulfonyloxy.

Even more preferably, the Leaving Group (LG), if attached to an $sp^3$-hybridized carbon atom, is (4-Methylphenyl)sulfonyloxy.

Preferably, the Leaving Group (LG), if attached to aryl or heteroaryl, is selected from the group of
halogen
nitro,
trimethyl ammonium,
4-methoxyphenyliodonium, and
2-thienyliodonium.

More preferably, the Leaving Group (LG), if attached to aryl or heteroaryl, is selected from the group of
bromo,
iodo,
nitro,
trimethyl ammonium,
4-methoxyphenyliodonium, and
2-thienyliodonium.

$R^4$ or $R^5$ is an O-protecting group selected from the group comprising
Methyl, Ethyl, Propyl, Butyl, t-Butyl, Allyl, Benzyl, 4-Methoxybenzyl, 4-Methoxyphenyl.

Preferably, $R^4$ is an O-protecting group selected from the group comprising Methyl, Ethyl, t-Butyl, Benzyl.

N-protecting groups are selected from the group comprising
Carbobenzyloxy (Cbz), p-Methoxybenzyl carbonyl (Moz or MeOZ), tert-Butyloxycarbonyl (BOC), 9-Fluorenylmethyloxycarbonyl (FMOC), Benzyl (Bn), p-Methoxybenzyl (PMB), 3,4-Dimethoxybenzyl (DMPM), Triphenylmethyl and p-methoxyphenyl (PMP) or the group $NR^6R^7$ is a 1,3-dioxo-1,3-dihydro-2H-isoindol-2-yl (phthalimido) or an azido group.

Preferably, $R^6$ and $R^7$ are selected independently from each other from the group comprising Carbobenzyloxy (Cbz), p-Methoxybenzyl carbonyl (Moz or MeOZ), tert-Butyloxycarbonyl (BOC), 9-Fluorenylmethyloxycarbonyl (FMOC), Benzyl (Bn).

More preferably, $R^6$ and $R^7$ are selected independently from each other from the group comprising tert-Butyloxycarbonyl (BOC) and 9-Fluorenylmethyloxycarbonyl (FMOC).

Even more preferably, $R^6$ is N-protecting group and $R^7$ is Hydrogen or a N-protecting group.

Invention compounds are selected from but not limited to 1-tert-Butyl 6-ethyl (2S)-2-[(tert-butoxycarbonyl)amino]-5-[(methylsulfonyl)oxy]hexanedioate

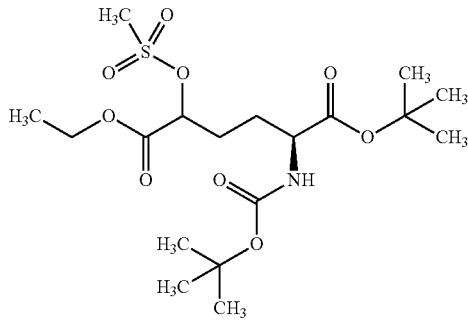 [SMILES: CCOC(=O)C(CC[C@H](NC(=O)OC(C)(C)C)C(=O)OC(C)(C)C)OS(C)(=O)=O]

1-tert-Butyl 6-ethyl (2S)-2-[(tert-butoxycarbonyl)amino]-5-{3-[(methylsulfonyl)oxy]propyl}hexanedioate

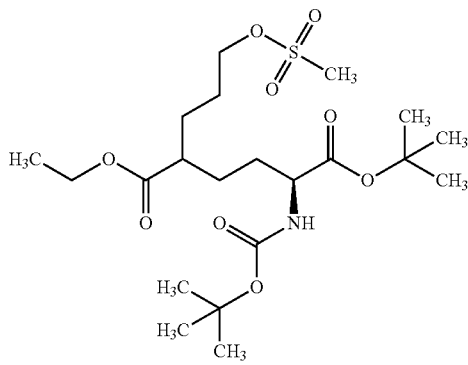 [SMILES: CCOC(=O)C(CCCOS(C)(=O)=O)CC[C@H](NC(=O)OC(C)(C)C)C(=O)OC(C)(C)C]

1-tert-Butyl 6-ethyl (2S)-2-[(tert-butoxycarbonyl)amino]-5-(3-{[(4-methylphenyl)sulfonyl]oxy}propyl)hexanedioate

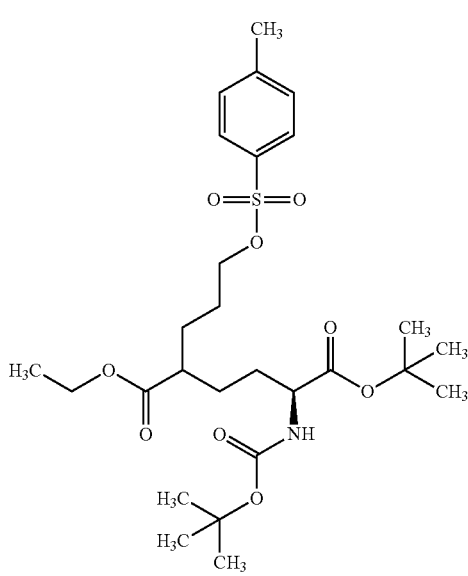 [SMILES: CCOC(=O)C(CCCOS(=O)(=O)c1ccc(C)cc1)CC[C@H](NC(=O)OC(C)(C)C)C(=O)OC(C)(C)C]

In a fourth aspect, the invention is directed to a composition comprising compounds of the general formula (I), (II), (III), (IA), (IA2S), (IB), (IB2S), (IIA), (IIA2S), (IIB), (IIB2S), (IIIA), (IIIA2S), (IIIB), or (IIIB2S) or mixture thereof and pharmaceutically acceptable carrier or diluent.

The person skilled in the art is familiar with auxiliaries, vehicles, excipients, diluents, carriers or adjuvants which are suitable for the desired pharmaceutical formulations, preparations or compositions on account of his/her expert knowledge.

The administration of the compounds, pharmaceutical compositions or combinations according to the invention is performed in any of the generally accepted modes of administration available in the art. Intravenous deliveries are preferred.

Generally, the pharmaceutical compositions according to the invention can be administered such that the dose of the active compound is in the range of 37 MBq (1 mCi) to 740 MBq (20 mCi). In particular, a dose in the range from 150 MBq to 370 MBq will be used.

In a fifth aspect, the invention is directed to method for obtaining compound of formula (I), (IA), (IB), (II), (IIA) or (IIB) or mixture thereof. The method of the invention is a fluoro-labeling method. Preferably, the fluoro-labeling method concerns a method for labeling invention compounds with Fluorine atom (F) containing moiety wherein the Fluorine atom (F) containing moiety preferably comprises $^{18}$F or $^{19}$F.

More preferably, Fluorine atom (F) containing moiety comprises $^{18}$F. Even more preferably, the Fluorine atom (F) containing moiety is 4,7,13,16,21,24-Hexaoxa-1,10-diazabicyclo[8.8.8]-hexacosane K18F (crownether salt Kryptofix K18F), $K^{18}F$, $H^{18}F$, $KH^{18}F_2$, $Cs^{18}F$, $Na^{18}F$ or tetraalkylammonium salt of $^{18}$F (e.g.[F-18]tetrabutylammonium fluoride). Most preferably, the Fluorine atom (F) containing moiety is $K^{18}F$, $H^{18}F$, or $KH^{18}F_2$.

Preferably, the fluoro-labeling method is a fluoro-radiolabeling method.

Under the present invention, the method is a direct labelling method for obtaining compound of formula (I), (IA), (IB), (II), (IIA) or (IIB) or mixture thereof.

The fluoro-labeling method comprises the steps

Coupling compound of general Formula (III), (IIIA) or (IIIB) with Fluorine atom (F) containing moiety, Deprotecting compound of formula (II), (IIA) or (IIB) and Optionally converting obtained compound into suitable salts of inorganic or organic acids thereof, hydrates, complexes, esters, amides, and solvates thereof.

Preferably, the method is a direct labelling method for obtaining compound of formula (I), (IA), (IB), (II), (IIA) or (IIB) or mixture thereof.

The fluoro-labeling method comprises the steps

Coupling compound of general Formula (III), (IIIA) or (IIIB) with Fluorine atom (F) containing moiety wherein the Fluorine atom (F) containing moiety comprises $^{18}$F, Deprotecting compound of formula (II), (IIA) or (IIB) and Optionally converting obtained compound into suitable salts of inorganic or organic acids thereof, hydrates, complexes, esters, amides, and solvates thereof.

Preferably, the method is a direct labelling method for obtaining compound of formula (I), (IA), (IB), (II), (IIA) or (IIB) or mixture thereof.

The fluoro-labeling method comprises the steps
Coupling compound of general Formula (III), (IIIA) or (IIIB) with Fluorine atom (F) containing moiety wherein the Fluorine atom (F) containing moiety comprises $^{19}$F,
Deprotecting compound of formula (II), (IIA) or (IIB) and
Optionally converting obtained compound into suitable salts of inorganic or organic acids thereof, hydrates, complexes, esters, amides, and solvates thereof.

The reagents, solvents and conditions which can be used for this fluorination are common and well-known to the skilled person in the field. See, e.g., *J. Fluorine Chem.*, 27 (1985):177-191.

Preferably, the solvents used in the present method is DMF, DMSO, acetonitrile, DMA, or mixture thereof, preferably the solvent is DMSO.

A method for obtaining a compound of formula (I), (IA), (IB), (II), (IIA) or (IIB) or mixture thereof
wherein the compound of formula (I) is as disclosed above.
Compounds of formula (I), (IA), (IB), (II), (IIA), (IIB), (III), (IIIA) and (IIIB) are defined as above wherein embodiment and preferred features are herein enclosed.

A method for obtaining compound of formula (IA2S), (IB2S), (IIA2S), or (IIB2S) or mixture thereof comprising the steps
Coupling compound of general Formula (IIIA2S) or (IIIB2S) with Fluorine atom (F) containing moiety,
Optionally deprotecting compound of formula (IIA2S) or (IIB2S) and
Optionally converting obtained compound into suitable salts of inorganic or organic acids thereof, hydrates, complexes, esters, amides, and solvates thereof.

Preferably, the method concerns compound of formula (IA2S), (IB2S), (IIA2S), or (IIB2S) wherein the Fluorine atom (F) is an $^{18}$F. and the Fluorine atom (F) containing moiety is 4,7,13,16,21,24-Hexaoxa-1,10-diazabicyclo [8.8.8]-hexacosane K18F (crown ether salt Kryptofix K18F), K$^{18}$F, H$^{18}$F, KH$^{18}$F$_2$, Cs$^{18}$F, Na$^{18}$F or tetraalkylammonium salt of $^{18}$F (e.g. [F-18]tetrabutylammonium fluoride). Most preferably, the Fluorine atom (F) containing moiety is K$^{18}$F, H$^{18}$F, or KH$^{18}$F$_2$.

Preferably, the method concerns compound of formula (IA2S), (IB2S), (IIA2S), or (IIB2S) wherein the Fluorine atom (F) is an $^{19}$F. and the Fluorine atom (F) containing moiety is Fluorine or fluorine-bearing building block.

Compounds of formula (IA2S), (IB2S), (IIA2S), (IIB2S), (IIIA2S), or (IIIB2S) are disclosed above and are enclosed herein.

In a sixth aspect, the invention is directed to compounds of general formula (I) or (II) for the manufacture of an imaging tracer for imaging proliferative diseases.

In other word, the invention is directed to the use of invention compounds of general formula (I) and (II) for the manufacture of an imaging tracer for imaging proliferative diseases.

The compounds of general formula (I) and (II) are herein defined as above and encompass all embodiments and preferred features. Preferably, the invention compounds are compounds of general formula (I) or (II) wherein the Fluorine atom (F) is $^{18}$F isotope.

The imaging tracer is Positron Emission Tomography PET suitable imaging tracer.

The invention is also directed to a method for imaging or diagnosis proliferative diseases comprising the steps:

Administrating to a mammal an effective amount of a compound comprising compounds of general formula (I) or (II),
Obtaining images of the mammal and
Assessing images.

Proliferative diseases are cancer characterised by the presence of tumor and/or metastases. Preferably, tumour are selected from the group of malignomas of the gastrointestinal or colorectal tract, liver carcinoma, pancreas carcinoma, kidney carcinoma, bladder carcinoma, thyroid carcinoma, prostate carcinoma, endometrial carcinoma, ovary carcinoma, testes carcinoma, melanoma, small-cell and non-small-cell bronchial carcinoma, dysplastic oral mucosa carcinoma, invasive oral cancer; breast cancer, including hormone-dependent and hormone-independent breast cancer, squamous cell carcinoma, neurological cancer disorders including neuroblastoma, glioma, astrocytoma, osteosarcoma, meningioma, soft tissue sarcoma; haemangioma and endocrine tumours, including pituitary adenoma, chromocytoma, paraganglioma, haematological tumour disorders including lymphoma and leukaemias; Preferably, the tumor is bronchial carcinoma (lung tumor) or prostate carcinoma.

Preferably, metastases are metastases of one of the tumours mentioned above.

Preferably, the invention compounds and use is for manufacturing a PET imaging tracer for imaging tumor in a mammal wherein the tumor is preferably a non-small-cell carcinoma (lung tumor).

Compounds of general formula (IA2S), (IB2S), (IIA2S), or (IIB2S) or mixture thereof for the manufacture of an imaging tracer for imaging proliferative diseases.

In a seventh aspect, the invention is directed to the use of compounds of general formula (I), (II) or (III) for conducting biological assays and chromatographic identification. More preferably, the use relates to compounds of general formula (I) or (II) wherein the fluorine isotope is $^{18}$F or $^{19}$F, more preferably $^{19}$F.

Compounds of general formula (I), (II) or (III) wherein the fluorine isotope is $^{19}$F are useful as reference and/or measurement agent.

The compounds of general formula (I), (II) and (III) are herein defined as above and encompass all embodiments and preferred features.

Use of compounds of general formula (IA2S), (IB2S), (IIA2S), (IIB2S), (IIIA2S), or (IIIB2S) for conducting biological assays and chromatographic identification. More preferably, the use relates to compounds of general formula (IA2S), (IB2S), (IIA2S), (IIB2S), (IIIA2S), or (IIIB2S) wherein the fluorine isotope is $^{18}$F or $^{19}$F, more preferably $^{19}$F.

In a eighth aspect, the present invention provides a kit comprising a sealed vial containing a predetermined quantity of a compound having general chemical Formula (I), (II) or (III) and suitable salts of inorganic or organic acids thereof, hydrates, complexes, esters, amides, and solvates thereof. Optionally the kit comprises a pharmaceutically acceptable carrier, diluent, excipient or adjuvant.

A kit comprising a sealed vial containing a predetermined quantity of a compound having general chemical Formula (IA2S), (IB2S), (IIA2S), (IIB2S), (IIIA2S), or (IIIB2S) and suitable salts of inorganic or organic acids thereof, hydrates, complexes, esters, amides, and solvates thereof. Optionally the kit comprises a pharmaceutically acceptable carrier, diluent, excipient or adjuvant. Preferably, the kit comprises a sealed vial containing a predetermined quantity of a compound having general chemical Formula (IIIA2S) or (IIIB2S).

Definitions

The terms used in the present invention are defined below but are not limiting the invention scope.

If chiral centers or other forms of isomeric centers are present in a compound according to the present invention, all forms of such stereoisomers, including enantiomers and diastereoisomers, are intended to be covered herein. Compounds containing chiral centers may be used as racemic mixture or as an enantiomerically enriched mixture or as a diastereomeric mixture or as a diastereomerically enriched mixture, or these isomeric mixtures may be separated using well-known techniques, and an individual stereoisomer maybe used alone. In cases in which compounds have carbon-carbon double bonds, both the (Z)-isomers and (E)-isomers as well as mixtures thereof are within the scope of this invention. In cases wherein compounds may exist in tautomeric forms, such as keto-enol tautomers, each tautomeric form is contemplated as being included within this invention whether existing in equilibrium or predominantly in one form.

In the context of the present invention, preferred suitable salts are pharmaceutically acceptable salts of the compounds according to the invention. The invention also comprises salts which for their part are not suitable for pharmaceutical applications, but which can be used, for example, for isolating or purifying the compounds according to the invention.

Pharmaceutically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Pharmaceutically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N methylmorpholine, arginine, lysine, ethylenediamine and N methylpiperidine.

The term "$C_1$-$C_{10}$ alkyl", used herein on its own or as part of another group, refers to saturated carbon chains which may be straight-chain or branched, in particular to methyl, ethyl, n-propyl, isopropyl, n-butyl, isobutyl, tert-butyl, methylpropyl, n-pentyl, 2,2-dimethylpropyl, 2-methylbutyl, 3-methylbutyl, n-hexyl, n-heptyl, n-octyl, n-nonyl or n-decyl groups. Preferably, alkyl is methyl, ethyl, propyl, butyl, pentyl or hexyl.

The term "$C_1$-$C_{10}$-alkoxy" used herein on its own or as part of another group, refers to an O-alkyl chain, in particular to methoxy, ethoxy, n-propoxy, n-butoxy, n-pentyloxy, n-hexyloxy, n-heptyloxy, n-octyloxy, n-nonyloxy or n-decyloxy group. Preferably, alkoxy is methoxy, ethoxy, n-propoxy, n-butoxy, n-pentyloxy or n-hexyloxy.

The term "aryl" as employed herein by itself or as part of another group refers to monocyclic or bicyclic $C_6$-$C_{10}$ aromatic rings, in particular phenyl or naphthyl groups e.g. 1-naphthyl and 2-naphthyl, which themselves can be substituted with one or two substituents independently and individually selected from but not limited to the group comprising halogen, $NO_2$, CN, COOH, ($C_1$-$C_3$)alkyl, formyl, acetyl, alkoxycarbonyl or trifluoromethyl.

The term "heteroaryl" as employed herein by itself or as part of another group refers to monocyclic or bicyclic heteroaromatic groups containing from 5 to 10 ring atoms, wherein 1 or 2 atoms of the ring portion are independently selected from N, O or S, e.g. thienyl, furanyl, pyrrolyl, oxazolyl, thiazolyl, imidazolyl, pyrazolyl, isoxazolyl, isothiazolyl, benzofuranyl, benzothienyl, benzothiazolyl, benzoxazolyl, benzimidazolyl, indazolyl, indolyl, pyridyl, pyridazinyl, pyrimidinyl, pyrazinyl, quinolyl, isoquinolyl etc.; which themselves can be substituted with one or two substituents independently and individually selected from but not limited to the group comprising halogen, $NO_2$, CN, COOH, ($C_1$-$C_3$)alkyl, formyl, acetyl, alkoxycarbonyl or trifluoromethyl.

The term "$C_3$-$C_6$ cycloalkyl" used herein on its own or as part of another group, refers to cyclopropyl, cyclobutyl, cyclopentyl or cyclohexyl which can be substituted with one or two ($C_1$-$C_3$)alkyl or ($C_1$-$C_3$)alkoxy groups.

Halogen as used herein refers to fluoro, chloro, bromo or iodo.

The term "amine-protecting group" as employed herein by itself or as part of another group is known or obvious to someone skilled in the art, which is chosen from but not limited to a class of protecting groups namely carbamates, amides, imides, N-alkyl amines, N-aryl amines, imines, enamines, boranes, N—P protecting groups, N-sulfenyl, N-sulfonyl and N-silyl, and which is chosen from but not limited to those described in the textbook Greene and Wuts, Protecting groups in Organic Synthesis, third edition, page 494-653, included herewith by reference.

Amino protecting groups are selected from the group comprising
Carbobenzyloxy (Cbz), p-Methoxybenzyl carbonyl (Moz or MeOZ), tert-Butyloxycarbonyl (BOC), 9-Fluorenylmethyloxycarbonyl (FMOC), Benzyl (Bn), p-Methoxybenzyl (PMB), 3,4-Dimethoxybenzyl (DMPM), Triphenylmethyl and p-methoxyphenyl (PMP) or the protected amino group is a 1,3-dioxo-1,3-dihydro-2H-isoindol-2-yl (phthalimido) or an azido group.

O-protecting groups are selected from the group comprising
Methyl, Ethyl, Propyl, Butyl, t-Butyl, Allyl, Benzyl, 4-Methoxybenzyl, 4-Methoxyphenyl.

The term "leaving group" as employed herein by itself or as part of another group is known or obvious to someone skilled in the art, and means that an atom or group of atoms is detachable from a chemical substance by a nucleophilic agent. Examples are given e.g. in Synthesis (1982), p. 85-125, table 2 (p. 86; (the last entry of this table 2 needs to be corrected: "n-$C_4F_9$S(O)$_2$—O— nonaflat" instead of "n-$C_4H_9$S(O)$_2$—O— nonaflat"), Carey and Sundberg, Organische Synthese, (1995), page 279-281, table 5.8; or Netscher, Recent Res. Dev. Org. Chem., 2003, 7, 71-83, scheme 1, 2, 10 and 15 and others). (Coenen, Fluorine-18 Labeling Methods Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, FIG. 7 pp 33).

Unless otherwise specified, when referring to the compounds of formula the present invention per se as well as to any pharmaceutical composition thereof the present invention includes all of the hydrates, salts, and complexes.

General synthesis of F-18 compounds: alkyl-F and heteroaryl-F

The radiofluorination reaction can be carried out, for example in a typical reaction vessel (e.g. Wheaton vial) which is known to someone skilled in the art or in a microreactor. The reaction can be heated by typical methods, e.g. oil bath, heating block or microwave. The radiofluorination reactions are carried out in dimethylformamide with potassium carbonate as base and "kryptofix" as crown-ether. But also other solvents can be used which are well known to experts. These possible conditions include, but are not limited to: dimethylsulfoxid and acetonitril as solvent and tetraalkyl ammonium and tertraalkyl phosphonium carbonate as base. Water and/or alcohol can be involved in such a reaction as co-solvent. The radiofluorination reactions are conducted for one to 60 minutes. Preferred reaction times are five to 50 minutes. Further preferred reaction times are 10 to 40 min. This and other conditions for such radiofluorination are known to experts (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). The radiofluorination can be carried out in a "hot-cell" and/or by use of a module (eview: Krasikowa, Synthesis Modules and Automation in F-18 labeling (2006), in: Schubiger P. A., Friebe M., Lehmann L., (eds), PET-Chemistry—The Driving Force in Molecular Imaging. Springer, Berlin Heidelberg, pp. 289-316) which allows an automated or semi-automated synthesis.

Aryl-F-18 compounds of general formula I and IA are also accessible via F-19/F-18 exchange of the respective [F-19]-compounds.

Precursors for alkyl-F-18 compounds of general formula I are e.g. tosylates, brosylates, nosylates, mesylates, triflates, nonaflates etc. (formula III) which can be synthesized from the respective hydroxy compounds according to methods known in the art (J. March, Advanced Organic Chemistry, 4$^{th}$ ed. 1992, John Wiley & Sons, pp 352ff). More specifically, a hydroxy group being attached to a sp$^3$ hybridized carbon atom can be converted to a leaving group by an activating agent like thionyl chloride (e.g. Organic and Biomolecular Chemistry; 4; 22; (2006); 4101-4112), phosphorus pentachloride (e.g. Bioorganic and Medicinal Chemistry; 16; 6; (2008); 3309-3320), methanesulfonyl chloride (e.g. Organic and Biomolecular Chemistry; English; 4; 24; (2006); 4514-4525), carbon tetrachloride/triphenylphosphine (Tetrahedron: Asymmetry; English; 19; 5; 2008; 577-583), hydrogen chloride (e.g. Russian Chemical Bulletin; English; 56; 6; 2007; 1119-1124), N-chloro-succinimide/dimethylsulfide (e.g. Bioscience, Biotechnology, and Biochemistry 72; 3; (2008); 851-855), hydrogen bromide (e.g. Journal of Labelled Compounds and Radiopharmaceuticals; 51; 1; (2008); 12-18), phosphorus tribromide (Journal of the American Chemical Society; 130; 12; (2008); 3726-3727), carbon tetrabromide/triphenylphosphine (e.g. Journal of the American Chemical Society; 130; 12; (2008); 4153-4157), N-bromo-succimide/SMe2 (e.g. Chemical Communications (Cambridge, United Kingdom); 1; (2008); 120-122), bromine/triphenylphosphine (e.g. Journal of the American Chemical Society; 130; 12; (2008); 4153-4157), N-bromo-succimide/SMe$_2$ (e.g. Chemical Communications (Cambridge, United Kingdom); 1; (2008); 120-122), Br2/PPh3 (e.g. European Journal of Organic Chemistry; 9; (2007); 1510-1516), mesylchloride, tosylchloride, trifluormethylsulfonylchloride, nona-fluorobutylsulfonylchloride, (4-bromo-phenyl)sulfonylchloride, (4-nitro-phenyl)sulfonylchloride, (2-nitro-phenyl)sulfonylchloride, (4-isopropyl-phenyl)sulfonylchloride, (2,4,6-tri-isopropyl-phenyl)sulfonylchloride, (2,4,6-trimethyl-phenyl)sulfonylchloride, (4-tertbutyl-phenyl)sulfonylchloride, (4-methoxy-phenyl)sulfonylchloride, mesylanhydride, tosylanhydride, trifluormethylsulfonylanhydride, nona-fluorobutylsulfonylanhydride, (4-bromo-phenyl)sulfonylanhydride, (4-nitro-phenyl)sulfonylanhydride, (2-nitro-phenyl)sulfonylanhydride, (4-isopropyl-phenyl)sulfonylanhydride, (2,4,6-tri-isopropyl-phenyl)sulfonylanhydride, (2,4,6-trimethyl-phenyl)sulfonylanhydride, (4-tertbutyl-phenyl)sulfonylanhydride, (4-methoxy-phenyl)sulfonylanhydride etc.

An additional method which is applicable to the synthesis of those alkyl chains R$^8$ in formula III which are interrupted by 1 or 2 oxygen atoms comprises the alkylation of hydroxy compounds by suitable bis(arylsulfonates) or bis(alkylsulfonates) and the like, e.g. bis(tosylates) TsO—(CH$_2$)$_n$—OTs.

Other precursors for F-18 compounds of general formula I are e.g. iodides and bromides and the like whose conversion to the respective fluorides is also known in the art (J. March, see above).

Precursors for aryl-F-18 compounds of general formula I are e.g. aryl or heteroaryl bromides, iodides, nitro compounds, trialkyl ammonium, aryliodonium which can be converted to the respective F-18 compounds of this invention by methods known in the art (L. Cai, S. Lu, V. Pike, Eur. J. Org. Chem 2008, 2853-2873). Starting materials for these precursors are commercially available or can be synthesized by methods known in the art (R. C. Larock, Comprehensive Organic Transformations, VCH Publishers 1989).

Precursors of aryl-F-18 compounds of general formula I and IA like e.g. (2S)-2-Amino-5-(4-cyano-3-[18F]fluorobenzyl)hexanedioic acid can be synthesized e.g. by reactions described in Example 5 involving the appropriate alkylation of ethyl (diethoxyphosphoryl)acetate and subsequent reaction with tert-butyl (S)-2-[(tert-butoxycarbonyl)amino]-4-oxobutanoate according to Wittig-Horner (Chemical Reviews 1974, 74, 87-99) followed by hydrogenation of the double bond according to Example 1f, if desired.

The synthesis of hydroxy compounds as starting materials for tosylates, brosylates, nosylates, mesylates, triflates, nonaflates etc. comprises the deprotection of OH-protecting groups. As one of the very versatile protecting groups might be mentioned the acetyl protecting group. Many others are known in the art, see e.g. T. W. Greene and P. G. M. Wuts, Protective Groups in Organic Synthesis, 3$^{rd}$ ed, 1999, John Wiley & Sons, pp 17ff).

The hydroxy compounds can alternatively be synthesized directly by those skilled in the art by e.g. hydroboration of corresponding vinylic compounds, reduction of carbonyl compounds, or alkylation of deprotonated homoglutamate derivatives with epoxides (R. C. Larock, Comprehensive Organic Transformations, VCH Publishers 1989, p. 479-582) or by direct β-oxidation of carbonyl compounds via sulfonyloxaziridines (F. A. Davis et al., J. Org. Chem. 1984, 49(17), 3241-3243) or MoOPH (J. Mahn et al., JOC 2002, 67, 8440-8449) e.g. at C5.

The protected hydroxy compounds can be obtained by deprotonation of protected homoglutamate at C5 with suitable bases (e.g. lithium diisopropyl amide, lithium hexamethyldisilazide, nBuLi etc.) and reaction with an alkylating agent like oxy-substituted alkyl halides, sulphonates etc bearing a protected hydroxy group (e.g. Lunney et al., J. Med. Chem. 1994, 37(17), 2664.)

The alkoxy-homoglutamate derivates are accordingly accessible to those skilled in the art by etherfication of 5-hydroxyhomoglutamate derivatives e.g. by means of Finkelstein or Mitsunobu reactions (R. C. Larock, Comprehensive Organic Transformations, VCH Publishers 1989, p. 443-453).

Alternatively, the saturated homoglutamate derivatives substituted at C5 can be synthesized by hydrogenation of the corresponding unsaturated derivatives bearing a C—C-double bond between C4 and C5. Latter compounds are accessible by C—C-bond forming reaction between C4 and C5 by methods known to those skilled in the art like metathesis reactions (K. C. Nicolaou et al., Angewandte Chemie Int. Ed. 2005, 44(29), 4490-4527), aldol condensation reactions, or Wittig reactions (R. C. Larock, Comprehensive Organic Transformations, VCH Publishers 1989, p. 129-180). See also Example 1d and 1f, respectively.

An alternative access to homoglutamic acids of this invention is the ring-opening of the respective 6-ring membered lactams e.g. via acidic hydrolysis and stepwise or parallel removal of protecting groups which gives the open-chain compounds of formula I.

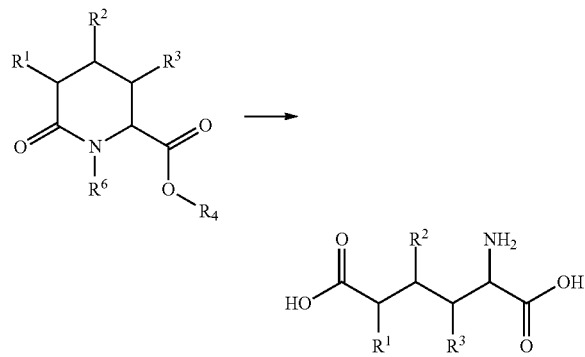

The $^{19}$F-compounds can be synthesized according to the syntheses for the $^{18}$F-compounds (see above), by deoxofluorination reactions (M. Hudlicky, Org. React. 1988, 35, 513; H. Vorbrüggen, Synthesis 2008, 8, 1165-1174), by electrophilic fluorinations (T. Suzuki et al., J. Org. Chem. 2007, 72, 246-250), or by employment of fluorine-bearing building block (see e.g. Example 1a).

The conversion of a hydroxy group being attached to a sp$^3$ hybridized carbon atom to a leaving group is possible with thionyl chloride (e.g. Organic and Biomolecular Chemistry; 4; 22; (2006); 4101-4112), phosphorus pentachloride (e.g. Bioorganic and Medicinal Chemistry; 16; 6; (2008); 3309-3320), methanesulfonyl chloride (e.g. Organic and Biomolecular Chemistry; English; 4; 24; (2006); 4514-4525), carbon tetrachloride/triphenylphosphine (Tetrahedron: Asymmetry; English; 19; 5; 2008; 577-583), hydrogen chloride (e.g. Russian Chemical Bulletin; English; 56; 6; 2007; 1119-1124), N-chloro-succinimide/dimethylsulfide (e.g. Bioscience, Biotechnology, and Biochemistry 72; 3; (2008); 851-855), hydrogen bromide (e.g. Journal of Labelled Compounds and Radiopharmaceuticals; 51; 1; (2008); 12-18), phosphorus tribromide (Journal of the American Chemical Society; 130; 12; (2008); 3726-3727), carbon tetrabromide/triphenylphosphine (e.g. Journal of the American Chemical Society; 130; 12; (2008); 4153-4157), N-bromo-succimide/SMe$_2$ (e.g. Chemical Communications (Cambridge, United Kingdom); 1; (2008); 120-122), bromine/triphenylphosphine (e.g. Journal of the American Chemical Society; 130; 12; (2008); 4153-4157), N-bromo-succimide/SMe$_2$ (e.g. Chemical Communications (Cambridge, United Kingdom); 1; (2008); 120-122), Br$_2$/PPh$_3$ (e.g. European Journal of Organic Chemistry; 9; (2007); 1510-1516), mesylchloride, tosylchloride, trifluormethylsulfonylchloride, nona-fluorobutylsulfonylchloride, (4-bromo-phenyl)sulfonylchloride, (4-nitro-phenyl)sulfonylchloride, (2-nitro-phenyl)sulfonylchloride, (4-isopropyl-phenyl)sulfonylchloride, (2,4,6-tri-isopropyl-phenyl)sulfonylchloride, (2,4,6-trimethyl-phenyl)sulfonylchloride, (4-tertbutyl-phenyl)sulfonylchloride, (4-methoxy-phenyl)sulfonylchloride, mesylanhydride, tosylanhydride, trifluormethylsulfonylanhydride, nona-fluorobutylsulfonylanhydride, (4-bromo-phenyl)sulfonylanhydride, (4-nitro-phenyl)sulfonylanhydride, (2-nitro-phenyl)sulfonylanhydride, (4-isopropyl-phenyl)sulfonylanhydride, (2,4,6-tri-isopropyl-phenyl)sulfonylanhydride, (2,4,6-trimethyl-phenyl)sulfonylanhydride, (4-tertbutyl-phenyl)sulfonylanhydride, (4-methoxy-phenyl)sulfonylanhydride, etc.

EXPERIMENTAL SECTION

Abbreviations

| | |
|---|---|
| br | broad signal (in NMR) |
| d | doublet |
| dd | doublet of doublet |
| DMA | N,N-dimethylacetamide |
| DMF | N,N-dimethylformamide |
| DMSO | dimethylsulphoxide |
| dt | doublet of triplet |
| ESI | electrospray ionisation |
| MS | mass spectrometry |
| m | multiplet |
| MeCN | acetonitrile |
| NMR | nuclear magnetic resonance spectroscopy: chemical shifts (δ) are given in ppm. |
| r. t. | room temperature |
| s | singlet |
| t | triplet |
| THF | tetrahydrofurane |
| TFA | trifluoro acetic acid |

Example 1

1a) Ethyl 2-(diethoxyphosphoryl)-5-fluoropentanoate

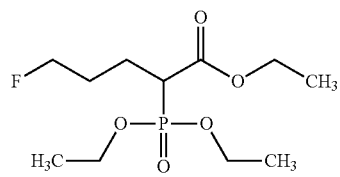 [SMILES: CCOC(=O)C(CCCF)P(=O)(OCC)OCC]

Sodium hydride (2.72 g, 60% on mineral oil, 68.0 mmol) was washed several times with hexanes under an nitrogen atmosphere and was then suspended in dry THF (60 mL). Ethyl (diethoxyphosphoryl)acetate (13.3 g, 59.1 mmol) was added dropwise within 20 min at r.t. as a solution in dry THF (20 mL). After stirring for 2 h at r.t. 1-bromo-3-fluoropropane (10.0 g, 70.9 mmol) was added and the mixture was heated to reflux for 14 h. The mixture was then cooled to r.t. and the reaction was quenched by addition of sat. aq. ammonium chloride solution (50 mL). The mixture was extracted with ethyl acetate (3×50 mL) and the combined organic layers were washed with brine and dried over sodium sulphate. After evaporation of the solvent under reduced pressure the crude product was purified by column chromatography (silica, hexanes/ethyl acetate gradient).

Yield: 3.90 g, 13.7 mmol, 19%.
MS (ESIpos): m/z=285 [M+H]+
¹H-NMR (400 MHz, CHLOROFORM-d): δ [ppm]=1.25-1.37 (m, 9H), 1.66-1.90 (m, 2H), 1.92-2.17 (m, 2H), 2.97 (ddd, 1H), 4.09-4.27 (m, 6H), 4.39 (td, 1H), 4.51 (td, 1H).

1b) tert-Butyl N-(tert-butoxycarbonyl)-L-homoserinate

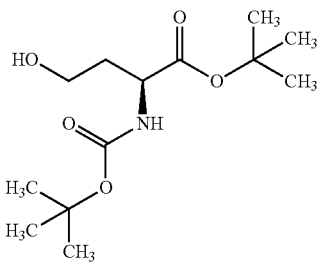 [SMILES: CC(C)(C)OC(=O)N[C@@H](CCO)C(=O)OC(C)(C)C]

To a solution of Boc-L-Asp-OtBu (3.00 g, 10.4 mmol) in 1,2-dimethoxyethane (10 mL) was added at −15° C. 4-methylmorpholine (1.14 mL, 10.4 mmol) and isobutyl chloroformate (1.35 mL, 10.4 mmol). After stirring for 10 min at −15° C. the precipitate was filtered off and washed with cold 1,2-dimethoxyethane (20 mL). To the filtrate was added at −15° C. a solution of sodium borohydride (0.59 g, 15.6 mmol) in water (5 mL). After 5 min water (250 mL) was added. The reaction mixture was extracted with ethyl acetate (3×100 mL), the combined organic layers dried over sodium sulphate, and concentrated under reduced pressure to give the title compound.

Yield: 2.70 g, 9.81 mmol, 95%.
MS (ESIpos): m/z=276 [M+H]+
¹H-NMR (400 MHz, CHLOROFORM-d): δ [ppm]=1.46 (s, 9H), 1.48 (s, 9H), 1.51-1.58 (m, 1H), 2.09-2.20 (m, 1H), 3.45 (br. s., 1H), 3.55-3.76 (m, 2H), 4.31-4.40 (m, 1H), 5.35 (d, 1H).

1c) tert-Butyl (S)-2-[(tert-butoxycarbonyl)amino]-4-oxobutanoate

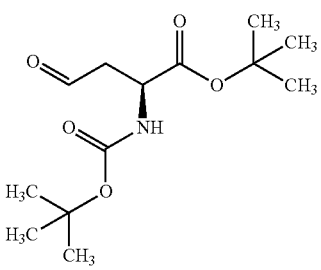 [SMILES: CC(C)(C)OC(=O)N[C@@H](CC=O)C(=O)OC(C)(C)C]

To a solution of tert-Butyl N-(tert-butoxycarbonyl)-L-homoserinate (1.00 g, 3.63 mmol) in dichloromethane (50 mL) was added at r.t. pyridine (0.88 mL, 10.9 mmol) and Dess-Martin-periodinane (2.31 g, 5.45 mmol). After 90 min the reaction mixture was diluted with ethyl acetate (40 mL), washed with 10% sodium thiosulphate solution (30 mL), saturated sodium bicarbonate solution (40 mL), and brine (40 mL). The combined aqueous layers were extracted with ethyl acetate (50 mL) and the combined organic layers were dried over sodium sulphate and concentrated under reduced pressure.

Yield: 0.95 g, 3.48 mmol, 96%.
MS (ESIpos): m/z=274 [M+H]+
¹H-NMR (300 MHz, CHLOROFORM-d): δ [ppm]=1.45 (br. s., 9H), 1.46 (s, 9H), 2.84-3.08 (m, 2H), 4.37-4.54 (m, 1H), 5.37 (d, 1H), 9.74 (s, 1H).

1d) 6-tert-Butyl 1-ethyl (Z)—(S)-5-[(tert-butoxycarbonyl)amino]-2-(3-fluoropropyl)hex-2-ene-dioate;
1e) 6-tert-Butyl 1-ethyl (E)-(S)-5-[(tert-butoxycarbonyl)amino]-2-(3-fluoropropyl)hex-2-enedioate

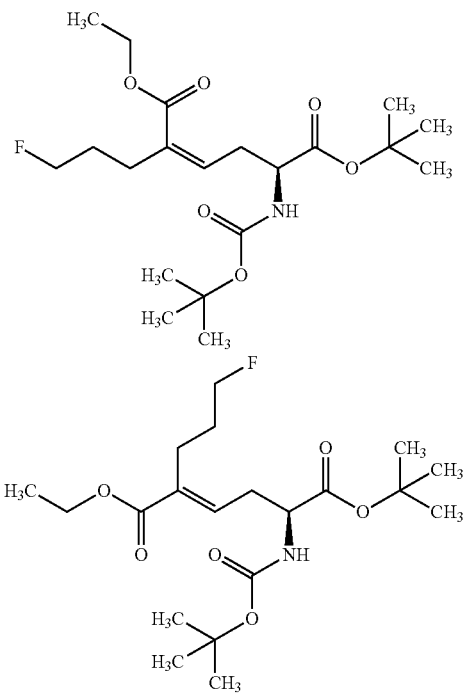

A solution of ethyl 2-(diethoxyphosphoryl)-5-fluoropentanoate (1.30 g, 4.12 mmol) in dry THF (15 mL) was added dropwise at 0° C. to a solution of sodium hydride (0.20 g, 60% on mineral oil, 4.94 mmol) in dry THF (35 mL). After stirring for 15 min tert-Butyl (S)-2-[(tert-butoxycarbonyl)amino]-4-oxobutanoate (1.13 g, 4.12 mmol) was added as a solution in dry THF (15 mL) dropwise to the reaction mixture. After stirring for 90 min at 0° C. the reaction was quenched by addition of saturated sodium bicarbonate solution (50 mL). After phase separation the aqueous layer was extracted with ethyl acetate (3×50 mL) and the combined organic layers were dried over sodium sulphate, concentrated under reduced pressure and the residue was purified by column chromatography (silica, hexanes/ethyl acetate gradient) to give 6-tert-Butyl 1-ethyl (E)-(S)-5-[(tert-butoxycarbonyl)amino]-2-(3-fluoropropyl)hex-2-ene-dioate and 6-tert-Butyl 1-ethyl (Z)—(S)-5-[(tert-butoxycarbonyl)amino]-2-(3-fluoropropyl)hex-2-enedioate as a mixture of diastereomers which were separated by HPLC (Chiralpak IC 5 μm 250×30 mm, hexane/2-propanol 90:10, 50 mL/min) to give 6-tert-Butyl 1-ethyl (E)-(S)-5-[(tert-butoxycarbonyl)amino]-2-(3-fluoropropyl)hex-2-enedioate (1e) (0.75 g, 1.86 mmol, 45%) and 6-tert- Butyl 1-ethyl (Z)—(S)-5-[(tert-butoxycarbonyl)amino]-2-(3-fluoropropyl)hex-2-enedioate (1d) (0.23 g, 0.56 mmol, 14%).

Analytics for 1d) 6-tert-Butyl 1-ethyl (Z)—(S)-5-[(tert-butoxycarbonyl)amino]-2-(3-fluoropropyl)hex-2-enedioate

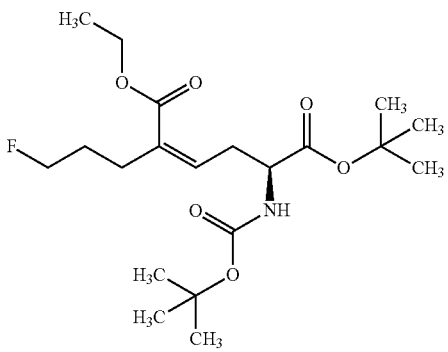 [SMILES: CCOC(=O)/C(=C\C[C@H](NC(=O)OC(C)(C)C)C(=O)OC(C)(C)C)CCCF]

MS (ESIpos): m/z=404 [M+H]$^+$
$^1$H-NMR (300 MHz, CHLOROFORM-d): δ [ppm]=1.32 (t, 3H), 1.44 (s, 9H), 1.46 (s, 9H), 1.61 (s, 4H), 1.74-1.92 (m, 2H), 2.33-2.45 (m, 2H), 2.87 (t, 2H), 4.15-4.31 (m, 2H), 4.36 (dt, 2H), 5.26 (d, 1H), 5.91 (t, 1H).

Analytics for 1e) 6-tert-Butyl 1-ethyl (E)-(S)-5-[(tert-butoxycarbonyl)amino]-2-(3-fluoropropyl)hex-2-enedioate

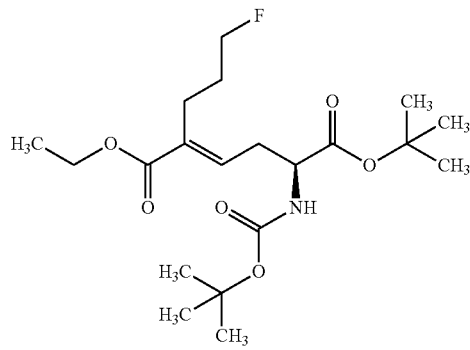

MS (ESIpos): m/z=404 [M+H]$^+$
$^1$H-NMR (300 MHz, CHLOROFORM-d): δ [ppm]=1.13-1.38 (m, 3H), 1.44 (s, 9H), 1.47 (s, 9H), 1.70-1.91 (m, 2H), 2.44 (t, 2H), 2.57-2.78 (m, 2H), 4.20 (q, 2H), 4.35 (t, 2H), 4.50 (t, 1H), 5.17 (d, 1H), 6.75 (t, 1H).

1f) 1-tert-Butyl 6-ethyl (2S)-2-[(tert-butoxycarbonyl)amino]-5-(3-fluoropropyl)hexanedioate

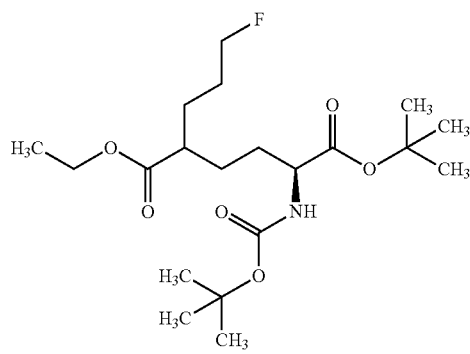 [SMILES: CCOC(=O)C(CCCF)CC[C@H](NC(=O)OC(C)(C)C)C(=O)OC(C)(C)C]

A mixture of 6-tert-Butyl 1-ethyl (E)-(S)-5-[(tert-butoxycarbonyl)amino]-2-(3-fluoropropyl)hex-2-enedioate and 6-tert-Butyl 1-ethyl (Z)—(S)-5-[(tert-butoxycarbonyl)amino]-2-(3-fluoro-propyl)hex-2-enedioate (100 mg, 0.25 mmol) and palladium (20.0 mg, 10% on charcoal, 0.02 mmol) in ethanol (10 mL) were stirred for 2 h at r.t. under a hydrogen atmosphere. Then the mixture was filtered through Celite® and concentrated under reduced pressure. The crude product was purified by column chromatography (silica, hexanes/ethyl acetate gradient).

Yield: 90 mg, 0.22 mmol, 90%.
MS (ESIpos): m/z=406 [M+H]$^+$
$^1$H-NMR (300 MHz, CHLOROFORM-d): δ [ppm]=1.26 (td, 3H), 1.44 (s, 9H), 1.46 (s, 9H), 1.52-1.86 (m, 8H), 2.28-2.46 (m, 1H), 4.08-4.25 (m, 3H), 4.35 (dt, 2H), 5.04 (d, 1H).

1g) 1-tert-Butyl 6-hydrogen (2S)-2-[(tert-butoxycarbonyl)amino]-5-(3-fluoropropyl)hexane-dioate

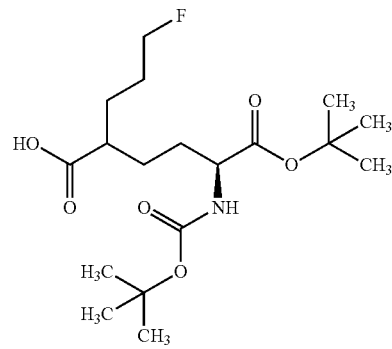 [SMILES: CC(C)(C)OC(=O)N[C@@H](CCC(CCCF)C(=O)O)C(=O)OC(C)(C)C]

A mixture of 1-tert-Butyl 6-ethyl (2S)-2-[(tert-butoxycarbonyl)amino]-5-(3-fluoropropyl)-hexanedioate (1f) (90.0 mg, 0.22 mmol) and lithium hydroxide (53.0 mg, 2.22 mmol) in 1 mL water/ethanol (1:1) was stirred for 14 h at r.t. The mixture was acidified to pH 2 by addition of 2 N aqueous hydrochloric acid and extracted with ethyl acetate (3×5 mL). The combined organic layers were dried over sodium sulphate and concentrated under reduced pressure.
Yield: 57.0 mg, 0.15 mmol, 68%.

1h) Ammonium hydrogen (2S)-2-amino-5-(3-fluoropropyl)hexanedioate

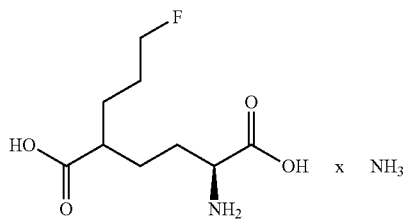

A mixture of 1-tert-Butyl 6-hydrogen (2S)-2-[(tert-butoxycarbonyl)amino]-5-(3-fluoropropyl)-hexanedioate (57.0 mg, 0.15 mmol) and trifluoroacetic acid (0.5 mL) and dichloromethane (0.5 mL) was stirred at r.t. for 30 min. Then the mixture was concentrated under reduced pressure and the residue was purified by preparative HPLC (ZIC HILIC, 5 μm 100×4.6 mm, acetonitrile/0.1 M aqueous ammonium formate solution gradient, 10 mL/min).
Yield: 10.0 mg, 0.04 mmol, 28%.
$^1$H-NMR (300 MHz, DEUTERIUM OXIDE): δ [ppm]=1.45-1.88 (m, 8H), 2.33 (br. s., 1H), 3.64-3.72 (m, 1H), 4.46 (dt, 2H), 8.35 (br. s., 1H).

Example 2

2a) (Z)—(S)-5-[(tert-Butoxycarbonyl)amino]-2-(3-fluoropropyl)hex-2-enedioic acid

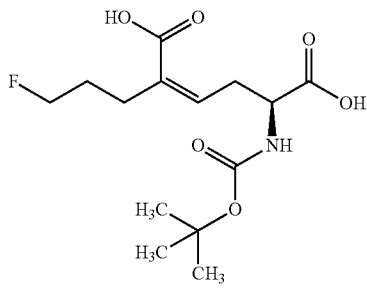 [SMILES: CC(C)(C)OC(=O)N[C@@H](C/C=C(/CCCF)C(=O)O)C(=O)O]

A mixture of 6-tert-Butyl 1-ethyl (Z)—(S)-5-[(tert-butoxycarbonyl)amino]-2-(3-fluoropropyl)hex-2-enedioate (50.0 mg, 0.12 mmol) and lithium hydroxide (29.7 mg, 1.24 mmol) in ethanol (0.5 mL) and water (0.5 mL) was stirred at r.t. for 24 h, 30 min at 60° C. (microwave irradiation), and 14 h at 40° C. (oil bath). The mixture was cooled down to r.t. and acidified to pH 2 by addition of 2 N aqueous hydrochloric acid. The ethanol was then removed under reduced pressure and the aqueous solution extracted with ethyl acetate (3×10 mL). The combined organic layers were washed with brine, dried over sodium sulphate, and concentrated under reduced pressure. The crude product was purified by preparative HPLC (XBridge C18, 5 μm 150×19 mm, acetonitrile/water (0.1% TFA) gradient, 21 mL/min). Yield: 10.0 mg, 0.03 mmol, 25%.

MS (ESIpos): m/z=320 [M+H]$^+$

2b) (Z)—(S)-5-Amino-2-(3-fluoropropyl)hex-2-enedioic acid-trifluoroacetate

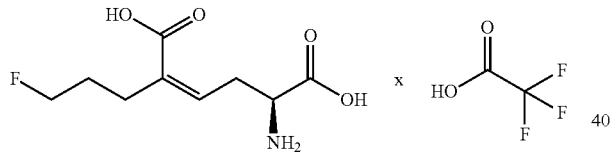

(Z)—(S)-5-[(tert-Butoxycarbonyl)amino]-2-(3-fluoropropyl)hex-2-enedioic acid (10.0 mg, 0.03 mmol) was stirred in a mixture of trifluoroacetic acid (1.0 mL) and dichloromethane (1.0 mL) at r.t. for 4 h. After that the mixture was concentrated under reduced pressure, the residue was taken up in water (10 mL) and the solution was lyophilised. Yield: 6.0 mg, 0.02 mmol, 56%.

MS (ESIpos): m/z=220 [M+H]$^+$ $^1$H-NMR (300 MHz, DMSO-$d_6$): δ [ppm]=1.66-1.84 (m, 2H), 2.27 (t, 2H), 2.89 (t, 2H), 3.94 (t, 1H), 4.35 (dt, 2H), 5.92 (t, 1H), 8.13 (br. s, 1H).

Example 3

3a) (E)-(S)-5-Amino-2-(3-fluoropropyl)hex-2-enedioic acid

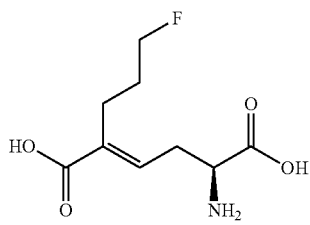

A mixture of 6-tert-Butyl 1-ethyl (E)-(S)-5-[(tert-butoxycarbonyl)amino]-2-(3-fluoropropyl)hex-2-enedioate (1e) (80.0 mg, 0.20 mmol) and 4 N aqueous hydrochloric acid (1 mL) was heated to reflux for 4 h. The mixture was then cooled to r.t., diluted with water (5 mL) and lyophilised. The crude product was purified by preparative HPLC (XBridge C18, 5 μm 150×19 mm, acetonitrile/water (0.1% TFA) gradient, 21 mL/min). Yield: 12.0 mg, 0.04 mmol, 19%.

$^1$H-NMR (400 MHz, DMSO-$d_6$): δ [ppm]=1.61-1.87 (m, 2H), 2.23-2.40 (m, 2H), 2.61-2.83 (m, 2H), 4.08-4.20 (m, 1H), 4.35 (t, 1H), 4.47 (t, 1H), 6.71 (t, 1H), 8.40 (br. s., 3H), 12.48 (br. s., 1H).

$^{19}$F-NMR (376 MHz, DMSO-$d_6$): δ [ppm]=−232.03 (m, 1F).

Example 4

Cell-Uptake Experiments

The ability of compounds from the present invention to compete with uptake of glutamic acid into tumor cells was examined. Therefore, tumor cells were co-incubated with 3H-labeled glutamic acid and several compounds from the present invention. These compounds were used in excess (1 mM) to the tracer 3H-glutamic acid. Interestingly, all tested compounds were able to reduce the uptake of glutamic acid, indicating that the same transport systems may be exploited by the test-compounds. See FIG. 1.

Example 5

5a) 6-tert-Butyl 1-ethyl (2Z,5S)-2-[3-(benzyloxy)propyl]-5-[(tert-butoxycarbonyl)amino]hex-2-enedioate 6-tert-Butyl 1-ethyl (2E,5S)-2-[3-(benzyloxy)propyl]-5-[(tert-butoxycarbonyl)amino]hex-2-enedioate

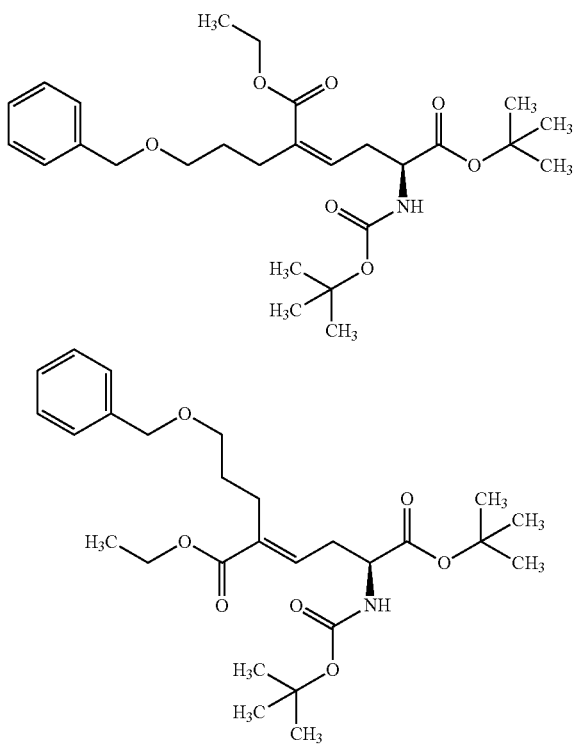

Sodium hydride (0.40 g, 60% on mineral oil, 16.7 mmol) was washed several times with hexane under an nitrogen atmosphere and was then suspended in dry THF (5 mL). Ethyl (diethoxyphosphoryl)acetate (Aldrich, 1.96 g, 8.74 mmol) was added dropwise within 20 min at r.t. as a solution in dry THF (7 mL). After stirring for 2 h at r.t. (3-Bromo-propoxymethyl)-benzene (5.0 g, 21.82 mmol) was added and the mixture was heated to reflux for 14 h. The mixture was then cooled to r.t. and the reaction was quenched by addition of sat. aq. ammonium chloride solution (10 mL). The mixture was extracted with ethyl acetate (3×10 mL) and the combined organic layers were washed with brine and dried over sodium sulphate. After evaporation of the solvent under reduced pressure the crude 5-Benzyloxy-2-(diethoxy-phosphoryl)-pentanoic acid ethyl ester was purified by column chromatography (silica, hexanes/ethyl acetate gradient). Yield: 2.33 g, 6.26 mmol, 71.6%. MS (ESIpos): m/z=373 [M+H]+.

A solution of 5-Benzyloxy-2-(diethoxyphosphoryl)-pentanoic acid ethyl ester (1.36 g, 3.65 mmol) in dry THF (5 mL) was added dropwise at 0° C. to a solution of sodium hydride (0.18 g, 7.46 mmol) in dry THF (3 mL). After stirring for 15 min tert-Butyl (2S)-2-[(tert-butoxycarbonyl)amino]-4-oxobutanoate (Example 1c) (1.0 g, 3.66 mmol) was added as a solution in dry THF (5 mL) dropwise to the reaction mixture. After stirring for 90 min at 0° C. the reaction was quenched by addition of saturated sodium bicarbonate solution (50 mL). After phase separation the aqueous layer was extracted with ethyl acetate (3×50 mL) and the combined organic layers were dried over sodium sulphate, concentrated under reduced pressure and the residue was purified by column chromatography on silica gel (hexane/ethyl acetate gradient) to give (Z)—(S)-2-(3-Benzyloxypropyl)-5-tert-butoxycarbonylamino-hex-2-enedioic acid 6-tert-butyl ester 1-ethyl ester and (E)-(S)-2-(3-Benzyloxypropyl)-5-tert-butoxycarbonylamino-hex-2-enedioic acid 6-tert-butyl ester 1-ethyl ester as a mixture of diastereomers.

Yield: 270 mg, 0.55 mmol, 15.2%.
MS (ESIpos): m/z=492 [M+H]+
1H-NMR (300 MHz, CHLOROFORM-d): δ [ppm]=1.27 (t, 3H), 1.44 (s, 9H), 1.45 (s, 9H), 1.60 (s, 1H), 1.70-1.77 (m, 2H), 2.34-2.42 (m, 2H), 2.62-2.83 (m, 2H), 3.44-3.48 (m, 2H), 4.15-4.33 (m, 3H), 4.49 (s, 2H), 5.15-5.28 (m, 1H), 5.81-6.72 (m, 1H), 7.26-7.34 (m, 5H).

5b) 1-tert-Butyl 6-ethyl (2S)-2-[(tert-butoxycarbonyl)amino]-5-(3-hydroxypropyl)hexanedioate

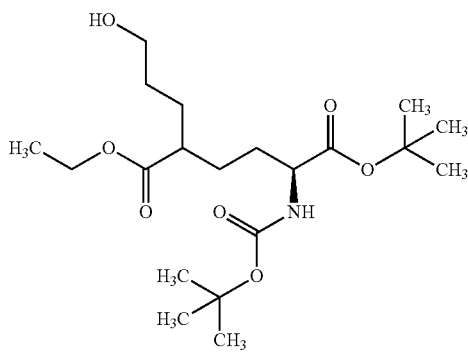 [SMILES: CCOC(=O)C(CCCO)CC[C@H](NC(=O)OC(C)(C)C)C(=O)OC(C)(C)C]

A mixture of (Z)—(S)-2-(3-Benzyloxypropyl)-5-tert-butoxycarbonylamino-hex-2-enedioic acid 6-tert-butyl ester 1-ethyl ester and (E)-(S)-2-(3-Benzyloxypropyl)-5-tert-butoxycarbonylamino-hex-2-enedioic acid 6-tert-butyl ester 1-ethyl ester (270 mg, 0.55 mmol) and palladium (30.0 mg, 10% on charcoal) in methanol (30 mL) were stirred for 6 h at r.t. under a hydrogen atmosphere. Then the mixture was filtered through Celite® and concentrated under reduced pressure. The crude product was purified by column chromatography (silica, hexane/ethyl acetate gradient).

Yield: 198 mg, 0.49 mmol, 89.4%.
MS (ESIpos): m/z=403 [M+H]+
1H-NMR (300 MHz, CHLOROFORM-d): δ [ppm]=1.25 (td, 3H), 1.44 (s, 9H), 1.46 (s, 9H), 1.58-1.78 (m, 8H), 2.34-2.45 (m, 1H), 3.63 (br, 1H), 4.12-4.19 (m, 2H), 5.04 (d, 1H).

5c) 1-tert-Butyl 6-ethyl (2S)-2-[(tert-butoxycarbonyl)amino]-5-(3-{[(4-methylphenyl)sulfonyl]oxy}propyl)hexanedioate

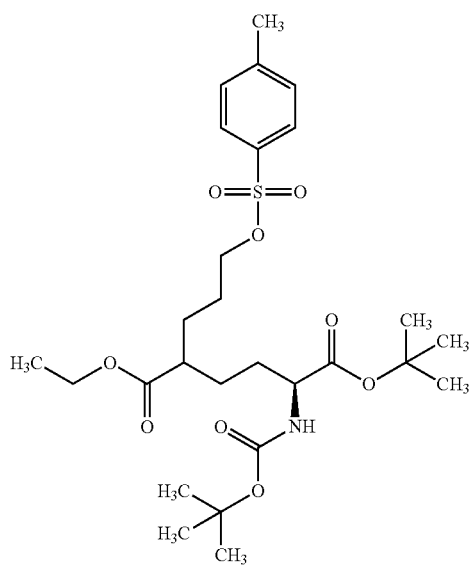

190 mg (0.47 mmol) of 1-tert-Butyl 6-ethyl (2S)-2-[(tert-butoxycarbonyl)amino]-5-(3-hydroxypropyl)hexanedioate (5b) were dissolved in 10 mL dichloromethane at 0° C. Then, 284 mg (391 microL, 2.8 mmol) triethylamine and 179 mg (0.94 mmol) p-toluene sulfonyl chloride were added at 0° C. and the mixture was stirred at this temperature for 3 h. After stirring for 18 h at r.t. the solution was concentrated under reduced pressure and the residue was purified by column chromatography on silica gel (hexane/ethyl acetate gradient) to give (S)-2-tert-Butoxycarbonylamino-5-[3-(toluene-4-sulfonyloxy)-propyl]-hexanedioic acid 1-tert-butyl ester 6-ethyl ester as a colourless oil.

Yield: 138 mg (85%).
MS (ESIpos): m/z=558 [M+H]+
1H-NMR (300 MHz, CHLOROFORM-d): δ [ppm]=1.23 (td, 3H), 1.44 (s, 9H), 1.45 (s, 9H), 1.48-1.72 (m, 8H), 2.26-

2.30 (m, 1H), 2.45 (s, 3H), 3.98-4.16 (m, 5H), 5.00-5.02 (d, 1H), 5.30 (s, 1H), 7.33-7.79 (m, 4H).

Example 6

Radiolabeling of 1-tert-Butyl 6-ethyl (2S)-2-[(tert-butoxycarbonyl)amino]-5-(3-{[(4-methylphenyl)sulfonyl]oxy}propyl)hexanedioate

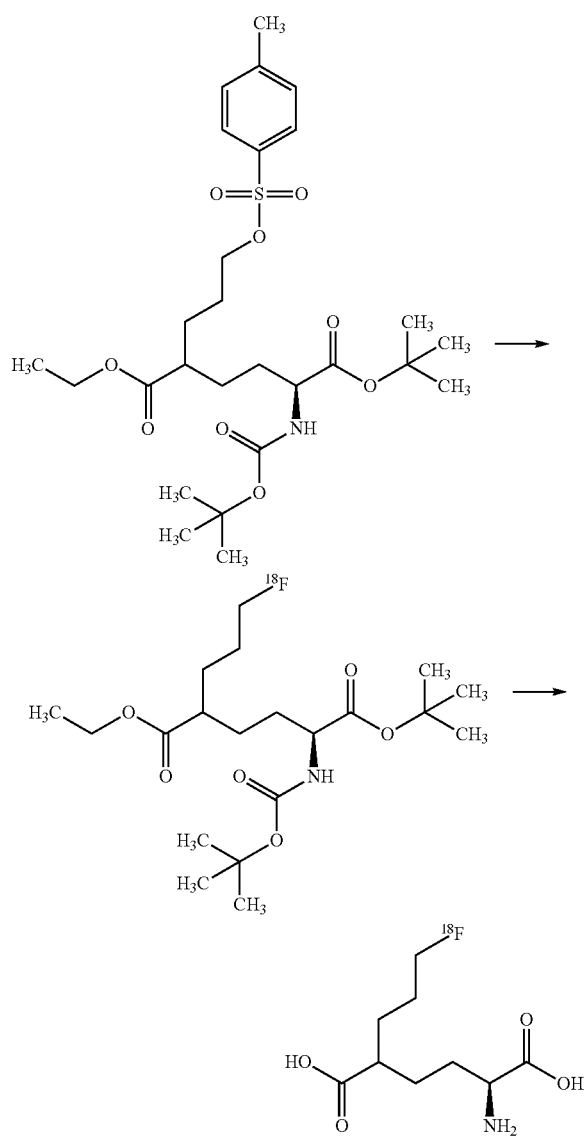

[F-18]Fluoride (1230 MBq) was trapped on an anion exchange cartridge (QMA light, Waters). The activity was eluted with potassium carbonate/kryptofix mixture (1.5 mg $K_2CO_3$, 7.5 mg $K_{222}$ in acetonitrile/water) into the reaction vessel. The mixture was dried under gentle nitrogen stream at 120° C. Drying was repeated after addition of acetonitrile (1 mL). 3 mg tosylate precursor in acetonitrile (500 μL) were added to the dried residue and the resulting solution was stirred at 120° C. for 15 min. The solution of the radiolabeled intermediate was diluted with water (30 mL) and passed through a C18 cartridge (SepPak 018 plus, Waters). The cartridge was washed with water (10 mL) and the intermediate was eluted with methanol (2 mL) (FIG. 2, analytical HPLC of radiolabeled intermediate; Chromolith SpeedRod; 0-95% acetonitrile in phosphate buffer pH 7.4; radioactivity detector). 1M LiOH (1 mL) was added and the mixture was stirred at ambient temperature for 5 min. The mixture was diluted with water (30 mL) and passed through a C18 cartridge (Sep-Pak C18 plus, Waters). The cartridge was washed with water (10 mL) and the activity was eluted with acetonitrile (1 mL). 4M HCl (1 mL) was added and the resulting mixture was heated at 140° C. for 15 min. The crude product was diluted with water (30 mL) and passed through two MCX cartridges (MCX plus, Waters). The cartridges were washed with 0.9% sodium chloride solution (10 mL). 119 MBq (20% corrected for decay) (2S)-2-amino-5-[3-[$^{18}$F]fluoropropyl]hexanedioic acid were eluted with isotonic disodium biphosphate/sodium chloride buffer (FIG. 3, analytical HPLC of (2S)-2-amino-5-[3-[$^{18}$F]fluoropropyl]hexanedioic acid after derivatization with OPA Phthaldialdehyde Reagent Solution; Pierce; Chromolith SpeedRod; 0-95% acetonitrile in phosphate buffer pH 7.4; radioactivity detector).

Example 7

(7a) di-tert-Butyl (2S)-2-[(tert-butoxycarbonyl)amino]hexanedioate

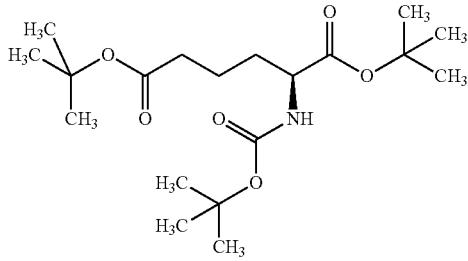 [SMILES: CC(C)(C)OC(=O)CCC[C@H](NC(=O)OC(C)(C)C)C(=O)OC(C)(C)C]

13.67 g (50 mmol) of di-tert-Butyl-L-alpha-aminoadipate (J Med Chem 1994, 37(20), 3294-3302) were dissolved in 150 mL of tetrahydrofuran (THF). 20.79 mL (150 mmol) of triethyl-amine and a solution of 14.19 g (65 mmol) di-tert-Butyl dicarbonate in 50 mL of THF were added. The mixture was stirred at room temperature overnight and the solvent was concentrated in vacuo. The residue was taken up in water and ethyl acetate, the organic phase was separated off, washed with water until neutral, dried over sodium sulphate and filtered, and the filtrate was concentrated. The crude product obtained in this manner was chromatographed on silica gel using a hexane/ethyl acetate gradient, and the appropriate fractions were combined and concentrated in vacuo.

Yield: 8.4 g (45.0%)

MS (ESIpos): m/z=374 [M+H]$^+$ $^1$H NMR (400 MHz, CHLOROFORM-d) δ ppm 1.43-1.46 (m, 27H), 1.58-1.65 (m, 3H), 1.76-1.79 (m, 1H), 2.22-2.25 (m, 2H), 4.12-4.19 (m, 1H), 5.02-5.04 (m, 1H)

(7b) (2S)-2-Amino-5-(4-cyano-3-fluorobenzyl)hexanedioic acid

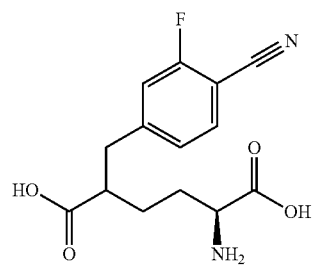 [SMILES: N#Cc1ccc(CC(CC[C@H](N)C(=O)O)C(=O)O)cc1F]

1.49 g (4 mmol) of di-tert-Butyl (2S)-2-[(tert-butoxycarbonyl)amino]hexanedioate 7a were dissolved in 50 mL of THF and cooled to −70° C. 8.8 mL (8.8 mmol) of a 1M solution of lithium bis(trimethylsilyl)amide in THF were added dropwise over a period of two hours at this temperature and the mixture was stirred at −70° C. for another 2 hours. 0.985 g (4.6 mmol) of 4-Cyano-3-fluorobenzyl bromide were then added dropwise, and after 2 h at this temperature, the cooling bath was removed and 20 mL of 2N aqueous hydrochloric acid and 100 mL of dichloromethane added. The organic phase was separated off, washed with water until neutral, dried over sodium sulphate and filtered, and the filtrate was concentrated. The crude product obtained in this manner was chromatographed on silica gel using a hexane/ethyl acetate gradient, and the appropriate fractions were combined and concentrated (150 mg) MS (ESIpos): m/z=507 [M+H]$^+$ The residue was dissolved in 1 mL of trifluoroacetic acid and stirred overnight at room temperature. The reaction mixture was then evaporated to dryness and the resulting crude product was then chromatographed with water/methanol on C18-silica gel and the resulting fractions were combined and reduced in volume by evaporation.

Yield: 0.4 mg (0.2%)
MS (ESIpos): m/z=295 [M+H]$^+$

Example 8

Cell uptake & Retention of (2S)-2-amino-5-[3-[$^{18}$F]fluoropropyl]hexanedioic acid—For determination of the biological activity of (2S)-2-amino-5-[3-[$^{18}$F]fluoropropyl]hexanedioic acid, the F-18 labeled compound was used as tracer in a cell uptake experiment using H460 (human NSCLC) cells. Approximately 100.000 cells were incubated with 0.25 MBq (2S)-2-amino-5-[3-[$^{18}$F]fluoropropyl]hexanedioic acid for up to 60 minutes in PBS-buffer containing 0.1% BSA and the cell-bound fraction was determined. A time-dependent uptake was observed during the 60 min incubation period. Approximately 20% of applied dose was taken up by the cells during the 60 min incubation period (FIG. 4).

In a second experiment, the retention of activity in tumor cells was examined. H460 cells were loaded with 0.25 MBq (2S)-2-amino-5-[3-[$^{18}$F]fluoropropyl]hexanedioic acid for 30 minutes in PBS/BSA-buffer. After this uptake, the buffer was removed and the cells were washed with PBS. The cells were then incubated with new PBS-buffer (without activity) for up to 30 min. The release of activity into the supernatant as well as the retention of activity inside the cells was examined. It was discovered, that more than 80% of activity were retained in the tumor cells after 30 min incubation under these efflux conditions (see FIG. 5).

Example 9

Biodistribution in H460 tumor bearing mice. To test the pharmacokinetic properties of (2S)-2-amino-5-[3-[$^{18}$F]fluoropropyl]hexanedioic acid, the fluorinated compound was examined in H460 tumor bearing mice. NMRI (nu/nu) mice were inoculated with H460 tumor cells 8 to 10 days before the biodistribution studies. 185 kBq of activity of the fluorinated compound was injected into each mouse. n=3 mice were used at every time point. After injection of the F18-labeled compound, mice were sacrificed at the timepoints indicated. All organs were removed and radioactivity was determined using a γ-counter. A very high uptake in the tumor (10.29% injected dose per gram of tumor at 1 h p.i.) as well as strong retention of activity (5.85% injected dose per gram of tumor at 4 h p.i.) was observed. Clearance of radioactivity takes place via the kidneys, with 67.9% of activity being excreted at 1 h p.i. High tumor to blood (ratio 34.7) as well as tumor to muscle ratios (ratio 62.6) suggest excellent PET imaging properties of (2S)-2-amino-5-[3-[$^{18}$F]fluoropropyl]hexanedioic acid (see Table 1).

TABLE 1

Biodistribution in H460 tumor bearing mice

| timepoint: | 0.25 h | | 0.5 h | | 1.0 h | | 2.0 h | | 4.0 h | |
|---|---|---|---|---|---|---|---|---|---|---|
| | | S.D. | | S.D. | | S.D. | | S.D. | | S.D. |
| % Dosis/g | | | | | | | | | | |
| spleen | 5.15 | 0.78 | 4.37 | 1.00 | 2.87 | 0.21 | 1.78 | 0.19 | 1.27 | 0.27 |
| liver | 0.84 | 0.03 | 0.61 | 0.06 | 0.53 | 0.22 | 0.32 | 0.14 | 0.15 | 0.03 |
| kidney | 17.49 | 1.44 | 5.64 | 1.58 | 3.10 | 0.31 | 1.17 | 0.24 | 0.72 | 0.20 |
| lung | 3.22 | 2.14 | 1.62 | 0.36 | 1.43 | 0.14 | 1.04 | 0.19 | 0.81 | 0.10 |
| bone | 0.57 | 0.08 | 0.53 | 0.05 | 0.46 | 0.01 | 0.40 | 0.08 | 0.39 | 0.04 |
| heart | 0.60 | 0.14 | 0.24 | 0.04 | 0.18 | 0.02 | 0.13 | 0.01 | 0.08 | 0.01 |
| brain | 0.18 | 0.04 | 0.12 | 0.02 | 0.11 | 0.01 | 0.08 | 0.03 | 0.08 | 0.05 |
| fat | 0.25 | 0.11 | 0.18 | 0.12 | 0.14 | 0.09 | 0.07 | 0.01 | 0.06 | 0.02 |
| thyroid | 2.05 | 0.48 | 1.58 | 0.30 | 1.57 | 0.21 | 1.37 | 0.10 | 0.98 | 0.23 |
| gallbladder | 1.08 | 0.26 | 0.47 | 0.06 | 0.57 | 0.15 | 0.48 | 0.08 | 0.70 | 0.51 |
| muscle | 0.37 | 0.05 | 0.15 | 0.03 | 0.16 | 0.01 | 0.11 | 0.01 | 0.09 | 0.01 |
| tumor | 10.58 | 2.01 | 8.17 | 2.81 | 10.29 | 1.85 | 6.72 | 2.57 | 5.85 | 0.37 |
| skin | 2.82 | 0.68 | 2.51 | 0.22 | 2.43 | 0.22 | 1.97 | 0.45 | 1.31 | 0.58 |
| blood | 1.36 | 0.17 | 0.45 | 0.13 | 0.30 | 0.01 | 0.15 | 0.01 | 0.10 | 0.01 |
| tail | 8.12 | 4.19 | 5.67 | 1.87 | 2.33 | 1.17 | 1.64 | 0.85 | 3.43 | 1.62 |
| stomach | 10.27 | 1.32 | 7.82 | 1.21 | 4.47 | 0.58 | 3.35 | 1.39 | 1.27 | 0.18 |
| uterus | 4.37 | 2.00 | 2.63 | 1.16 | 2.45 | 0.82 | 2.72 | 1.05 | 1.41 | 0.89 |
| ovaries | 4.04 | 1.87 | 6.23 | 3.77 | 1.86 | 0.88 | 1.58 | 0.17 | 2.18 | 1.02 |

TABLE 1-continued

Biodistribution in H460 tumor bearing mice

| | 0.25 h | | 0.5 h | | 1.0 h | | 2.0 h | | 4.0 h | |
|---|---|---|---|---|---|---|---|---|---|---|
| | | S.D. | | S.D. | | S.D. | | S.D. | | S.D. |
| intestine | 2.34 | 0.46 | 1.96 | 0.52 | 1.77 | 0.54 | 1.23 | 0.35 | 0.97 | 0.40 |
| pancreas | 26.85 | 4.83 | 21.26 | 5.99 | 16.68 | 3.79 | 7.70 | 0.58 | 4.51 | 0.76 |
| adrenals | 1.18 | 0.16 | 0.67 | 0.13 | 0.61 | 0.17 | 0.52 | 0.24 | 0.61 | 0.24 |
| summary | | | | | | | | | | |
| recovery | 88.24 | 1.31 | 91.75 | 7.53 | 102.93 | 2.93 | 94.72 | 2.31 | 94.87 | 6.50 |
| organs | 39.99 | 2.19 | 32.54 | 4.77 | 25.76 | 2.40 | 17.68 | 1.17 | 12.00 | 3.50 |
| carcass | 18.07 | 4.79 | 10.51 | 3.51 | 9.28 | 2.60 | 9.12 | 1.45 | 4.03 | 1.22 |
| urine | 30.17 | 7.83 | 48.69 | 15.64 | 67.90 | 5.94 | 68.67 | 3.41 | 77.27 | 9.08 |
| faeces | — | — | 0.00 | 0.01 | 0.00 | 0.00 | 0.01 | 0.01 | 2.10 | 2.28 |
| Tumor/Tissue | | | | | | | | | | |
| kidney | 0.60 | 0.08 | 1.43 | 0.24 | 3.31 | 0.35 | 6.15 | 3.56 | 8.78 | 3.45 |
| bone | 18.92 | 5.25 | 15.47 | 5.40 | 22.16 | 3.44 | 18.25 | 10.11 | 15.04 | 2.73 |
| heart | 17.61 | 0.60 | 34.35 | 9.89 | 57.45 | 15.99 | 54.23 | 23.86 | 68.93 | 2.17 |
| brain | 58.25 | 6.75 | 69.00 | 32.62 | 93.25 | 12.38 | 87.08 | 40.37 | 83.21 | 35.77 |
| muscle | 28.44 | 1.24 | 54.98 | 12.2 | 62.55 | 8.07 | 62.45 | 18.66 | 64.19 | 3.01 |
| skin | 3.82 | 0.60 | 3.20 | 0.89 | 4.24 | 0.63 | 3.59 | 1.58 | 5.40 | 3.28 |

Example 10

PET imaging. (2S)-2-amino-5-[3-[$^{18}$F]fluoropropyl]hexanedioic acid was examined in NCI-H460 (human NSCLC) tumor bearing nude-rats (RH-Foxn1 nu/nu) using PET-Imaging. 8.35 MBq of (2S)-2-amino-5-[3-[$^{18}$F]fluoropropyl]hexanedioic acid was injected into the rat. PET images were acquired at 60 min p.i. for 10 min. The tumor was very well visible in the images. 3.2% of the injected dose was taken up per gram of tumor as was determined by region of interest (ROI) analysis (FIG. 6).

Example 11

The ability of (2S)-2-Amino-5-(4-cyano-3-fluorobenzyl) hexanedioic acid to compete with uptake of glutamic acid derivatives into tumor cells was examined. Therefore, tumor cells were co-incubated with a radiolabeled glutamic acid derivative and (2S)-2-Amino-5-(4-cyano-3-fluorobenzyl) hexanedioic acid. This compounds was used in large excess to the tracer. Two concentrations were examined (1 mM an 0.1 mM). Interestingly, this compound strongly reduces the uptake of the radiolabeled glutamic acid derivative, indicating that the same transport systems may be exploited by the test-compounds, (FIG. 7).

The invention claimed is:
1. A compound of formula (II):

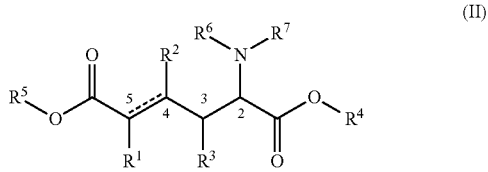

(II)

wherein
- - - indicates a single or double bond between the C-4 and C-5 positions of the compound;
$R^2$ and $R^3$ are Hydrogen;
$R^1$ is X, wherein X is
- a fluorine atom, F, with the proviso that there is no double bond between C-4 and C-5,
- branched or straight-chain F—$C_1$-$C_{10}$ alkyl wherein the alkyl chain is optionally interrupted by 1 or 2 oxygen atoms with the proviso that there are at least two methylene groups between two oxygen atoms,
- branched or straight-chain F—$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms,
- F—$C_6$-$C_{10}$ mono- or bicyclic aryl-$(CH_2)_n$ wherein n=1 to 3,
- F-mono- or bicyclic heteroaryl-$(CH_2)_n$ wherein n=1 to 3,
- F—$C_3$-$C_6$ cycloalkyl with the proviso that F is attached to one of the $CH_2$ groups of the ring,
- F—$C_3$-$C_6$ cycloalkyl-$(CH_2)_n$, wherein n=1 to 3, with the proviso that F is attached to one of the $CH_2$ groups of the ring,
- F—$C_6$-$C_{10}$ mono- or bicyclic aryl-$(CH_2)_n$—O, wherein n=1 to 3 with the proviso that there is no double bond between C-4 and C-5, or
- F-mono- or bicyclic heteroaryl-$(CH_2)_n$—O wherein n=1 to 3, with the proviso that there is no double bond between C-4 and C-5;

$R^4$=Hydrogen or O-protecting group;
$R^5$=Hydrogen or O-protecting group;
$R^6$=Hydrogen or N-protecting group;
$R^7$=Hydrogen or N-protecting group;
or the group $NR^6R^7$ is a 1,3-dioxo-1,3-dihydro-2H-isoindol-2-yl (phthalimido) or an azido group,
wherein heteroaryl comprises 5 to 10 ring atoms wherein 1 or 2 ring atoms are heteroatoms,
wherein the fluorine atom, F, means fluorine optionally in an isotope form, and
encompassing single isomers, E and Z-isomers, diastereomers, enantiomers, mixtures thereof and suitable salts thereof.

2. A compound of claim 1 wherein at least one of the substituents $R^4$, $R^5$, $R^6$, or $R^7$ is not Hydrogen.

3. The compound according to claim 1 wherein X is a fluorine atom, F, with the proviso that there is no double bond between C-4 and C-5 or X is a branched or straight-chain F—$C_1$-$C_{10}$ alkyl.

4. The compound according to claim 1 wherein the fluorine atom, F, contained in each option for X is a $^{18}$F or $^{19}$F isotope.

5. The compound according to claim 1 selected from

Ammonium hydrogen (2S)-2-amino-5-(3-fluoropropyl)hexanedioate

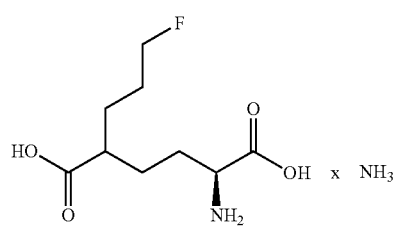

(2S)-2-Amino-5-(3-[$^{18}$F]fluoropropyl)hexanedioic acid

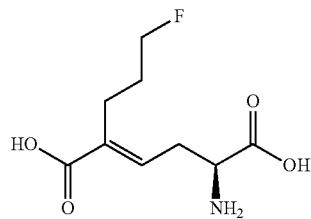 [SMILES: N[C@@H](C/C=C(\CCCF)C(=O)O)C(=O)O]

(E)-(S)-5-Amino-2-(3-fluoropropyl)hex-2-enedioic acid

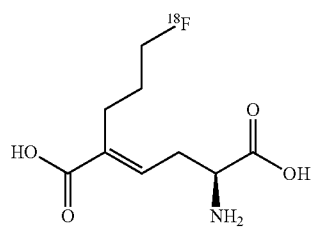 [SMILES: N[C@@H](C/C=C(\CCC[18F])C(=O)O)C(=O)O]

(E)-(S)-5-Amino-2-(3-[$^{18}$F]fluoropropyl)hex-2-enedioic acid

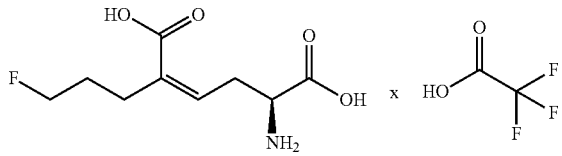 [SMILES: N[C@@H](C/C=C(/CCCF)C(=O)O)C(=O)O ; O=C(O)C(F)(F)F]

(Z)—(S)-5-Amino-2-(3-fluoropropyl)hex-2-enedioic acid-trifluoroacetate

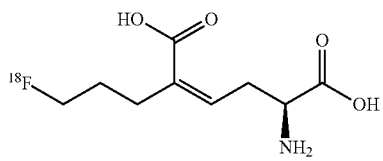 [SMILES: N[C@@H](C/C=C(/CCC[18F])C(=O)O)C(=O)O]

(Z)—(S)-5-Amino-2-(3-[$^{18}$F]fluoropropyl)hex-2-enedioic acid

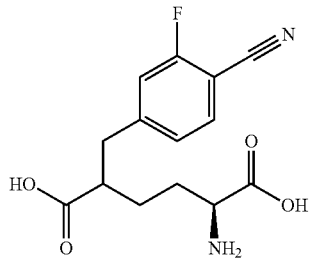

(2S)-2-Amino-5-(4-cyano-3-fluorobenzyl)hexanedioic acid

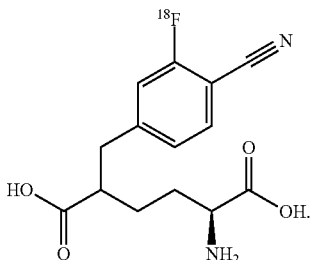

(2S)-2-Amino-5-(4-cyano-3-[$^{18}$F]fluorobenzyl)hexanedioic acid

6. A compound according to claim 1 selected from
6-tert-Butyl 1-ethyl (E)-(S)-5-[(tert-butoxycarbonyl)amino]-2-(3-fluoropropyl)hex-2-enedioate

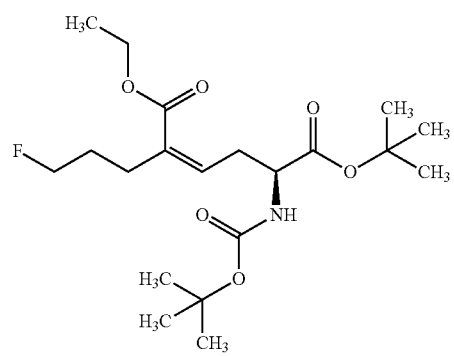

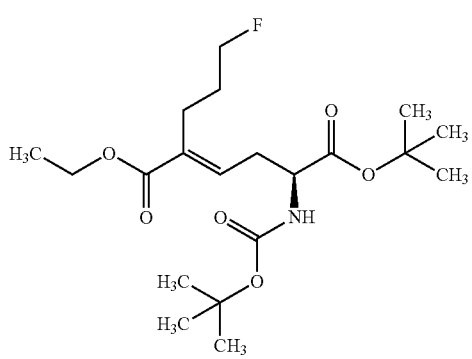

1-tert-Butyl 6-ethyl (2S)-2-[(tert-butoxycarbonyl)amino]-5-(3-fluoropropyl)hexanedioate

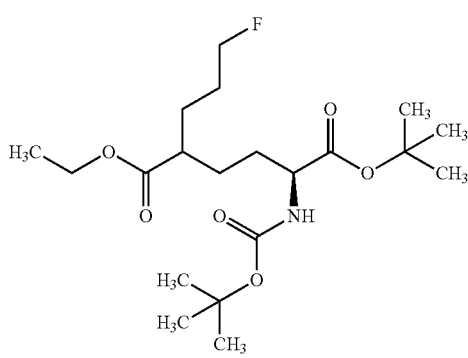 [SMILES: CCOC(=O)C(CCCF)CC[C@H](NC(=O)OC(C)(C)C)C(=O)OC(C)(C)C]

1-tert-Butyl 6-hydrogen (2S)-2-[(tert-butoxycarbonyl)amino]-5-(3-fluoropropyl)hexanedioate

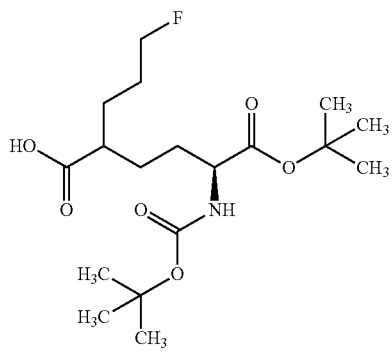

(Z)—(S)-5-[(tert-Butoxycarbonyl)amino]-2-(3-fluoropropyl)hex-2-enedioic acid

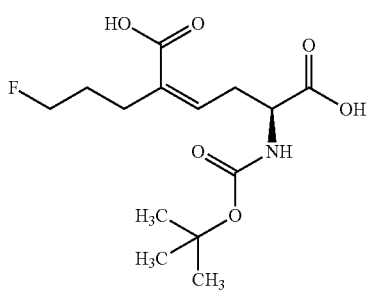 [SMILES: CC(C)(C)OC(=O)N[C@@H](C/C=C(/CCCF)C(=O)O)C(=O)O]

Di-tert-butyl (2S)-2-[(tert-butoxycarbonyl)amino]-5-(4-cyano-3-fluorobenzyl)hexanedioate

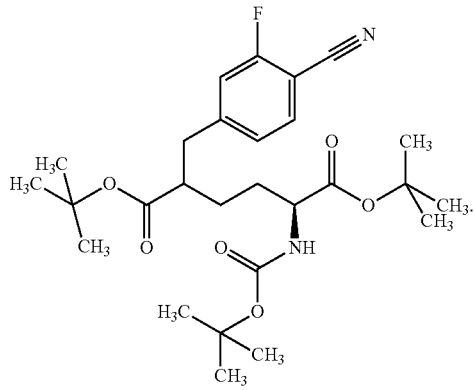 [SMILES: CC(C)(C)OC(=O)N[C@@H](CCC(Cc1ccc(C#N)c(F)c1)C(=O)OC(C)(C)C)C(=O)OC(C)(C)C]

7. A compound of formula (III)

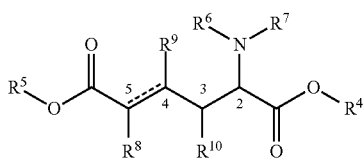

wherein

- - - indicates a single or double bond between the C-4 and C-5 positions of the compound;

$R^9$ and $R^{10}$ are Hydrogen;

$R^8$ is Y, wherein Y is

Leaving Group (LG) with the proviso that there is no double bond between C-4 and C-5, branched or straight-chain LG-$C_1$-$C_{10}$ alkyl wherein the carbon chain is optionally interrupted by 1 or 2 oxygen atoms with the proviso that there are at least two methylene groups between two oxygen atoms, branched or straight-chain LG-$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms, LG-$C_6$-$C_{10}$ mono- or bicyclic aryl-$(CH_2)_n$ wherein n=1 to 3, LG-mono- or bicyclic heteroaryl-$(CH_2)_n$ wherein n=1 to 3, and wherein heteroaryl comprises 5 to 10 ring atoms wherein 1 or 2 ring atoms are hetero-atoms, LG-$C_3$-$C_6$ cycloalkyl with the proviso that LG is attached to one of the $CH_2$ groups of the ring, LG-$C_3$-$C_6$ cycloalkyl-$(CH_2)_n$, wherein n=1 to 3, with the proviso that LG is attached to one of the $CH_2$ groups of the ring, LG-$C_6$-$C_{10}$ mono- or bicyclic aryl-$(CH_2)_n$—O, wherein n=1 to 3 with the proviso that there is no double bond between C-4 and C-5 or LG-mono- or bicyclic heteroaryl-$(CH_2)_n$—O wherein n=1 to 3, with the proviso that there is no double bond between C-4 and C-5 and wherein heteroaryl comprises 5 to 10 ring atoms wherein 1 or 2 atom is a hetero-atom;

$R^4$=O-protecting group;
$R^5$=O-protecting group;
$R^6$=N-protecting group;
$R^7$=Hydrogen or N-protecting group
or the group $NR^6R^7$ is a 1,3-dioxo-1,3-dihydro-2H-isoindol-2-yl (phthalimido) or an azido group and
encompassing single isomers, E and Z-isomers, diastereomers, enantiomers, mixtures thereof and suitable salts thereof.

8. The compound according to claim 7 wherein
if LG is attached to an sp$^3$-hybridized carbon atom then the Leaving Group (LG) is selected from the group of
Halogen,
Methylsulfonyloxy,
Trifluoromethylsulfonyloxy,
(4-Nitrophenyl) sulphonyloxy
Nonafluorobutylsulfonyloxy,
(4-Methylphenyl)sulfonyloxy, and
iodo,
or
if LG is attached to aryl or heteroaryl, then the Leaving Group (LG) is selected from the group of
Halogen,
nitro,
trimethyl ammonium,
4-methoxyphenyliodonium, and
2-thienyliodonium;
$R^4$ and $R^5$ is an O-protecting group selected from:
Methyl, Ethyl, Propyl, Butyl, t-Butyl, Allyl, Benzyl, 4-Methoxybenzyl, or 4-Methoxyphenyl,
and N-protecting groups are selected from:
Carbobenzyloxy (Cbz), p-Methoxybenzyl carbonyl (Moz or MeOZ), tert-Butyloxycarbonyl (BOC), 9-Fluorenylmethyloxycarbonyl (FMOC), Benzyl (Bn), p-Methoxybenzyl (PMB), 3,4-Dimethoxybenzyl (DMPM), Triphenylmethyl or p-methoxyphenyl (PMP) or the group $NR^6R^7$ is a 1,3-dioxo-1,3-dihydro-2H-isoindol-2-yl (phthalimido) or an azido group.

9. A composition comprising a compound according to claim 1 or a mixture thereof and a pharmaceutically acceptable carrier or diluent.

10. The method for preparing a compound of claim 1 wherein the method comprises the steps
Coupling a compound of the following Formula (III) with a fluorine atom, F, containing moiety,

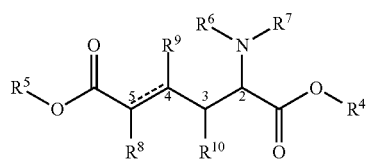

(III)

wherein
- - - indicates a single or double bond between the C-4 and C-5 positions of the compound;
$R^9$ and $R^{10}$ are Hydrogen;
$R^8$ is Y, wherein Y is
Leaving Group (LG) with the proviso that there is no double bond between C-4 and C-5,
branched or straight-chain LG-$C_1$-$C_{10}$ alkyl wherein the carbon chain is optionally interrupted by 1 or 2 oxygen atoms with the proviso that there are at least two methylene groups between two oxygen atoms,
branched or straight-chain LG-$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms,
LG-$C_6$-$C_{10}$ mono- or bicyclic aryl-$(CH_2)_n$ wherein n=1 to 3,
LG-mono- or bicyclic heteroaryl-$(CH_2)_n$ wherein n=1 to 3, and wherein heteroaryl comprises 5 to 10 ring atoms wherein 1 or 2 ring atoms are hetero-atoms,
LG-$C_3$-$C_6$ cycloalkyl with the proviso that LG is attached to one of the $CH_2$ groups of the ring,
LG-$C_3$-$C_6$ cycloalkyl-$(CH_2)_n$, wherein n=1 to 3, with the proviso that LG is attached to one of the $CH_2$ groups of the ring,
LG-$C_6$-$C_{10}$ mono- or bicyclic aryl-$(CH_2)_n$—O, wherein n=1 to 3 with the proviso that there is no double bond between C-4 and C-5 or
LG-mono- or bicyclic heteroaryl-$(CH_2)_n$—O wherein n=1 to 3 with the proviso that there is no double bond between C-4 and C-5 and
wherein heteroaryl comprises 5 to 10 ring atoms wherein 1 or 2 atom is a hetero-atom;
$R^4$=O-protecting group;
$R^5$=O-protecting group;
$R^6$=N-protecting group;
$R^7$=Hydrogen or N-protecting group
or the group $NR^6R^7$ is a 1,3-dioxo-1,3-dihydro-2H-isoindol-2-yl (phthalimido) or an azido group,
optionally removing the O-protecting groups and N-protecting groups and
Optionally converting the obtained compound into a suitable salt of inorganic or organic acids thereof, hydrates, complexes, esters, amides, or solvates thereof.

11. A method for imaging or diagnosing proliferative diseases comprising the steps:
Administering to a mammal an effective amount of a compound of claim 1 wherein $R^4$, $R^5$, $R^6$ and $R^7$ are hydrogen and F is fluorine in an isotope form,
Obtaining images of the mammal and
Assessing images.

12. A method for conducting biological assays or chromatographic identification which comprises using a compound of claim 1 for assaying or chromatography.

13. A kit comprising a sealed vial containing a predetermined quantity of a compound of claim 7 or suitable salts of inorganic or organic acids thereof, hydrates, complexes, esters, amides, and solvates thereof.

14. A compound of claim 1 wherein $R^4$, $R^5$, $R^6$ and $R^7$ are hydrogen and F is fluorine in an isotope form.

15. A compound of claim 1 wherein n=1.

16. A compound of claim 1 wherein X is:
branched or straight-chain F—$C_1$-$C_{10}$ alkyl wherein the alkyl chain is optionally interrupted by 1 or 2 oxygen atoms with the proviso that there are at least two methylene groups between two oxygen atoms,
branched or straight-chain F—$C_1$-$C_{10}$ alkoxy with the proviso that there is no double bond between C-4 and C-5 and wherein the carbon chain is optionally interrupted by 1 additional oxygen atom with the proviso that there are at least two methylene groups between two oxygen atoms, F—$C_6$-$C_{10}$ mono- or bicyclic aryl-$(CH_2)_n$ wherein n=1 to 3, F-mono- or bicyclic heteroaryl-$(CH_2)_n$ wherein n=1 to 3, F—$C_3$-$C_6$ cycloalkyl with the proviso that F is attached to one of the $CH_2$ groups of the ring, F—$C_3$-$C_6$ cycloalkyl-$(CH_2)_n$, wherein n=1 to 3, with the proviso that F is attached to one of the $CH_2$ groups of the ring, F—$C_6$-$C_{10}$ mono- or bicyclic aryl-$(CH_2)_n$—O, wherein n=1 to 3 with the proviso that there is no double bond between C-4 and C-5, or F-mono- or bicyclic heteroaryl-$(CH_2)_n$—O wherein n=1 to 3, with the proviso that there is no double bond between C-4 and C-5.

\* \* \* \* \*